(12) United States Patent
Matsukuma et al.

(10) Patent No.: US 9,932,625 B2
(45) Date of Patent: Apr. 3, 2018

(54) METHOD FOR IDENTIFICATION AND DETECTION OF MUTANT GENE USING INTERCALATOR

(71) Applicants: WAKO PURE CHEMICAL INDUSTRIES, LTD., Osaka-shi, Osaka (JP); KANAGAWA PREFECTURAL HOSPITAL ORGANIZATION, Yokohama-shi, Kanagawa (JP)

(72) Inventors: Shoichi Matsukuma, Yokohama (JP); Tomokazu Ishikawa, Amagasaki (JP); Tatsuo Kurosawa, Amagasaki (JP)

(73) Assignees: WAKO PURE CHEMICAL INDUSTRIES, LTD., Osaka (JP); KANAGAWA PREFECTURAL HOSPITAL ORGANIZATION, Yokohama (JP)

( * ) Notice: Subject to any disclaimer, the term of this patent is extended or adjusted under 35 U.S.C. 154(b) by 634 days.

(21) Appl. No.: 14/387,150

(22) PCT Filed: Mar. 22, 2013

(86) PCT No.: PCT/JP2013/058212
§ 371 (c)(1),
(2) Date: Sep. 22, 2014

(87) PCT Pub. No.: WO2013/141332
PCT Pub. Date: Sep. 26, 2013

(65) Prior Publication Data
US 2015/0050749 A1 Feb. 19, 2015

(30) Foreign Application Priority Data
Mar. 22, 2012 (JP) .................... 2012-065231

(51) Int. Cl.
*C12Q 1/68* (2018.01)

(52) U.S. Cl.
CPC ......... *C12Q 1/6823* (2013.01); *C12Q 1/6827* (2013.01); *G01N 2458/30* (2013.01)

(58) Field of Classification Search
None
See application file for complete search history.

(56) References Cited

U.S. PATENT DOCUMENTS 5,698,394 A * 12/1997 Duhamel ............... C12Q 1/689
435/6.15
2007/0020672 A1* 1/2007 Wittwer ............... C07D 413/06
435/6.11
2013/0217016 A1* 8/2013 Matsukuma ......... C12Q 1/6827
435/6.11

FOREIGN PATENT DOCUMENTS

JP 2007-061080 A 3/2007
WO WO2012-039481 * 3/2012 ............. C12Q 1/68

OTHER PUBLICATIONS

Benson SC, Singh P, Glazer AN. Heterodimeric DNA-binding dyes designed for energy transfer: synthesis and spectroscopic properties. Nucleic Acids Res. Dec. 11, 1993; 21(24):5727-35.*
GelRed Manual by Biotium, Dec. 12, 2012, pp. 1-4.*
Glazer AN, Rye HS. Stable dye-DNA intercalation complexes as reagents for high-sensitivity fluorescence detection. Nature. Oct. 29, 1992; 359(6398):859-61.*
Matsukuma S, Yoshihara M, Kasai F, Kato A, Yoshida A, Akaike M, Kobayashi O, Nakayama H, Sakuma Y, Yoshida T, Kameda Y, Tsuchiya E, Miyagi Y. Rapid and simple detection of hot spot point mutations of epidermal growth factor receptor, BRAF, and NRAS in cancers using the loop-hybrid mobility shift assay. J Mol Diagn. Sep. 2006; 8(4):504-12.*
Matsukuma S, Yoshihara M, Suda T, Shiozawa M, Akaike M, Ishikawa T, Koizume S, Sakuma Y, Miyagi Y. Differential detection of KRAS mutations in codons 12 and 13 with a modified loop-hybrid (LH) mobility shift assay using an insert-type LH-generator. Clin Chim Acta. Sep. 18, 2011; 412(19-20):1874-8.*
Molecular Probes Handbook, 11th Edition (2010), chapter 8, Nucleic Acid Detection and Analysis by ThermoFischer Scientific: pp. 303-360.*
Rye HS, Yue S, Wemmer DE, Quesada MA, Haugland RP, Mathies RA, Glazer AN. Stable fluorescent complexes of double-stranded DNA with bis-intercalating asymmetric cyanine dyes: properties and applications. Nucleic Acids Res. Jun. 11, 1992; 20(11):2803-12.*
Zhou L, Myers AN, Vandersteen JG, Wang L, Wittwer CT. Closed-tube genotyping with unlabeled oligonucleotide probes and a saturating DNA dye. Clin Chem. Aug. 2004; 50(8):1328-35.*
Matsukuma et al. Rapid and simple detection of hot spot point mutations of epidermal growth factor receptor, BRAF, and NRAS in cancers using the loop-hybrid mobility shift assay. J Mol Diagn. Sep. 2006; 8(4):504-12. (Year: 2006).*
Matsukuma et al., *Clinica Chimica Acta*, 412: 1668-1672 (2011).
Japanese Patent Office, International Search Report in International Patent Application No. PCT/JP2013/058212 (dated Jun. 11, 2013).

* cited by examiner

*Primary Examiner* — Samuel C Woolwine
*Assistant Examiner* — Olayinka A Oyeyemi
(74) *Attorney, Agent, or Firm* — Leydig, Voit & Mayer, Ltd.

(57) ABSTRACT

The invention provides a method for detection of mutant-type DNA or/and wild-type DNA by contacting at least one of a single-stranded DNA having a substituted nucleotide, a deficient nucleotide region, or an inserted nucleotide region (mutant-type DNA), or/and a wild-type single-stranded DNA corresponding to the mutant-type DNA (wild-type DNA) with a probe hybridizing with both single-stranded DNAs, to form a hybrid with the mutant-type DNA (mutant-type hybrid) or/and a hybrid with the wild-type DNA (wild-type hybrid) (at least one of the obtained mutant-type hybrid and wild-type hybrid has a loop structure), (2) contacting the obtained mutant-type hybrid or/and wild-type hybrid with an intercalator, and (3) detecting the presence or absence of the mutant-type DNA or/and the wild-type DNA by separating the conjugate of mutant-type hybrid and intercalator or/and the conjugate of wild-type hybrid and intercalator.

16 Claims, 31 Drawing Sheets

Mutant-type hybrid

Wild-type hybrid

Wild-type hybrid

Wild-type hybrid

Mutant-type hybrid

Mutant-type hybrid

Wild-type hybrid

Wild-type hybrid

Mutant-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Wild-type hybrid

Wild-type hybrid

Mutant-type hybrid

Wild-type hybrid

Mutant-type hybrid

Wild-type hybrid

Mutant-type hybrid

Wild-type hybrid

Mutant-type hybrid

Wild-type hybrid

Wild-type hybrid

Wild-type hybrid

Mutant-type hybrid

Wild-type hybrid

Mutant-type hybrid

Migration time

① ② ③ ④ ⑤ ⑥

METHOD FOR IDENTIFICATION AND DETECTION OF MUTANT GENE USING INTERCALATOR

CROSS-REFERENCE TO RELATED APPLICATIONS

This patent application is the U.S. national phase of International Patent Application No. PCT/JP2013/058212, filed Mar. 22, 2013, which claims the benefit of Japanese Patent Application No. 2012-065231, filed on Mar. 22, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,629 bytes ASCII (Text) file named "718608SequenceListing.txt," created Sep. 17, 2014.

TECHNICAL FIELD

The present invention relates to a method for detecting mutant-type DNA or wild-type DNA with high accuracy by loop hybrid method using intercalator.

BACKGROUND ART

In recent years, the presence or absence of a mutation in a particular gene has been emphasized in various fields. For example, in DNA testing in forensic medicine, confirmation of the presence and absence of single nucleotide substitution by mutation or polymorphism in DNA has already been well known as a method for individual identification. Also, in the field of medicine, correlation between specific genetic polymorphism and drug sensitivity has been known, and trials to reduce the risk of drug-induced health disaster have been carried out by investigating specific genetic polymorphism. In addition, the detection of mutation in the gene is also employed for detection of a mutant-type DNA holder of hereditary disease, and is gaining importance than before.

And, as a method for detecting gene mutation, a loop hybrid method (LH method) in which single-stranded oligo DNA is added to the reaction solution after the PCR reaction of DNA fragment and hybridized with objective DNA fragment, and the obtained hybrid is separated by electrophoresis based on the structural differences, and discriminate the separated mutant gene by reacting with intercalator as needed, has been known (Patent Literature 1, Non-patent Literature 1).

CITATION LIST

Patent Literature

Patent Literature 1: JP-A-2007-61080.

Non-Patent Literature

Non-patent Literature 1: Clinica Chimica Acta, 412, 1688-1672.

SUMMARY OF INVENTION

Problem to be Solved by the Invention

The above-described LH method is a useful method in the detection of mutant-type DNA, however, this method has a problem that it is difficult to separate and detect mutant-type DNA and wild-type DNA which have a sequence of same number of nucleotides, or it is difficult to separate and detect mutant-type DNAs both of which have a sequence of same number of nucleotides. Therefore, the present invention addresses the problem of improving separation performance in separating a hybrid of mutant-type DNA and a probe or/and a hybrid of wild-type type DNA and a probe, said hybrids being obtained by the LH method.

Solution to Problem

In view of the above-described circumstances, the present inventors have studied extensively, and as a result, have found surprisingly that, when a hybrid obtained by the LH method is subjected to separation by electrophoresis after contacting with an intercalator, that is, when a conjugate of a hybrid and an intercalator is separated by electrophoresis, separation performance is improved. Thereby the separation/detection of mutant-type DNA and wild-type DNA which have a sequence of same number of nucleotides, or the separation/detection of mutant-type DNAs both of which have a sequence of same number of nucleotides would become possible, and have completed the present invention. That is, the present invention relates to "a method for detection of the mutant-type DNA or/and wild-type DNA characterized by comprising the following steps (1) to (3):
(1) a step in which at least one of a single-stranded DNA having a substituted nucleotide, a deficient nucleotide region, or an inserted nucleotide region (mutant-type DNA), or/and a wild-type single-stranded DNA corresponding to the mutant-type DNA (wild-type DNA) are contacted with a probe hybridizing with both single-stranded DNAs, to form a hybrid (mutant-type hybrid) with the mutant-type DNA or/and a hybrid (wild-type hybrid) with the wild-type DNA (in this regard however, at least one of the mutant-type hybrid and the wild-type hybrid has a loop structure),
(2) a step in which the obtained mutant-type hybrid or/and wild-type hybrid is contacted with an intercalator, and
(3) a step in which the presence or absence of the mutant-type DNA or/and the wild-type DNA is detected by separating the conjugate of mutant-type hybrid and intercalator or/and the conjugate of wild-type hybrid and intercalator.

Advantageous Effects of Invention

According to the detection method of the present invention, since the separation performance of the mutant-type hybrid and the wild-type hybrid, or the separation performance between mutant-type hybrids valiations is high, even if the number of nucleotides in the mutant-type DNA and wild-type DNA is same, or even if the mutant-type DNA is plural and each mutant-type DNA has the same number of nucleotides, separation and discrimination is enabled. As a result, even if a mutant-type DNA has various polymorphisms, mutant-type DNA and wild-type DNA can be detected. In particular, when the electrophoretic method is employed, the above-described effects is demonstrated prominently.

BRIEF DESCRIPTION OF DRAWINGS

FIG. 1 illustrates nucleic acid mutations.

FIG. 2 illustrates an embodiment in which mutant-type DNA having a substituted nucleotide is detected.

FIG. 4 illustrates an embodiment in which mutant-type DNA having a substituted nucleotide is detected.

FIG. 5 illustrates an embodiment in which mutant-type DNA having a substituted nucleotide is detected.

FIG. 6 illustrates an embodiment in which mutant-type DNA having a substituted nucleotide is detected.

FIG. 7 illustrates an embodiment in which mutant-type DNA having a substituted nucleotide is detected.

FIG. 9 illustrates an embodiment in which a probe with a nucleotide sequence that does not hybridize with wild-type DNA nor with mutant-type DNA is inserted into a nucleotide sequence complementary to the normal nucleotide region or next to the nucleotide sequence complementary to the normal nucleotide region.

FIG. 10 illustrates an embodiment in which a probe consists of a nucleotide sequence complementary to the entire nucleotide sequence or part of the nucleotide sequence of the mutant DNA.

FIG. 12 illustrates an embodiment in which a probe forms a wild-type hybrid having a loop structure and a mutant-type hybrid without a loop structure.

FIG. 13 illustrates an embodiment in which a probe with a nucleotide sequence that does not hybridize with wild-type DNA nor with mutant-type DNA is inserted into a nucleotide sequence complementary to the normal nucleotide region or next to the nucleotide sequence complementary to the normal nucleotide region.

FIG. 14 illustrates an embodiment in which a probe consists of a nucleotide sequence complementary to the entire nucleotide sequence or part of the nucleotide sequence of the wild-type DNA.

FIG. 15 illustrates an embodiment in which a probe with a nucleotide sequence for constituting a loop in the wild-type hybrid is excluded from the probe at a nucleotide complementary to a nucleotide next to a normal nucleotide region as a base point.

DESCRIPTION OF INVENTION

[Mutant-Type DNA and Wild-Type DNA Relevant to the Present Invention]

The mutant-type DNA relevant to the present invention is the one which has a substituted nucleotide, a deficient nucleotide region, or an inserted nucleotide region (hereinafter, these are sometimes referred collectively and simply to as a mutant nucleotide region), and any single-stranded DNA can be employed when at least anteroposterior 5 to 150 nucleotides of these mutant nucleotide region is known. It should be noted that, the mutant-type DNA relevant to the present invention includes the polymorphic DNA such as the single nucleotide substituted DNA and the DNA having different number of repeating nucleotide in the microsatellite region. Such DNA includes genomic DNA fragment isolated from living organisms such as animal, microorganism, bacteria and plant, DNA fragment which can be isolated from virus, and cDNA fragment synthesized using mRNA as a template. Among these mutant-type DNA, oncogene derived from human cell is included as a preferable one. In addition, the chain length of mutant-type DNA which forms the hybrid is usually 20 to 2000 nucleotides, preferably 100 to 500 nucleotides.

With respect to the above-described mutant nucleotide region, the substituted nucleotide represents, in the case that the mutation is substitution mutation, a substituted nucleotide in which the normal nucleotide in the wild-type DNA is substituted by mutation; the deficient nucleotide region represents, in the case that the mutation is deletion mutation, the nucleotide moiety in which the normal nucleotide in the wild-type DNA is deficient by mutation; and the inserted nucleotide region represents, in the case that the mutation is insertion mutation, the nucleotide moiety which is inserted into the wild-type DNA by mutation. It should be noted that, the above-described deficient nucleotide region and inserted nucleotide region are usually 1 to 200 nucleotides. In addition, since the probe which hybridizes with both mutant-type DNA and wild-type DNA relevant to the present invention may form a loop structure relevant to the present invention by using a specific mutant nucleotide region as a detection target, substituted nucleotide, deficient nucleotide region or inserted nucleotide region may exist other than the mutant nucleotide region which is used as a detection target.

The wild-type DNA relevant to the present invention is the one in which the nucleotide sequence except the mutant nucleotide region is identical to the mutant-type DNA relevant to the present invention, and its length is same level with the mutant-type DNA, and usually it is 20 to 2000 nucleotides, preferably 100 to 500 nucleotides.

Figure 1A:
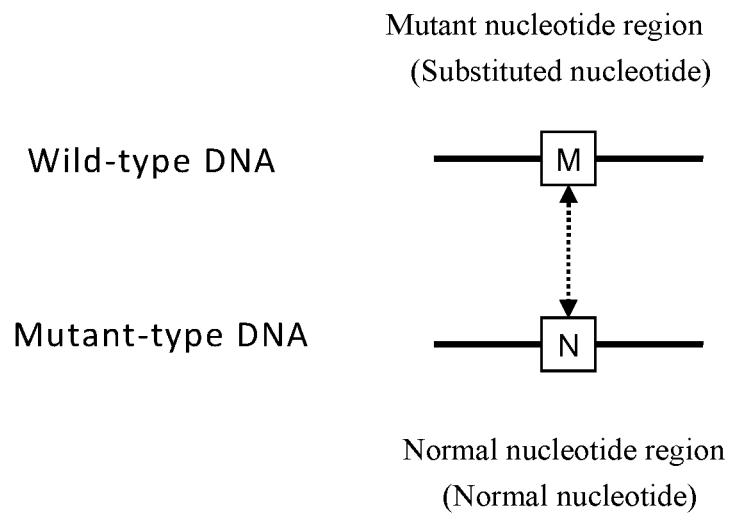
FIG. 1A illustrates a substitution mutation.
Figure 1B:
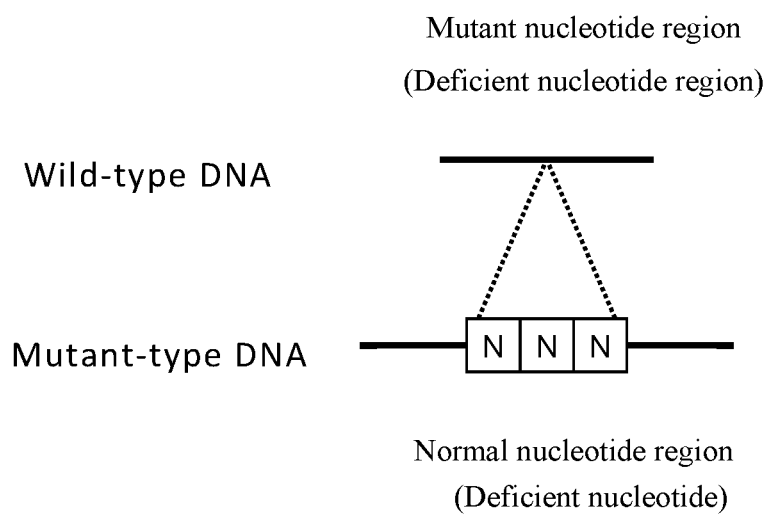
FIG. 1B illustrates a deletion mutation.
Figure 1C:
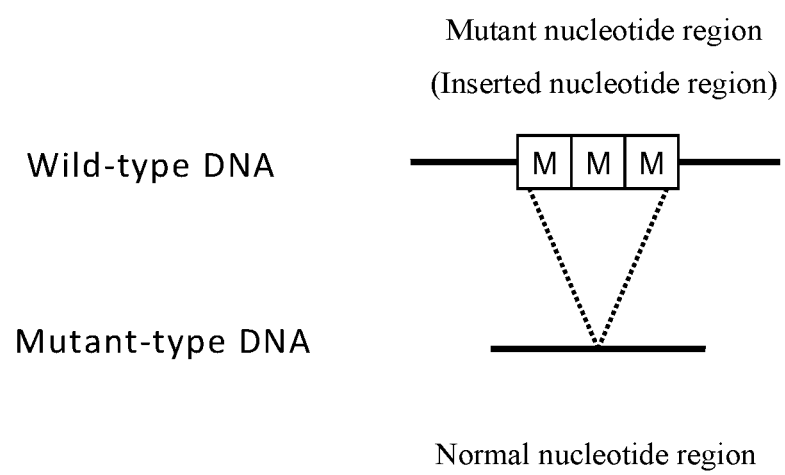
FIG. 1C illustrates an insertion mutation.

The normal nucleotide moiety of the wild-type DNA corresponding to the mutation moiety of the above-described mutant-type DNA is referred to as a normal nucleotide region. In the case that the mutation is substitution mutation, the normal nucleotide (nucleotide before mutation) of the wild-type DNA to the substituted nucleotide substituted by mutation is the normal nucleotide region (normal nucleotide); in the case that the mutation is deletion mutation, the normal nucleotide moiety (nucleotide moiety to be deleted by mutation) of the wild-type DNA to the nucleotide moiety deleted by mutation is the normal nucleotide region; in the case that the mutation is insertion mutation, the normal nucleotide moiety of the wild-type DNA to the nucleotide moiety inserted by mutation is the normal nucleotide region. Schematic diagram about the mutant nucleotide region and the normal nucleotide region is shown in FIGS. 1A, 1B, and 1C.

As for the above-described mutant-type DNA and the wild-type DNA relevant to the present invention (hereinafter, sometimes, these are collectively abbreviated as the DNA relevant to the present invention), it is preferable that the above-described DNA is purified as much as possible and unwanted substances other than nucleic acid fragment are removed. Specifically, for example, the one which was purified in accordance with a conventional method such as Boom method employing silica carrier (Boom et al., J. Clin. Microbiol. 28:495-503 (1990)), a method using sodium iodide solution (Proc. Natl. Acad. Sci. USA 76-2, p 615-619 (1979)) is preferable. In addition, the one which amplified an objective DNA by polymerase chain reaction (PCR reaction) well known per se, for example, by a method described in Nucleic Acids Research, 1991, Vol. 19, 3749, BioTechniques, 1994, Vol. 16, 1134-1137, may be employed.

In the case that the DNA relevant to the present invention forms a double-strand, the DNA relevant to the present invention may be obtained by converting the double-stranded DNA into single strand by means of heat treatment (90 to 100° C.) or alkaline treatment (treatment with sodium hydroxide, etc.), and the like, usually carried out in this field.

[Probe Relevant to the Present Invention]

The probe relevant to the present invention is the one which hybridizes with the mutant-type DNA relevant to the present invention and its corresponding wild-type DNA relevant to the present invention to form a mutant-type hybrid and a wild-type hybrid respectively, and at least one of the formed mutant-type hybrid or the wild-type hybrid forms a loop structure. In addition, even in the case that plural number of the formed hybrid form the loop structure, those loop structures is different structure. It should be noted that, in the case that the probe relevant to the present invention is consisted of a nucleotide sequence which is perfectly complementary to the mutant-type DNA or wild-type DNA, the obtained hybrid does not form the loop structure. Such probe relevant to the present invention is usually 10 to 2000 nucleotides, preferably 10 to 300 nucleotides, more preferably 10 to 150 nucleotides. It should be noted that, in the case that the loop structure is intended to be formed in the probe side, since its nucleotide sequence can be prepared arbitrarily, it is preferable to form the probe so as not to include the sequence complementary to the DNA relevant to the present invention so that, at forming the hybrid, the sequence which forms the loop structure does not bind with the DNA relevant to the present invention.

Figure 2A:
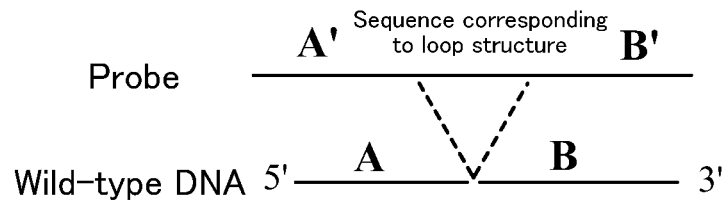
FIG. 2A depicts a mutant-type hybrid.
Figure 2A:
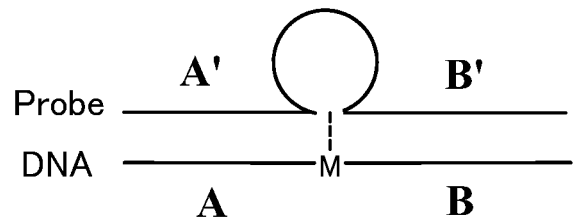
Figure 2B:
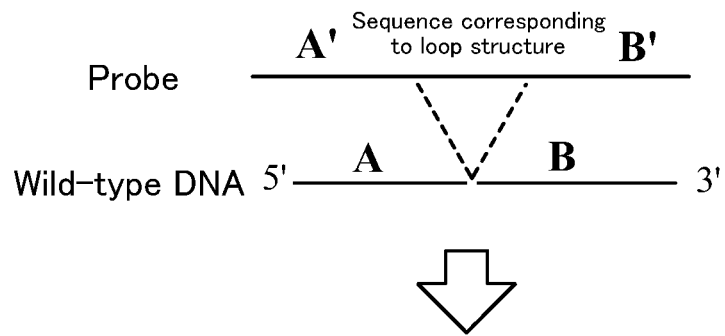
FIG. 2B represents a wild-type hybrid. M represents a substituted nucleotide, N represents a normal nucleotide corresponding to the substituted nucleotide, and A' moiety and B' moiety represent nucleotide regions complementary to the A moiety and B moiety, respectively.
Figure 2B:
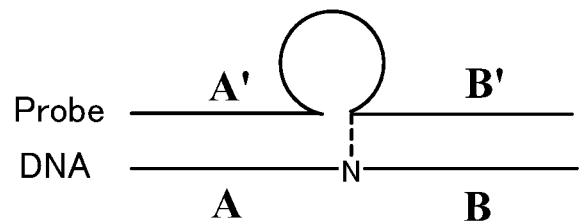

Although a specific example of the probe relevant to the present invention is described later together with a specific example of the hybrid, for example, in the case that the DNA to be detected is a mutant-type DNA having a substituted nucleotide, and the loop structure is intended to be formed in the probe side, the probe may be designed, for example, as the scheme described in FIGS. 2A and 2B. In FIGS. 2A and 2B, DNA is divided into A moiety and B moiety with centering on the normal nucleotide corresponding to the wild-type DNA substituted nucleotide, and the probe is designed so that a sequence, which is capable of forming the loop structure, is inserted in between chains complementary to A moiety and B moiety (A' and B'). It should be noted that M in the scheme represents a substituted nucleotide; N represents a normal nucleotide corresponding to the substituted nucleotide. In addition, A' moiety and B' moiety represent nucleotide regions complementary to the A moiety and B moiety, respectively.

By designing in this way, for example, in the case that the wild-type hybrid is formed, the loop structure as designed is formed, while, in the mutant-type hybrid, since the substituted nucleotide and a nucleotide in the probe which is complementary to the normal nucleotide do not bind, it is considered that the loop structure comprising one nucleotide complementary to the normal nucleotide is formed, in consequence, it becomes different from wild-type loop structure.

[Hybrid Relevant to the Present Invention]

The hybrid relevant to the present invention is formed by hybridizing the above-described probe relevant to the present invention with the wild-type DNA or the mutant-type DNA relevant to the present invention, and either one of them has a loop structure. In addition, if more than one of the wild-type hybrid and the mutant hybrid have loop structure, the loop structures are different. That is, even if these are wild-type hybrid and mutant-type hybrid or both mutant-type hybrids, each loop structure is different. Therefore, in the detection method of the present invention, it is possible to separate this difference in the structure and the difference caused by binding the intercalator to double-stranded nucleotide moiety, with high accuracy.

The hybrid relevant to the present invention having a loop structure is composed of two double-stranded nucleotide moieties and a loop structure of single-stranded nucleotide moiety sandwiched between them (located between them). It should be noted that said hybrid may have a protruding end, however, because of having possibilities of affecting the separation performance, the one which has no protruding end is preferable. In addition, in the place sandwiched by two double-stranded nucleotide moieties, the chain in the opposite side of the nucleotide chain which has loop structure may have a single-stranded nucleotide moiety which is not complementary to the loop structure. In addition, said hybrid may be formed so as to have loop structure on the both side of the hybrid by forming another additional loop structure on the other side of the nucleotide sequence having loop structure. Further, in the case that the probe to be used is a nucleotide sequence complementary to the nucleotide sequence of one of wild-type DNA or mutant-type DNA (a nucleotide sequence which matches 100% with entire or a part of the nucleotide sequence of one of the wild-type DNA or mutant-type DNA), because the hybrid to be formed has no loop structure, the hybrid is a hybrid having only double-stranded nucleotide or a hybrid having double-stranded nucleotide and a protruding end.

The loop structure in the above-described hybrid relevant to the present invention is composed of a single-stranded nucleotide chain which does not hybridize (does not form base pair) with the probe or genomic DNA, and forms secondary structure (steric structure) of a loop in the hybrid. Said loop structure is composed of usually 3 to 300 nucleotides, preferably 5 to 100 nucleotides.

Figure 3:
FIG. 3 are diagrams of loop structures having a stem. A solid line represents the stem structure; a dotted line represents a double-stranded nucleotide chain which is formed by genomic DNA and the probe.
Figure 4A:
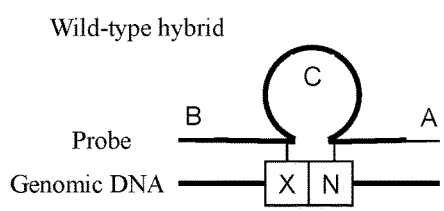
FIGS. 4A-4B depict a wild-type hybrid and FIGS. 4C-4D represent a mutant-type hybrid. N represents a normal nucleotide, M represents a substituted nucleotide, X represents a nucleotide (nucleotide next to 5' terminal side or 3' terminal side) next to the normal nucleotide or the substituted nucleotide, and X' represents a nucleotide (a nucleotide adjacent in the direction opposite to X) next to the substituted nucleotide.
Figure 4B:
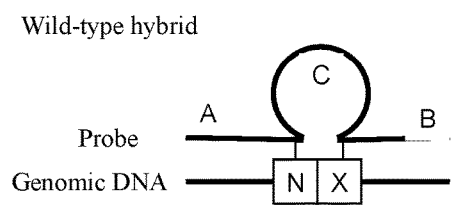
Figure 4C:
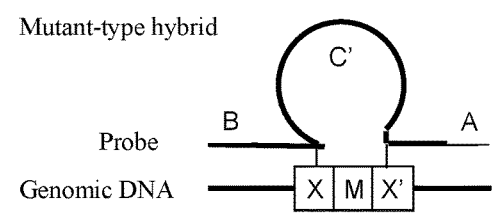
Figure 4D:
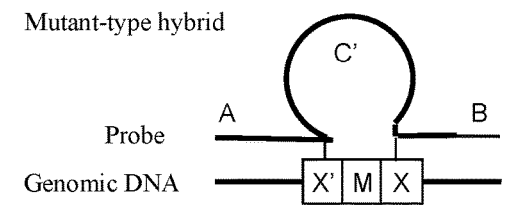
Figure 5A:
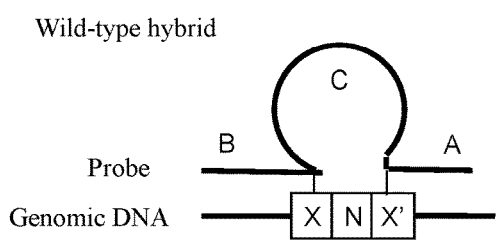
FIGS. 5A-5B depict a wild-type hybrid.
Figure 5B:
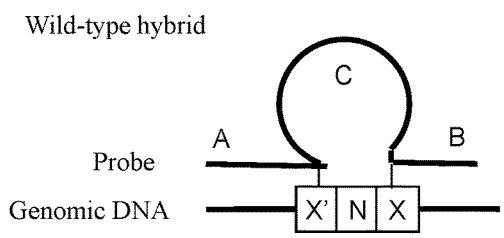
Figure 5C:
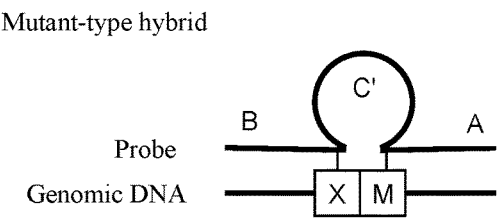
FIGS. 5C-5D represent a mutant-type hybrid. N represents a normal nucleotide, M represents a substituted nucleotide, X represents a nucleotide (nucleotide next to 5' terminal side or 3' terminal side) next to the normal nucleotide or the substituted nucleotide, and X' represents a nucleotide (a nucleotide adjacent in the direction opposite to X) next to the substituted nucleotide.
Figure 5D:
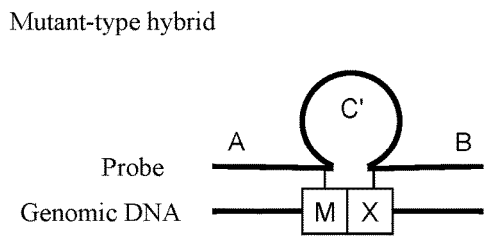
Figure 6A:
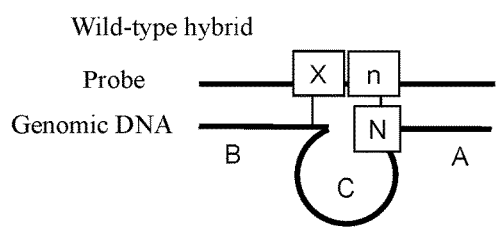
FIGS. 6A-6B depict a wild-type hybrid.
Figure 6B:
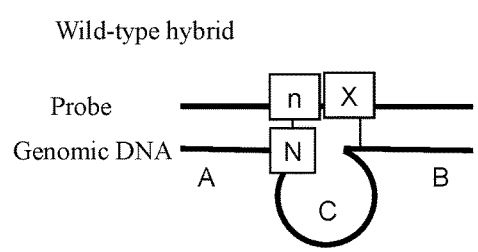
Figure 6C:
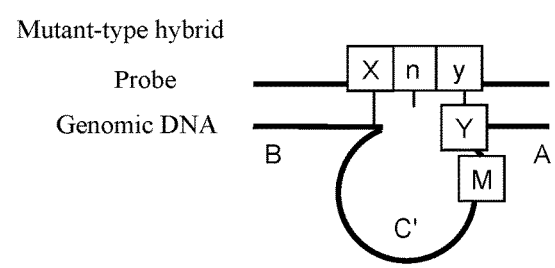
FIGS. 6C-6D represents a mutant-type hybrid. N represents a normal nucleotide, M represents a substituted nucleotide, X represents a nucleotide next to a nucleotide (n) complementary to N.
Figure 6D:
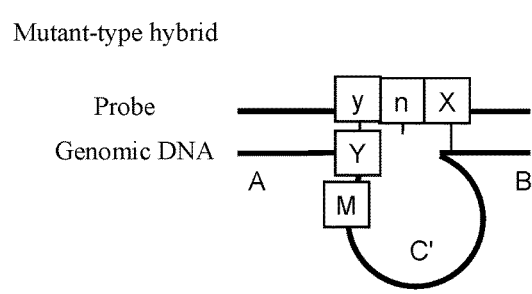
Figure 7A:
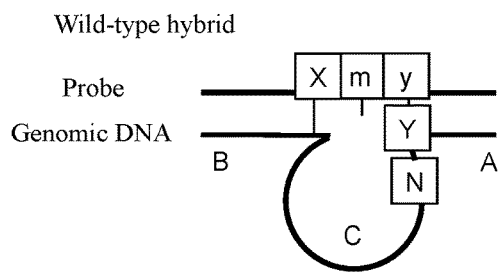
FIGS. 7A-7B depict a wild-type hybrid.
Figure 7C:
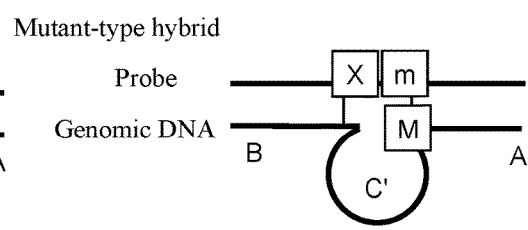
FIGS. 7C-7D represent a mutant-type hybrid. N represents a normal nucleotide, M represents a substituted nucleotide, X represents a nucleotide next to a nucleotide (m) complementary to M.
Figure 7B:
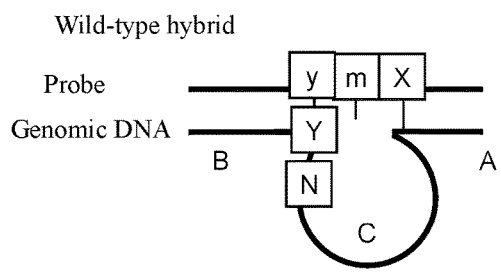
Figure 7D:
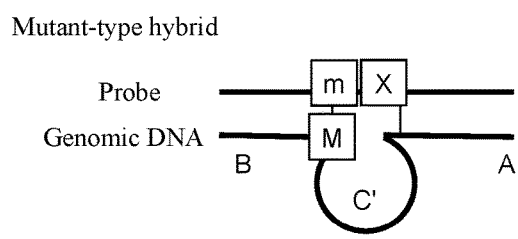

The loop structure relevant to the present invention may have a stem. Said stem represents a structure in which the above-described single-stranded nucleotide chain forms double-stranded chain by itself (double-stranded nucleotide or double-stranded nucleotide chain moiety). Said stem is a one which is at least one or more consecutive base pairs, preferably 2 or more consecutive base pairs, more preferably 3 or more consecutive base pairs. The loop structure relevant to the present invention may be the one which is composed only of the stem. That is, the loop structure having the stem includes the one which is composed only of the stem, the one which comprises the stem located at the end of the loop structure, the one which comprises the stem located at front edge of the loop structure, the one which comprises the stem located at intermediate position in the loop structure, and combination thereof. Schematic diagrams of the loop structure having the stem is shown in FIG. 3. It should be noted that, a solid line represents the stem structure; a dotted line represents a double-stranded nucleotide chain which is formed by genomic DNA and the probe.

In addition, as for the parallel moiety in the loop structure, in respect of separation performance, the one in which the loop structure has the above-described stem is preferable.

The double-stranded nucleotide moiety of two places in the above-described hybrid are each independently composed of usually 5 to 1000 base pairs, preferably 10 to 500 base pairs, and more preferably 10 to 100 base pairs.

In the case that the loop structure is formed on both genomic DNA side and probe side of the hybrid, when one loop structure is located in the place capable of identifying mutant nucleotide (the place located in the mutant nucleotide region), other loop structure may be located in any place. Said loop structure is composed of usually 3 to 300 nucleotides, preferably 5 to 100 nucleotides.

As for the hybrid having loop structure on both side of the above-described hybrid, when either one of the loop structures is set so as to recognize (so as to be located in the mutant nucleotide region) mutant nucleotide (region), other loop structure may be formed in any place and at any size.

The above-described probe as well as the above-described hybrid may be designed appropriately and synthesized depending on the type of mutant-type DNA (the single-stranded DNA having the above-described substituted nucleotide, deficient nucleotide region, or inserted nucleotide region), or depending on whether it hybridizes with the mutant nucleotide region or a normal nucleotide or a normal nucleotide region corresponding to the mutant nucleotide region. As for the specific example of the probe, it is described by dividing into cases as follows, respectively. It should be noted that, in the case that DNA having a microsatellite region is separated, a probe and a hybrid as described, for example, in JP-A-2012-65232 may be employed.

(I) In the case that the mutant-type DNA is a DNA having a substituted nucleotide
   (I-1) In the case that a hybrid having a loop structure at the probe side is intended to be formed
   (I-2) In the case that a hybrid having a loop structure at the genomic DNA side is intended to be formed
(II) In the case that the mutant-type DNA is a DNA having a deficient nucleotide region
   (II-1) In the case that a hybrid having a loop structure at the probe side is intended to be formed
   (II-2) In the case that a hybrid having a loop structure at the genomic DNA side is intended to be formed
(III) In the case that the mutant-type DNA is a DNA having a inserted nucleotide region
   (III-1) In the case that a hybrid having a loop structure at the probe DNA side is intended to be formed
   (III-2) In the case that a hybrid having a loop structure at the genomic side is intended to be formed
(IV) In the case that a loop structure is further formed in the chain of opposite sides of the nucleotide chain having a loop structure
[Specific Example of Probe and Hybrid Relevant to the Present Invention]
(I) In the Case that the Mutant-Type DNA is a DNA Having a Substituted Nucleotide
   (I-1) In the Case that the Hybrid Having a Loop Structure at the Probe Side is Intended to be Formed As for the probe relevant to the present invention in the present case, the probe shown in FIGS. 4A-4D may be employed. When the probe hybridizes with wild-type genomic DNA, it forms a wild-type hybrid, which has (1) a double-stranded nucleotide moiety extending from a normal nucleotide (N) of the wild-type genomic DNA toward one end (A direction), and a double-stranded nucleotide moiety extending from a nucleotide (X) next to 1 to 10 nucleotides in the direction (B direction) opposite to A direction from said normal nucleotide (N) toward the same B direction, and also has (2) a loop structure (C) of a single-stranded nucleotide moiety at the probe side between a nucleotide complementary to the normal nucleotide (N) and a nucleotide complementary to the nucleotide (X) next to 1 to 10 nucleotides from the nucleotide complementary to the normal nucleotide (N); whereas, when the probe hybridizes with mutant-type genomic DNA, it forms a mutant-type hybrid, which has (1) a double-stranded nucleotide moiety extending from a nucleotide next to said substituted nucleotide (M) toward one end (A direction) without forming base pair with the substituted nucleotide (M) of the mutant-type genomic DNA, and a double-stranded nucleotide moiety extending in the direction opposite to A direction (B direction) from nucleotide (X) next to 1 to 10 nucleotides in the direction opposite to A direction (B direction) from the substituted nucleotide (M) toward the same B direction, and also has (2) a loop structure (C') of a single-stranded nucleotide moiety on the probe side between a nucleotide complementary to the nucleotide (X') adjacent in the direction toward A to the substituted nucleotide (M) and a nucleotide (X) complementary to the nucleotide next to 1 to 10 nucleotides in the B direction. In this case, although the loop structures (C, C') are formed on both wild-type hybrid and mutant-type hybrid, since the probe does not bind to the substituted nucleotide (M), the loop structure (C') in the mutant-type hybrid is longer than that (C) of wild-type hybrid by one nucleotide. It should be noted that, in the case that the above-described nucleotide (X) next to 1 to 10 nucleotides is a nucleotide next to 2 to 10 nucleotides, the hybrid have a single-stranded nucleotide moiety in the genomic DNA side between two double-stranded nucleotides, namely, in the opposite side of the loop structure, which is not complementary to the loop structure. A schematic diagram of the hybrid in the case that the above-described nucleotide (X) next to 1 to 10 nucleotides is a nucleotide next to 1 nucleotide, is described in FIGS. 4A-4D. It should be noted that, N represents a normal nucleotide, M represents a substituted nucleotide, X represents a nucleotide (nucleotide next to 5' terminal side or 3' terminal side) next to the normal nucleotide or the substituted nucleotide, and X' represents a nucleotide (a nucleotide adjacent in the direction opposite to X) next to the substituted nucleotide.

Such probe includes, specifically, the one in which a complementary strand of a nucleotide sequence of usually 5 to 1000 nucleotides, preferably 5 to 150 nucleotides from a normal nucleotide in the direction toward 5' terminal in the wild-type DNA, a nucleotide sequence of usually 3 to 300 nucleotides, preferably 5 to 100 nucleotides which forms a loop structure, and a complementary strand of a nucleotide sequence of usually 5 to 1000 nucleotides, preferably 5 to 150 nucleotides in the direction toward 3' terminal from the nucleotide next to 1 to 10 nucleotides in the direction toward 3' terminal from the normal nucleotide in the wild-type DNA are bound in this order, or the one in which a complementary strand of a nucleotide sequence of usually 5 to 1000 nucleotides, preferably 5 to 150 nucleotides from a normal nucleotide in the direction toward 3' terminal in the wild-type DNA, a nucleotide sequence of usually 3 to 300 nucleotides, preferably 5 to 100 nucleotides which forms a loop structure, and a complementary strand of a nucleotide sequence of usually 5 to 1000 nucleotides, preferably 5 to 150 nucleotides in the direction toward 5' terminal from the nucleotide next to 1 to 10 nucleotides in the direction toward 5' terminal from the normal nucleotide in the wild-type DNA are bound in this order, and the like.

In addition, as for the probe relevant to the present invention in the present case, the probe of FIGS. 5A-5D may be employed. When the probe hybridizes with mutant-type genomic DNA, it forms a mutant-type hybrid which has (1) a double-stranded nucleotide moiety extending from a substituted nucleotide (M) of the mutant-type genomic DNA toward one end (A direction), and a double-stranded nucleotide moiety extending from a nucleotide (X) next to 1 to 10 nucleotides in the direction opposite to A direction (B direction) from said substituted nucleotide (M) toward the same B direction, and also has (2) a loop structure (C') of a single-stranded nucleotide moiety in the probe side between a nucleotide complementary to the substituted nucleotide (M) and a nucleotide complementary to the nucleotide (X) next to 1 to 10 nucleotides from the nucleotide complementary to the said substituted nucleotide (M); whereas, when the probe hybridizes with wild-type genomic DNA, it forms a normal-type hybrid which has (1) a double-stranded nucleotide moiety extending from a nucleotide (X') next to the normal nucleotide toward one end (A direction) without forming base pair with the normal nucleotide of wild-type genomic DNA, and a double-stranded nucleotide moiety extending in the direction opposite to A direction (B direction) from nucleotide (X) next to 1 to 10 nucleotides from the normal nucleotide (N) toward the same B direction, and also has (2) a loop structure (C) of a single-stranded nucleotide moiety in the probe side between a nucleotide complementary to the nucleotide (X') adjacent in the direction toward A to the normal nucleotide (N) and a nucleotide complementary to the nucleotide (X) next to 1 to 10 nucleotides in the B direction. In this case, although the loop structures (C, C') are formed in both wild-type hybrid and mutant-type hybrid, the loop structure (C) in the wild-type hybrid is longer than that (C') of mutant-type hybrid by one nucleotide. It should be noted that, in the case that the above-described nucleotide (X) next to 1 to 10 nucleotides is a nucleotide next to 2 to 10 nucleotides, the hybrid is to have a single-stranded nucleotide moiety between 2 double-stranded nucleotides in the genomic DNA side, namely, in the opposite side of the loop structure, which is not complementary to the loop structure. A schematic diagram of the hybrid in the case that the above-described nucleotide (X) next to 1 to 10 nucleotides is a nucleotide next to 1 nucleotide is described in FIGS. 5A-5D. In addition, N represents a normal nucleotide, M represents a substituted nucleotide, X represents a nucleotide (a nucleotide next to 5' terminal side or 3' terminal side) next to the normal nucleotide or the substituted nucleotide, and X' represents a nucleotide (a nucleotide adjacent in the direction opposite to X) next to the normal nucleotide.

Such probe includes, specifically, the one in which a complementary strand of a nucleotide sequence of usually 5 to 1000 nucleotides, preferably 5 to 150 nucleotides from a substituted nucleotide of the mutant-type DNA in the direction toward 5' terminal, a nucleotide sequence of usually 3 to 300 nucleotides, preferably 5 to 100 nucleotides which forms a loop structure, and a complementary strand of a nucleotide sequence of usually 5 to 1000 nucleotides, preferably 5 to 150 nucleotides in the direction toward 3' terminal from the nucleotide next to 1 to 10 nucleotides in the direction toward 3' terminal from the substituted nucleotide in the mutant-type DNA are bound in this order, or the one in which a complementary strand of a nucleotide sequence of usually 5 to 1000 nucleotides, preferably 5 to 150 nucleotides from a substituted nucleotide of the mutant-type DNA in the direction toward 3' terminal, a nucleotide sequence of usually 3 to 300 nucleotides, preferably 5 to 100 nucleotides which forms a loop structure, and a complementary strand of a nucleotide sequence of usually 5 to 1000 nucleotides, preferably 5 to 150 nucleotides in the direction toward 5' terminal from the nucleotide next to 1 to 10 nucleotides in the direction toward 5' terminal from the substituted nucleotide in the mutant-type DNA are bound in this order, and the like.

(I-2) In the Case that the Hybrid Having a Loop Structure in the Genomic DNA Side is Intended to be Formed As for the probe relevant to the present invention in the present case, the probe of FIGS. 6A-6D may be employed. When the probe hybridizes with wild-type genomic DNA, it forms a wild-type hybrid which has a double-stranded nucleotide moiety extending from a normal nucleotide (N) of the wild-type genomic DNA toward one end (A direction), and a double-stranded nucleotide moiety including a nucleotide (X) next to a nucleotide (n) complementary to said normal nucleotide (N) in the direction opposite to A direction (B direction), and also has a loop structure (C) of a single-stranded nucleotide moiety having a nucleotide next to the normal nucleotide (N) as a terminal on the genomic DNA; whereas, when the probe hybridizes with mutant-type genomic DNA, it forms a mutant-type hybrid which has a double-stranded nucleotide moiety extending from a nucleotide (Y) next to said substituted nucleotide (M) toward one end (A direction) without forming base pair with the substituted nucleotide (M) of the mutant-type genomic DNA, and a double-stranded nucleotide moiety extending in the direction opposite to A direction (B direction) from nucleotide (X) next to 2 nucleotides toward the B direction from a nucleotide (y) complementary to the nucleotide (Y) next to the above-described substituted nucleotide, and has a loop structure (C') of a single-stranded nucleotide moiety having the substituted nucleotide (M) as a terminal on the genomic DNA, may be used. In this case, although the loop structures (C, C') are formed on both wild-type hybrid and mutant-type hybrid, since the probe does not bind with the substituted nucleotide (M), the loop structure (C') in the mutant-type hybrid is longer than that (C) of wild-type hybrid by one nucleotide. Its schematic diagram is described in FIGS. 6A-6D. In addition, N represents a normal nucleotide and M represents a substituted nucleotide, respectively.

Such probe includes, specifically, the one in which a complementary strand of a nucleotide sequence of usually 5 to 1000 nucleotides, preferably 5 to 150 nucleotides from a normal nucleotide of the wild-type DNA in the direction toward 5' terminal, and a complementary strand of a nucleotide sequence of usually 5 to 1000 nucleotides, preferably 5 to 150 nucleotides in the direction toward 3' terminal from a nucleotide next to 4 to 300 nucleotides, preferably 6 to 100 nucleotides in the direction toward 3' terminal from the normal nucleotide in the wild-type DNA are bound in this order, or the one in which a complementary strand of a nucleotide sequence of usually 5 to 1000 nucleotides, preferably 5 to 150 nucleotides from a normal nucleotide of the wild-type DNA in the direction toward 3' terminal, and a complementary strand of a nucleotide sequence of usually 5 to 1000 nucleotides, preferably 5 to 150 nucleotides in the direction toward 5' terminal from the nucleotide next to 4 to 300 nucleotides, preferably 6 to 100 nucleotides in the direction toward 5' terminal from the normal nucleotide in the wild-type DNA are bound in this order, and the like.

In addition, as for the probe relevant to the present invention in the present case, the probe shown in FIGS. 7A-7D may be employed. When the probe hybridizes with wild-type genomic DNA, it forms a wild-type hybrid, which has a double-stranded nucleotide moiety extending from a nucleotide (Y) next to said normal nucleotide (N) toward one end (A direction), and a double-stranded nucleotide moiety including a nucleotide (X) next to 2 nucleotides in the direction opposite to A direction (B direction) from a complementary nucleotide (y) of the nucleotide (Y) next to the above-described normal nucleotide (N), without forming base pair with the normal nucleotide (N) of the wild-type genomic DNA, and also has a loop structure (C) of a single-stranded nucleotide moiety having the normal nucleotide (N) as a terminal on the genomic DNA; whereas, when the probe hybridizes with mutant-type genomic DNA, it forms a mutant-type hybrid which has a double-stranded nucleotide moiety extending from a substituted nucleotide (M) of mutant-type genomic DNA toward one end (A direction), and a double-stranded nucleotide moiety extending in the direction opposite to A direction (B direction) from nucleotide (X) next to a complementary nucleotide (m) of said substituted nucleotide, and also has a loop structure (C') of a single-stranded nucleotide moiety having a nucleotide next to the substituted nucleotide as a terminal on the genomic DNA. In this case, although the loop structure (C, C') is formed in both wild-type hybrid and mutant-type hybrid, since the probe does not bind with normal nucleotide, the loop structure (C) in the wild-type hybrid is longer than that (C') of mutant-type hybrid by one nucleotide. Its schematic diagram is described in FIGS. 7A-7D. In addition, N represents a normal nucleotide and M represents a substituted nucleotide, respectively.

Such probe includes, specifically, the one in which a complementary strand of a nucleotide sequence of usually 5 to 1000 nucleotides, preferably 5 to 150 nucleotides from a normal nucleotide in the wild-type DNA in the direction toward 5' terminal, and a complementary strand of a nucleotide sequence of usually 5 to 1000 nucleotides, preferably 5 to 150 nucleotides in the direction toward 3' terminal from a nucleotide next to 4 to 300 nucleotides, preferably 6 to 100 nucleotides in the direction toward 3' terminal from the normal nucleotide in the wild-type DNA are bound in this order, or the one in which a complementary strand of a nucleotide sequence of usually 5 to 1000 nucleotides, preferably 5 to 150 nucleotides from a normal nucleotide in the wild-type DNA in the direction toward 3' terminal, and a complementary strand of a nucleotide sequence of usually 5 to 1000 nucleotides, preferably 5 to 150 nucleotides in the direction toward 5' terminal from the nucleotide next to usually 4 to 300 nucleotides, preferably 6 to 100 nucleotides in the direction toward 5' terminal from the normal nucleotide in the wild-type DNA are bound in this order, and the like.

(II) In the Case that the Mutant-Type DNA is a DNA Having a Deficient Nucleotide Region (II-1) In the Case that the Hybrid Having a Loop Structure in the Probe Side is Intended to be Formed As for the probe relevant to the present invention in the present case, (a) a probe which forms a wild-type hybrid not having a loop structure and forms a mutant-type hybrid having a loop structure, or (b) a probe which forms a wild-type hybrid having a loop structure on the probe and forms a mutant-type hybrid having a loop structure on the probe, but the loop structures of the two are different, may be used.

Figure 8A:
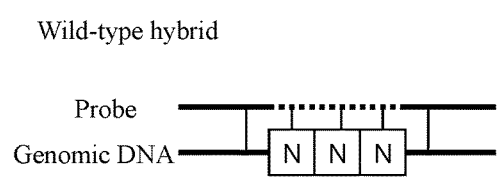
FIG. 8 illustrates an embodiment in which a probe forms a wild-type hybrid not having a loop structure (FIG. 8A) and a mutant-type hybrid having a loop structure (FIG. 8B). NNN represents a normal nucleotide region, and a dotted line represents a complementary strand of the normal nucleotide region.
Figure 8B:
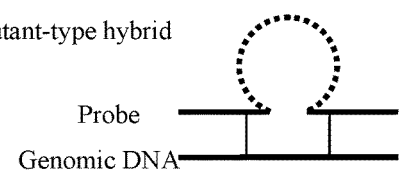
Figure 9A:
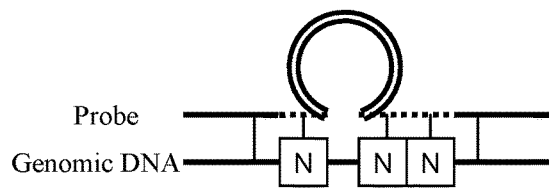
FIGS. 9A-9C depict wild-type hybrids.
Figure 9D:
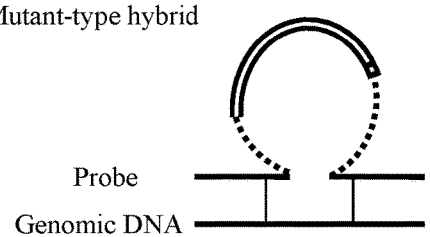
FIGS. 9D-9F depict mutant-type hybrids. NNN represents a normal nucleotide region; a dotted line represents a complementary strand of the normal nucleotide region; and a double line represents a nucleotide chain optionally inserted in the probe.
Figure 9B:
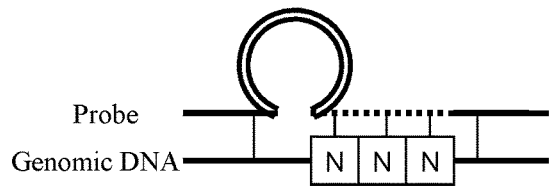
Figure 9E:
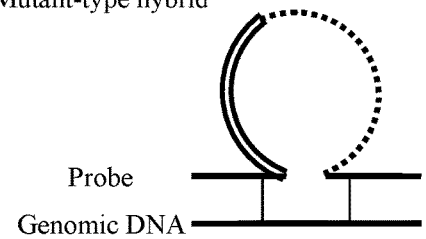
Figure 9C:
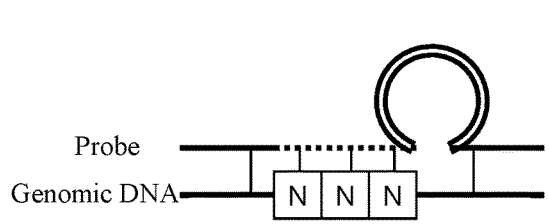
Figure 9F:
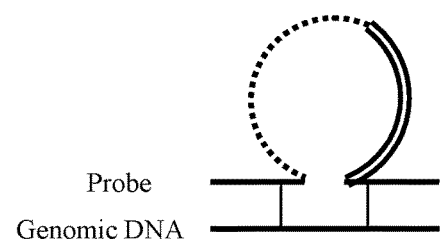

As for the probe of the above-described (a), a probe, which is consisted of a nucleotide sequence complementary to an entire nucleotide sequence of the wild-type DNA or a nucleotide sequence complementary to a part of nucleotide sequence including normal nucleotide of the wild-type DNA (a nucleotide sequence which is 100% complementary to an entire or a part of the nucleotide sequence), may be used. When such probe is used, the wild-type hybrid become the one not forming the loop structure and the mutant-type hybrid forms a loop structure of a nucleotide sequence complementary to the deficient nucleotide region, on the probe. Its schematic diagram is described in FIGS. 8A and 8B. It should be noted that, in FIG. 8, NNN represents a normal nucleotide region, a dotted line represents a complementary strand of the normal nucleotide region, respectively.

Such probe includes, specifically, a complementary strand of a nucleotide sequence which is made by binding the deficient nucleotide region and each 5 to 1000 nucleotides, preferably 5 to 150 nucleotides on its both sides, and the like. In other words, a nucleotide sequence which is complementary to the wild-type DNA, and which is complementary to a sequence consisted of a deficient nucleotide region and each 5 to 1000 nucleotides, preferably 5 to 150 nucleotides on its both sides, is included.

As for the probe of the above-described (b), a probe in which a nucleotide sequence which does not hybridize with wild-type DNA nor with mutant-type DNA is inserted into a nucleotide sequence complementary to the normal nucleotide region of the above described probe (a) or next to said nucleotide sequence, may be used. When such probe is used, in the wild-type hybrid, the above-described inserted nucleotide sequence which does not hybridize with wild-type DNA nor with mutant-type DNA forms a loop structure on the probe, and in the mutant-type hybrid, a nucleotide sequence complementary to the normal nucleotide region and the above-described inserted nucleotide sequence which does not hybridize with wild-type DNA nor with mutant-type DNA will jointly form a loop structure on the probe. That is, the loop structure of the wild-type hybrid and that of the mutant-type hybrid is different in structure. Its schematic diagram is described in FIGS. 9A-9F. It should be note that, in FIGS. 9A-9F, NNN represents a normal nucleotide region; a dotted line represents a complementary strand of the normal nucleotide region; and a double line represents a nucleotide chain optionally inserted in the probe, respectively.

Such probe includes, specifically, a complementary strand of a nucleotide sequence which is made by binding each 5 to 1000 nucleotides, preferably 5 to 150 nucleotides of its both sides with a normal nucleotide region in which usually 1 to 300 nucleotides, preferably 5 to 100 nucleotides is inserted into the normal nucleotide region of the wild-type DNA, or into either of optional position next to 3' terminal or a position next to 5' terminal of said normal nucleotide region. It should be noted that, in the case that the above-described nucleotide sequence to be inserted is 1 to 2 nucleotides, although the wild-type hybrid cannot form loop structure, this case also is included in the probe of (b). In addition, the above-described nucleotide sequence to be inserted may be subdivided and inserted into plural positions in the above-described place, as long as the total number of nucleotides is within the above-described range.

(II-2) In the Case that the Hybrid Having a Loop Structure in the Genomic DNA Side is Intended to be Formed As for the probe relevant to the present invention in the present case, (a) a probe which forms a mutant-type hybrid not having a loop structure and forms a wild-type hybrid having a loop structure, or (b) a probe which forms a mutant-type hybrid having a loop structure on the genome and forms a wild-type hybrid having a loop structure on the genome, but the loop structures of the two are different, may be used.

Figure 10A:
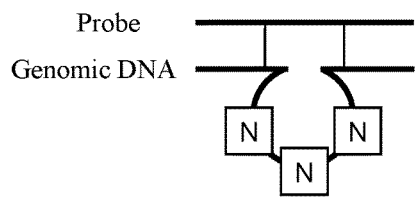
FIG. 10A depicts a wild-type hybrid and FIG. 10B depicts a mutant-type hybrid. N represents a normal nucleotide region.
Figure 10B:
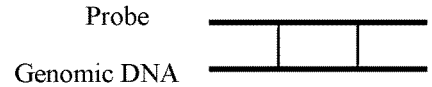
Figure 11A:
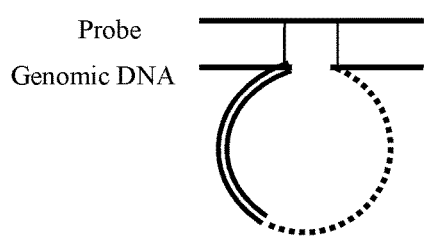
FIG. 11A depicts a wild-type hybrid.
Figure 11C:
FIG. 11 illustrates an embodiment in which a probe with a nucleotide sequence for constituting a loop in the mutant-type hybrid is excluded from the probe at a nucleotide complementary to a nucleotide next to a normal nucleotide region as a base point.
FIG. 11B depicts genomic DNA. A dotted line represents a normal nucleotide region corresponding to a deficient nucleotide region; and a double line represents a nucleotide chain deleted arbitrarily from a sequence complementary to the genomic DNA at setting the probe.
Figure 11B:
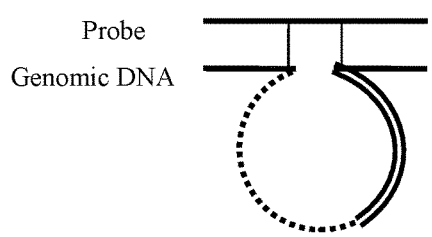
Figure 11D:

As for the probe of the above-described (a), a probe which is consisted of a nucleotide sequence complementary to an entire or a part of nucleotide sequence of the mutant-type DNA (a nucleotide sequence which is 100% complementary to an entire or a part of the nucleotide sequence), may be used. In other words, a probe which is consisted of a nucleotide sequence complementary to an entire of a nucleotide sequence other than the normal nucleotide region which is deleted by mutation in the wild-type DNA or a part of nucleotide sequence including nucleotide sequences on both sides of the normal nucleotide region, may be used. When such probe is used, in the wild-type hybrid, the normal nucleotide region forms a loop structure on its genomic DNA and, the mutant-type hybrid does not form a loop structure. Its schematic diagram is described in FIGS. 10A and 10B. In addition, in FIGS. 10A and 10B, N represents a normal nucleotide region.

Such probe includes, specifically, a complementary strand of a nucleotide sequence which is made by binding each 5 to 1000 nucleotides, preferably 5 to 150 nucleotides on both side of the deficient nucleotide region of mutant-type DNA. In other words, it is a sequence complementary to the mutant-type DNA, and is a nucleotide sequences complementary to the nucleotide sequences of each 5 to 1000 nucleotides, preferably 5 to 150 nucleotides in two directions from the place corresponding to the deficient nucleotide region is included.

As for the probe of the above-described (b), a probe in which the nucleotide sequence for constituting a loop in the mutant-type hybrid is excluded from a probe of above-described (a) at a nucleotide complementary to a nucleotide next to normal nucleotide region as a base point, may be used. When such probe is used, the wild-type hybrid forms the loop structure together with nucleotide sequence excluded in the above and the normal nucleotide region, on the genomic DNA, and in the mutant-type hybrid, the nucleotide sequence excluded in the above forms the loop structure. That is, the loop structure of the wild-type hybrid and that of the mutant-type hybrid is different in structure. Its schematic diagram is described in FIGS. 11A-11D. It should be noted that, in FIGS. 11A-11D, a dotted line represents a normal nucleotide region corresponding to a deficient nucleotide region; and a double line represents a nucleotide chain deleted arbitrarily from a sequence complementary to the genomic DNA at setting the probe.

Such probe includes, specifically, a complementary strand of a nucleotide sequence which is made by binding a nucleotide sequence of usually 5 to 1000 nucleotides, preferably 5 to 150 nucleotides from a nucleotide next to usually 1 to 300 nucleotides, preferably 5 to 100 nucleotides in the direction toward 3' side of the normal nucleotide region of the wild-type DNA and a nucleotide sequence of usually 5 to 1000 nucleotides, preferably 5 to 150 nucleotides from a nucleotide next to usually 1 to 300 nucleotides, preferably 5 to 100 nucleotides in the direction toward 5' side. In this regard, however, the complementary strand of a nucleotide sequence which is made by binding a nucleotide sequence from a nucleotide next to 1 nucleotide in the direction toward 3' side of the normal nucleotide region and a nucleotide sequence from a nucleotide next to 1 nucleotide in the direction toward 5' side is excluded (because it is a probe of the above-described (a)). In addition, in the nucleotide next to 1 to 300 nucleotides in the direction toward 3' side of the normal nucleotide region and the nucleotide next to 1 to 300 nucleotides in the direction toward 5' side, when a total number of these next nucleotides is 4 or less, the mutant-type hybrid cannot form loop structure, but this case is also included in the probe of the above-described (b). In addition, the above-described total number of next nucleotides is usually 1 to 300 nucleotides, preferably 5 to 100 nucleotides.

(III) In the Case that the Mutant-Type DNA is a DNA Having a Inserted Nucleotide Region (III-1) In the Case that the Hybrid Having a Loop Structure in the Probe DNA Side is Intended to be Formed As for the probe relevant to the present invention in the present case, (a) a probe which forms a wild-type hybrid having a loop structure and forms a mutant-type hybrid not having a loop structure, or (b) a probe which forms a wild-type hybrid having a loop structure on the probe and forms a mutant-type hybrid having a loop structure on the probe, but both loop structures are different, may be used.

Figure 12A:
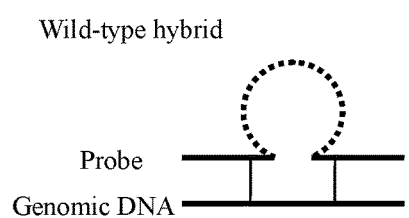
FIG. 12A is a wild-type hybrid.
Figure 12B:
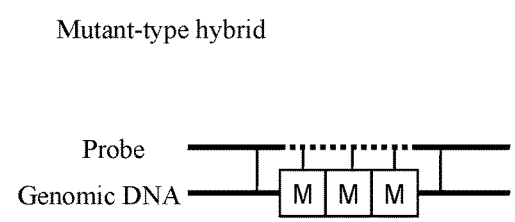
FIG. 12B is a mutant-type hybrid. MMM represents an inserted nucleotide region, and a dotted line represents a complementary strand of the inserted nucleotide region.
Figure 13A:
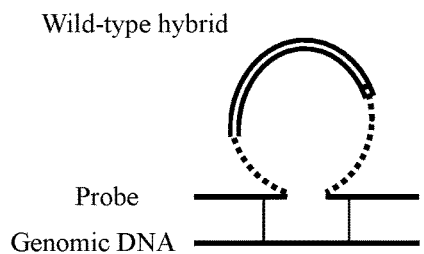
FIGS. 13A-13C depict a wild-type hybrid.
Figure 13D:
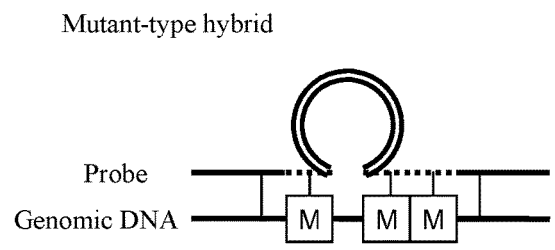
FIGS. 13D-13F depict mutant-type hybrid. MMM represents a inserted nucleotide region, a dotted line represents a complementary strand of the inserted nucleotide region, and a double line represents a nucleotide chain optionally inserted in the probe.
Figure 13B:
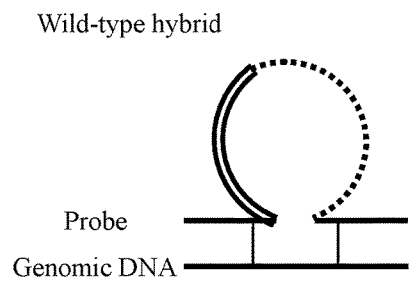
Figure 13E:
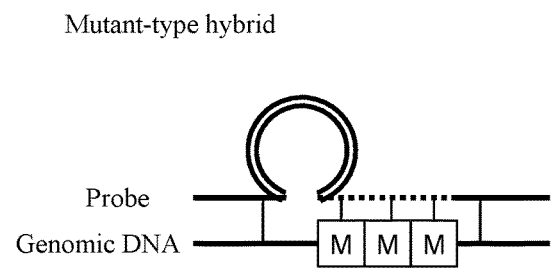
Figure 13C:
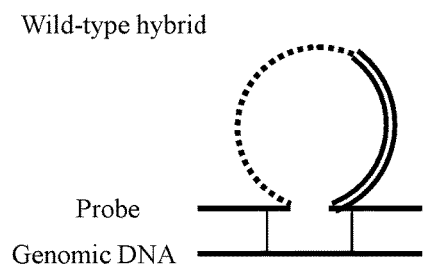
Figure 13F:
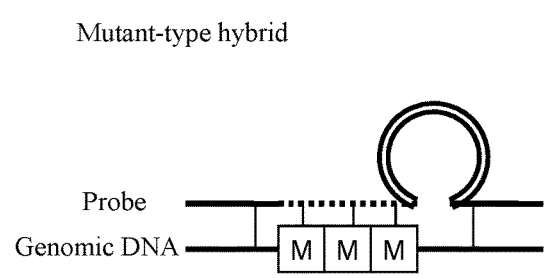

As for the probe of the above-described (a), a probe which is consisted of a nucleotide sequence complementary to an entire nucleotide sequence of the mutant-type DNA or a nucleotide sequence complementary to a part of nucleotide sequence of the mutant-type DNA including the inserted nucleotide region (a nucleotide sequence which is 100% complementary to an entire or a part of a nucleotide sequence), may be used. When such probe is used, in the wild-type hybrid, the sequence complementary to the inserted nucleotide region forms a loop structure on the probe and, the mutant-type hybrid does not form a loop structure. Its schematic diagram is described in FIGS. 12A and 12B. It should be noted that, in FIGS. 12A and 12B, MMM represents an inserted nucleotide region; a dotted line represents a complementary strand of the inserted nucleotide region, respectively.

Such probe includes, specifically, a complementary strand of a nucleotide sequence which is made by binding the inserted nucleotide and each 5 to 1000 nucleotides, preferably 5 to 150 nucleotides on its both sides, and the like. In other words, a nucleotide sequence which is complementary to the mutant-type DNA, and which is complementary to a sequence consisted of an inserted nucleotide of the mutant-type DNA and each 5 to 1000 nucleotides, preferably 5 to 150 nucleotides on its both sides, is included.

As for the probe of the above-described (b), a probe in which a nucleotide sequence which does not hybridize with wild-type DNA and mutant-type DNA is inserted into a nucleotide sequence complementary to the inserted nucleotide region of the above described probe (a) or is inserted into next to said nucleotide sequence, may be used. When such probe is used, the wild-type hybrid forms a loop structure by a nucleotide sequence complementary to the inserted nucleotide region and an inserted nucleotide sequence on the probe, and the mutant-type hybrid forms a loop structure by the nucleotide sequence inserted on the probe. That is, the loop structure of the wild-type hybrid and that of the mutant-type hybrid are different in structure. Its schematic diagram is described in FIGS. 13A-13F. It should be noted that, in FIGS. 13A-13F, MMM represents a inserted nucleotide region; a dotted line represents a complementary strand of the inserted nucleotide region; and a double line represents a nucleotide chain optionally inserted in the probe, respectively.

Such probe includes, specifically, a complementary strand of a nucleotide sequence which is made by binding an inserted nucleotide region which is inserted with usually 1 to 300 nucleotides, preferably 5 to 100 nucleotides to be used for constituting loop structure into the inserted nucleotide region of the mutant-type DNA, or into either of optional position next to 3' terminal or a position next to 5' terminal of the inserted nucleotide, with each 5 to 1000 nucleotides, preferably 5 to 150 nucleotides of its both sides. It should be noted that, in the case that the above-described nucleotide sequence to be inserted is 1 to 2 nucleotides, although the mutant-type hybrid cannot form loop structure, this case is also included in the probe of the above-described (b). In addition, the above-described nucleotide sequence to be inserted may be subdivided and inserted into several positions in the above-described place as long as the total number of nucleotides is within the above-described range.

(III-2) In the Case that the Hybrid Having a Loop Structure at the Genomic DNA Side is Intended to be Formed As for the probe relevant to the present invention in the present case, (a) a probe which forms a wild-type hybrid not having a loop structure and forms a mutant-type hybrid having a loop structure, or (b) a probe which forms a wild-type hybrid having a loop structure in the genome and forms a mutant-type hybrid having a loop structure in the genome, but the loop structures of the two are different, may be used.

Figure 14A:
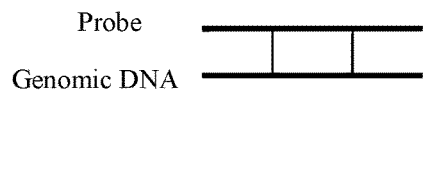
FIG. 14A depicts a wild-type hybrid.
Figure 14B:
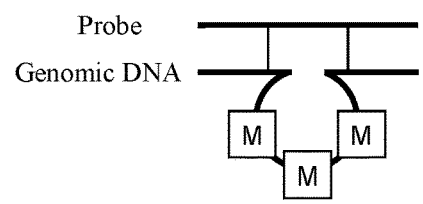
FIG. 14B depicts a mutant-type hybrid. M represents a an inserted nucleotide region.
Figure 15A:
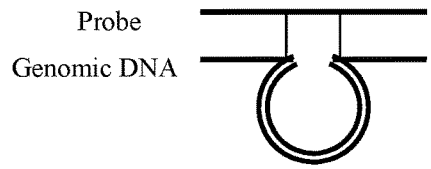
FIGS. 15A-15B depict a wild-type hybrid.
Figure 15C:
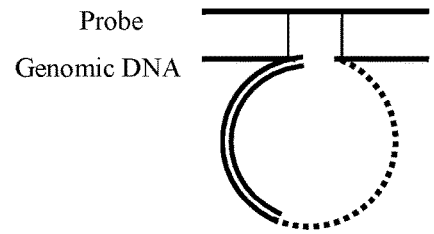
FIGS. 15C-15D depict a mutant-type hybrid. A dotted line represents a normal nucleotide region corresponding to a deficient nucleotide region, and a double line represents a nucleotide chain deleted arbitrarily from a sequence complementary to the genomic DNA at setting the probe.
Figure 15B:
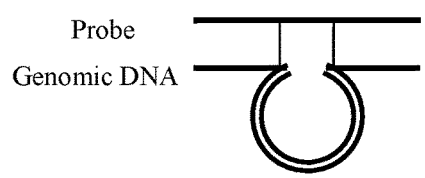
Figure 15D:
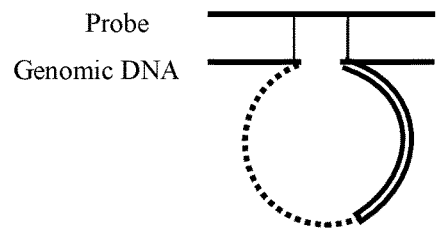

As for the probe of the above-described (a), a probe which is consisted of a nucleotide sequence complementary to an entire or a part of nucleotide sequence of the wild-type DNA (a nucleotide sequence which matches by 100% to an entire or a part of a nucleotide sequence), may be used. In other words, a probe which is consisted of a nucleotide sequence complementary to an entire or a part of nucleotide sequence other than the inserted nucleotide region inserted by mutation in the mutant-type DNA (it means a nucleotide sequence which is 100% complementary to an entire or a part of a nucleotide sequence), may be used. When such probe is used, the wild-type hybrid is the one not forming loop structure, and in the mutant-type hybrid, the inserted nucleotide region forms a loop structure on its genomic DNA. Its schematic diagram is described in FIGS. 14A and 14B. In addition, in FIGS. 14A and 14B, M represents an inserted nucleotide region.

Such probe includes, specifically, a complementary strand of a nucleotide sequence which is made by binding each 5 to 1000 nucleotides, preferably 5 to 150 nucleotides on both sides of the inserted nucleotide region of mutant-type DNA, and the like. In other words, a nucleotide sequence which is complementary to the wild-type DNA, and which is complementary to a nucleotide sequence of each 5 to 1000 nucleotides, preferably 5 to 150 nucleotides in two directions from a place corresponding to the inserted nucleotide region is included.

As for the probe of the above-described (b), a probe in which the nucleotide sequence for constituting a loop in the wild-type hybrid is excluded from a probe of above-described (a) at a nucleotide complementary to a nucleotide next to inserted nucleotide region as a base point, may be used. When such probe is used, in the wild-type hybrid, the nucleotide sequence excluded in the above forms a loop structure on the genomic DNA, and the mutant-type hybrid forms a loop structure by the nucleotide sequence excluded in the above and the inserted nucleotide region on the genomic DNA. That is, the loop structure of the wild-type hybrid and that of the mutant-type hybrid are different in structure. Its schematic diagram is described in FIGS. 15A-15D. It should be noted that, a dotted line represents an inserted nucleotide region; and a double line represents a nucleotide chain excluded arbitrarily from a sequence complementary to the genomic DNA at setting the probe.

Such probe includes, specifically, a complementary strand of a nucleotide sequence which is made by binding a nucleotide sequence of usually 5 to 1000 nucleotides, preferably 5 to 150 nucleotides from a nucleotide next to usually 1 to 300 nucleotides, preferably 5 to 100 nucleotides in the direction toward 3' side of the inserted nucleotide region of the mutant-type DNA and a nucleotide sequence of usually 5 to 1000 nucleotides, preferably 5 to 150 nucleotides from a nucleotide next to usually 1 to 300 nucleotides, preferably 5 to 100 nucleotides in the direction toward 5' side. In this regard, however, the complementary strand of a nucleotide sequence which is made by binding a nucleotide sequence from a nucleotide next to 1 nucleotide in the direction toward 3' side of the inserted nucleotide region and bound a nucleotide sequence from a nucleotide next to 1 nucleotide on 5' side is excluded (because it is a probe of the above-described (a)). In addition, in the nucleotide next to 1 to 300 nucleotides in the direction toward 3' side of the inserted nucleotide region and the nucleotide next to 1 to 300 nucleotides in the direction toward 5' side, when a total number of these next nucleotides is 4 or less, although the wild-type hybrid cannot form the loop structure, this case is also included in the probe of the above-described (b). In addition, the above-described total number of next nucleotides is usually 1 to 300 nucleotides, preferably 5 to 100 nucleotides.

(IV) In the Case that a Loop Structure is Further Formed in the Chain Opposite Sides of the Nucleotide Chain Having a Loop Structure In the hybrids relevant to the present invention described in the above (I) to (III), when the loop structure is present in a nucleotide chain on the opposite sides of a nucleotide chain having a loop structure, namely, when the loop structure is present on the genomic DNA side, also on the probe side, and when the loop structure is present on the probe side, also on the genomic DNA side, separation capacity of mutant-type hybrid and wild-type hybrid can be improved by further forming a loop structure.

As for the probe in that case, in the case having a loop structure at the genomic DNA side (in the case that a further loop structure is intended to be formed on the probe side), a sequence to be used for forming a loop in the probe (usually 1 to 300 nucleotides, preferably 5 to 100 nucleotides) may be inserted into the probe. In the case having a loop structure at the probe side (in the case that a further loop structure is intended to be formed on the genomic DNA side), a complementary strand (usually 1 to 300 nucleotides, preferably 5 to 100 nucleotides) corresponding to a nucleotide sequence in the genomic DNA for forming a loop structure in the genomic DNA, may be removed from the probe.

[Intercalator Relevant to the Present Invention]

The intercalator which forms conjugate with the hybrid in the detection method of the present invention includes, specifically, for example, intercalators of the following (1) to (5), as well as intercalator analogs of the following (6) and (7). That is, (1) for example, acridine dyes such as acridine orange, (2) for example, ethidium compounds such as ethidium bromide, ethidium homodimer 1 (EthD-1), ethidium homodimer 2 (EthD-2), ethidium bromide monoazide (EMA), dihydro-ethidium, (3) for example, iodine compounds such as propidium iodide, hexidium iodide, for example, 7-amino actinomycin D (7-AAD), for example, cyanine dimer dyes such as POPO-1, BOBO-1, YOYO-1, TOTO-1, JOJO-1, POPO-3, LOLO-1, BOBO-3, YOYO-3, TOTO-3 (all items are trade name of Molecular Probes, Inc.), (4) for example, cyanine monomer dyes such as PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5 (all items are trade name of Molecular Probes, Inc.), (5) for example SYTOX dyes such as SYBR Gold, SYBR Green I and SYBR Green II, SYTOX Green, SYTOX Blue, SYTOX Orange (all items are trade name of Molecular Probes, Inc.), for example, GelRed dyes such as GelRed (trade name of Wako Pure Chemical Industries, Ltd.), (6) the ones which bind to minor groove of DNA double helix [for example, 4',6-diamidino-2-phenyl indole (DAPI: trade name of Molecular Probes, Inc.), etc.], (7) the ones which specifically bind to adenine-thymine (AT) sequence [for example, Pentahydrate (bis-Benzimide) (Hoechst 33258: trade name of Molecular Probes, Inc.), Trihydrochloride (Hoechst 33342: trade name of Molecular Probes, Inc.), bisbenzimide dye (Hoechst 34580: trade name of Molecular Probes, Inc.), etc., for example, acridine dyes such as 9-amino-6-chloro-2-methoxy acridine (ACMA), bis-(6-chloro-2-methoxy-9-acridinyl) spermine (acridine homodimer), for example, hydroxystilbamidine, etc.] and the like.

[Method for Detecting Mutant-Type DNA or/and Wild-Type DNA of the Present Invention]

The method for detecting mutant-type DNA or/and wild-type DNA of the present invention is comprised of:

(1) a step in which at least one of mutant-type DNA relevant to the present invention or/and wild-type DNA relevant to the present invention are contacted with the probe relevant to the present invention to form a mutant-type hybrid or/and a wild-type hybrid, (2) a step in which the obtained mutant-type hybrid or/and a wild-type hybrid are contacted with a intercalator relevant to the present invention; and (3) a step in which the presence or absence of mutant-type DNA or/and wild-type DNA is detected by separating the conjugate of mutant-type hybrid and intercalator or/and the conjugate of wild-type hybrid and intercalator.

In the method of forming mutant-type hybrid or/and a wild-type hybrid in the above-described (1) (hereinafter, sometimes, said reaction is abbreviated as LH reaction), the DNA relevant to the present invention is contacted with the probe relevant to the present invention, and subjected to the DNA molecule association reaction, thereby the hybrid may be formed. It should be noted that, when the DNA relevant to the present invention forms a double-strand, the double-stranded DNA is converted into single strand by means of heat treatment (90 to 100° C.) or alkaline treatment (treatment with sodium hydroxide, etc.) and the like carried out usually in this field and then said DNA is contacted with a probe relevant to the present invention and may be subjected to the LH reaction. In addition, when a hybrid obtained by said LH reaction has a protruding end, it is preferable to treat the protruding end by the end-blunting treatment. Thereby, since single strand is not present at the terminal of the hybrid, it is possible to reduce the influence on the separation due to the existence of single strand. Said blunt-ending treatment includes a DNA extension reaction using an enzyme having polymerase activity and a decomposition reaction of terminal single-stranded DNA using an enzyme having exonuclease activity, and the like. Among them, the DNA extension reaction is preferable, because the longer double-stranded moiety in the hybrid is the more stable for the hybrid relevant to the present invention.

The above-described DNA molecule association reaction is performed by adding the probe relevant to the present invention to water or a buffer solution containing the DNA relevant to the present invention so as to make the concentration in the solution 20 nM to 2 µM, preferably 100 nM to 500 nM, and by reacting usually at 30 to 55° C. for usually 1 to 600 seconds, preferably for 1 to 30 seconds. Deionized sterile water is preferred as the water containing the DNA relevant to the present invention. The buffer solution is not particularly limited as long as it is well known per se for use in this field, and includes, for example, Tris buffer solution, phosphate buffer solution, veronal buffer solution, borate buffer solution, Good's buffer solution and the like, and the pH is also not particularly limited, but it is usually between 5 and 9.

The above-described end-blunting reaction may be carried out according to the end-blunting reaction well known per se, for example, 1 ng to 1 µg of the hybrid is added to 20 to 40 µL of water or a buffer solution, and further 1 to 5 U of an enzyme having exonuclease activity, if need arises, together with 4 kinds of deoxyribonucleotide triphosphates (dNTPs) of each usually 0.01 to 50 nmol, preferably 0.1 to 20 nmol, is added thereto, and allowed to react usually at 30 to 70° C., preferably at 35 to 60° C. usually for 10 to 120 minutes, preferably for 30 to 60 minutes. The water or the buffer solution in said reaction includes the same ones as described in the section of the above-described molecule association reaction. The above-described enzyme having exonuclease activity includes, for example, T4 DNA polymerase, KOD DNA polymerase, pfu DNA polymerase and the like.

The above-described DNA extension reaction is performed by the following procedure: 1 ng to 1 µg of the hybrid obtained by the molecule association reaction is added to 20 to 40 µL of water or a buffer solution, and further 4 kinds of deoxyribonucleotide triphosphates (dNTPs) of each usually 0.01 to 50 nmol, preferably 0.1 to 20 nmol, and 1 to 5 U of an enzyme having polymerase activity are added thereto, and allowed to react usually at 30 to 80° C., preferably at 65 to 75° C. usually for 10 seconds to 10 minutes, preferably for 1 to 4 minutes. The water or the buffer solution in said reaction includes the same ones as described in the section of the above-described molecule association reaction. In addition, the enzyme having polymerase activity includes, for example, T4 DNA polymerase, KOD DNA polymerase, pfu DNA polymerase, Taq DNA polymerase, Klenow fragment, and the like. Among them, thermostable DNA polymerase such as Taq DNA polymerase and KOD DNA polymerase and the like are preferable.

As for the DNA relevant to the present invention in the reaction of the above-described (1), the one which is amplified according to a known PCR reaction may be used. In that case, since the PCR reaction products is double-stranded DNA, it may be applied to the LH reaction after processing the above-described double-stranded DNA to single strand. In addition, when the PCR reaction solution including PCR reaction product is subjected to the LH reaction, and subjected to the DNA extension reaction as it is, since the reaction can proceed without addition of dNTPs and the enzyme having polymerase activity, said method is preferable to be used.

The LH reaction relevant to the present invention is preferable to constitute a reaction cycle by adding the single strand formation treatment of the double-stranded DNA by heating before the molecule association reaction. Specifically, for example, to the water or the buffer solution containing the DNA relevant to the present invention, the probe relevant to the present invention is added so as to make the concentration in the solution 20 nM to 2 µM, preferably 100 nM to 500 nM, and after that, for example, by setting the reaction at 90 to 100° C. for 2 to 4 minutes (heat denaturation) and the reaction at 30 to 55° C. for 1 to 30 seconds (DNA molecule association reaction) as 1 cycle, and carrying out this reaction for 1 to 4 cycles, the hybrid may be formed. In addition, further, the cycle reaction may be carried out by adding the extension reaction, and in that case, by setting the reaction at 90 to 100° C. for 2 to 4 minutes (heat denaturation), the reaction at 30 to 55° C. for 1 to 30 seconds (DNA molecule association reaction) and 65 to 75° C. for 1 to 4 minutes (DNA extension reaction) as 1 cycle, and carrying out this reaction for 1 to 4 cycles, the hybrid may be formed. It should be noted that, when the extension reaction is carried out, since the DNA molecule association reaction proceeds even under the condition at the DNA extension reaction, the LH reaction may be carried out by setting the reaction at 90 to 100° C. for 2 to 4 minutes (heat denaturation) and the reaction at 65 to 75° C. for 1 to 4 minutes (DNA molecule association, DNA extension reaction) as 1 cycle, and by carrying out the reaction for 1 to 4 cycles.

The cycle reaction of heat denaturation, DNA molecule association reaction and DNA extension reaction is performed specifically as bellows. That is, first, for example, to 20 to 40 µL of a buffer solution such as 10 to 50 mM Tris buffer solution (pH 8.4 to 9.0) in which 100 ng of DNA to be used target has been dissolved, the probe relevant to the present invention is added so as to make the concentration in the solution be 20 nM to 2 µM, preferably 100 nM to 500 nM, more preferably 100 nM to 200 nM. After that, for example, setting the reactions at 90 to 100° C. for 2 to 4 minutes (heat denaturation), at 30 to 55° C. for 1 to 30 seconds (DNA molecule association reaction), and at 65 to 75° C. for 1 to 4 minutes (DNA extension reaction) as 1 cycle, and by carrying out the reactions for 1 to 4 cycles, hybrid is formed, As mentioned above, when the DNA relevant to the present invention is amplified by the PCR reaction, and subsequently subjected to the LH reaction, it is performed specifically as follows. That is, for example, 1 to 100 pg of DNA to be used as a template is dissolved in 20 to 40 µL of a buffer solution such as Tris-HCl buffer solution, etc., and to this solution, usually 1 to 100 pmol, preferably 1 to 50 pmol of 2 kinds of primers (Forward, Reverse) for amplifying the objective region, respectively, and 4 kinds of deoxyribonucleotide triphosphates (dNTPs) so that it provides usually 0.01 to 50 nmol, preferably 0.1 to 20 nmol respectively, are added. Further, 1 to 5 U of a thermostable DNA such as Taq DNA polymerase or KOD DNA polymerase is coexisted therein, and for example, by setting the reaction (1) at 93 to 98° C. for 10 seconds to 10 minutes→0 (2) at 50 to 60° C. for 10 seconds to 3 minutes→at 65 to 75° C. for 1 to 5 minutes as 1 cycle, 30 to 40 cycles of repeating reaction are performed. After that, to the obtained reaction solution, the probe relevant to the present invention is added by 0.1 to 10 times amount of the DNA to be used as a template, for example, 0.1 to 500 pmol, preferably 0.1 to 50 pmol, and the LH reaction is performed as described above.

In addition, when a single-stranded DNA is amplified by the PCR reaction as in the above-mentioned, it is also possible to carry out the LH reaction simultaneously with said PCR reaction. In that case, as for the probe relevant to the present invention, the one which is modified at 3'-terminal and 5'-terminal with phosphate group and the like is employed, and under the presence of said probe, the above-described PCR reaction may be carried out. Specifically, for example, 1 to 100 pg of the DNA to be used as a template is dissolved in 20 to 40 µL of a buffer solution such as 10 to 50 mM Tris-HCl buffer solution (pH 8.4 to pH 9.0); and this solution is further added with, usually 1 to 100 pmol, preferably 1 to 50 pmol of 2 types of primers (Forward, Reverse), respectively, usually 0.01 to 50 nmol, preferably 0.1 to 20 nmol of 4 kinds of deoxyribonucleotide triphosphate (dNTPs), respectively, and usually 0.1 nmol to 500 pmol, preferably 0.1 to 50 pmol of the probe relevant to the present invention which is modified at 3'-terminal and 5'-terminal; and under existence of, for example, 1 to 5 U thermostable DNA polymerase, the reaction is performed, for example, by setting the reactions (1) at 93 to 98° C. for 10 seconds to 10 minutes→(2) at 50° C. to 60° C. for 10 seconds to 3 minutes→(3) at 65° C. to 75° C. for 1 to 5 minutes as 1 cycle, and repeating the cycle for 30 to 40 times.

As for the step of the above-described (2) in which the hybrid is contacted with an intercalator relevant to the present invention, the step is performed by adding an intercalator so that it provides 10 nmol/L to 10 µmol/L, preferably 10 nmol/L to 1 µmol/L in the water or the buffer solution containing 1 ng to 1 µg of the hybrid. It should be noted that, said contact step may be carried out at the same time with the step (3) for separating the conjugate of mutant-type hybrid and intercalator or/and the conjugate of wild-type hybrid and intercalator (separation step), and in that case, the intercalator may be added to the sample and subjected to separation, or may be added in the separation solution. As for the concentration of the intercalator in the present case, the intercalator may be added so that the concentration in the sample provides the above-described concentration.

As for the above-described separation step (3), there is no limitation specifically so long as it is a method for separating DNA usually used in this field, in particular the method which is capable of separating double-stranded DNA, and, the method in which separation is based on the difference of molecular weight, molecular structure or/and the difference in electric charge, etc. is preferable. The method for separating on the basis of the difference in said molecular weight, molecular structure or/and electric charge includes, specifically, for example, high performance liquid chromatography (HPLC), electrophoresis, a separation method using filter, and the like. Among them, the electrophoresis is more preferable.

When the HPLC method is used, it may be carried out according to the method described, for example, in Anal. Chem. 65, 5, 613-616 (1993), WO03/014398, WO03/031580, U.S. Pat. No. 5,585,236, U.S. Pat. No. 5,772,889, U.S. Pat. No. 5,972,222, etc. (Ion-pair reverse-phase high pressure liquid chromatography, Matched ion polynucleotide chromatography, etc.). When the separation method using filter is employed, it may be carried out according to the method described, for example, in Panasonic Technical Journal Vol. 57 No. 3 Oct. 2011, JP-A-2009-125009, etc.

The electrophoretic method includes, electrophoreses such as, for example, isoelectric focusing method, SDS-polyacrylamide electrophoresis, agarose gel electrophoresis, acrylamide gel electrophoresis, capillary electrophoresis, capillary chip electrophoresis and dielectrophoretic method, etc. Among them, from the reasons of good cooling efficiency, applicable high voltage and separation efficiency, capillary electrophoresis or capillary chip electrophoresis is preferable, and capillary chip electrophoresis which is suitable for micro-scale sample analysis is particularly preferable. It should be noted that, the conditions of these separation methods may be carried out according to the method well-known per se, for example, the capillary-chip electrophoresis may be carried out according to the method described in WO2007/027495, etc.

As for a method for detecting the mutant-type DNA or wild-type DNA by separation in the above-described (3) may be performed according to the method usually performed in this field, specifically, for example, a method in which, using the DNA of the same nucleotide sequence as the mutant-type DNA relevant to the present invention or the DNA of the same nucleotide sequence as the wild-type DNA relevant to the present invention, the conjugate of hybrid and intercalator is separated by the detection method of the present invention, and from the situation (degree) of separation thereof, mutant-type DNA or wild-type DNA is detected, is included. For example, in the case that the separation method is electrophoretic method, mutant-type DNA or wild-type DNA may be detected from its electrophoretic mobility, migration distance or migration time.

As for the detection method in the above-described (3), any kind of detection method can be used if it is a method well-known per se, and detection may be performed by an instrument such as differential refractive index detector, fluorescence detector, UV detector, and among them, detection by UV detector or fluorescence detector is preferable, and detection by fluorescence detector is more preferable.

When the above-described detection is carried out, in order to detect the conjugate of hybrid and intercalator, usually, fluorescence of the intercalator may be detected. The detection may be carried out using a probe labeled with a fluorescence in advance by detecting a labeled fluorescence of the probe in the conjugate carried out after the above-described step (1) and step (2), followed by the separation of step (3). When a probe labeled with fluorescence in advance is used, as described above, after the step (1), the step (2) and separation step (3) are performed at the same time, and then fluorescence label may be detected.

The fluorescence label of the probe employed here includes, for example, cyanine dye. The cyanine dye mentioned here is a compound in which two heterocyclic rings are bound with a methine group or a polymethine group, and at least one of the heterocyclic rings is nitrogen-containing heterocycle, and the one, in which both of the above-described heterocyclic rings are nitrogen-containing heterocycle, is preferable. As a substituent group derived from above-described cyanine dye, for example, a dye derived from Cy-based dyes described in U.S. Pat. No. 4,981,977, U.S. Pat. No. 5,268,486, U.S. Pat. No. 5,486,616, etc., a dye derived from Dy-based dyes described in U.S. Pat. No. 6,083,485, etc., a dye derived from HiLyte-based dye described in WO2006/047452, and a dye derived from Alexa-based dye are preferable. In addition, the one derived from commercially available dyes may be employed, for example, in the case that a dye derived from Cy-based dye is employed, the one derived from Cy3, Cy3.5, Cy5, Cy5.5, Cy7, and so on [all of them are trade name of Amersham Biosciences]; as a dye derived from Dy-based dye, the one derived from DY-700, DY-701, DY-730, DY-731, DY-732, DY-734, DY-750, DY-751, DY-752, DY-776, DY-780, DY-781, DY-782, and so on; as a dye derived from HiLyte-based dye, the one derived from HiLyte Fluor 555, HiLyte Fluor 647, HiLyte Fluor 680, HiLyte Fluor 750, and so on [all of them are trade name of AnaSpec Inc.]; as a dye derived from Alexa-based dye, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700, Alexa Fluor Dye 750, and so on [all of them are trade name of Molecular Probes]; are included as a desirable dye. Among them, a dye derived from Cy-based dye is preferable, among them a dye derived from Cy5 is preferable. It should be noted that, the fluorescence labeling may be performed according to a known method.

In the case that the mutant DNA in a human genomic DNA derived from cancer patient is detected by the detection method of the present invention, specifically, for example, it is carried out as follows.

That is, the human genomic DNA which is extracted and purified by using a commercially available kit and the like is used as a sample, and the PCR reaction is performed. The sample for the PCR reaction may be prepared, for example, by dissolving the DNA primers of detection target, 4 kinds of deoxyribonucleotide triphosphate (dNTPs) and Taq DNA polymerase in 20 μL of buffer solution such as Tris-HCl buffer solution, so that the DNA primers (Forward and Reverse) becomes usually 100 to 1000 nM, respectively, 4 kinds of dNTPs becomes usually 0.1 to 500 nM, respectively, and Taq DNA polymerase becomes 1 to 5 units, and by adding 1 to 100 ng of human genomic DNA thereto. As for the PCR reaction, for example, by performing 35 to 40 cycles of a reaction cycle composed of (1) 93 to 98° C. for 10 to 30 seconds, (2) 50 to 60° C. for 10 to 30 seconds, and (3) 68 to 72° C. for 1 to 3 minutes, the target single-stranded DNA can be amplified. To the PCR reaction solution containing the obtained target single-stranded DNA, 0.1 to 10 times the PCR primer amount of probe is added, further hybrid reaction may be carried out. That is, for example, to the PCR reaction solution, the prove relevant to the present invention is added so as to give a final concentration of 100 to 500 nM, and it is reacted at 90 to 100° C. for 2 to 4 minutes, 30 to 55° C. for 1 to 30 seconds, 65 to 75° C. for 1 to 4 minutes, and by repeating the reaction for 1 to 4 cycles, the hybrid of DNA of detection purpose can be obtained. The obtained solution is subjected to electrophoresis in an electrophoresis solution containing 10 nmol to 1 μmol/L intercalator, detection is carried out using a fluorescence detector etc., and based on its mobility, presence or absence of the mutant-type DNA can be detected.

Hereinafter, the present invention is explained in more detail by referring to Examples, Comparative Examples and so on, however, the present invention is not limited thereto in any way.

EXAMPLES

Synthetic Example 1: Preparation of Sample Clone Having a Sequence of Mutant-Type DNA and Wild-Type DNA on the EGFR Gene Exon 19

(1) Cloning of Target Sequence from Clinical Specimen

It has been known that in the EGFR gene exon 19, the genetic mutation by in-frame deletion occurs in the region starting from a codon 747-749 (K. Endo, A. Konishi, H. Sasaki et al., Lung Cancer 50 (3), 375 (2005)). And so, from samples derived from actual lung cancer patients, a DNA sequence comprised of said region was amplified by the PCR, and further, the amplification product thereof was cloned into a plasmid using pGEM-T Vector system (Promega Corp.), and sample clones having a sequence of these 5 kinds of mutant-type DNA and wild-type DNA were obtained. The details of this procedure are described below.

That is, plural tissue sections of human lung adenocarcinoma obtained as a clinical specimen were prepared, and using Pinpoint Slide DNA Isolation System (manufactured by Zymo Research Corporation), and according to a product protocol attached in kit, the spliced out tissue sections (2 mm×4 mm) were treated with proteinase K at 70° C. for 5 hours. Subsequently, by applying heat treatment at 95° C. for 10 minutes, genomic DNA was extracted from each tissue fragment. Among 30 µL of DNA extract solution obtained herein, using 1 µL as a template material, and using AccuPrime Taq polymerase system (kit for PCR reaction, manufactured by Invitrogen Corp.), the PCR reaction was carried out. That is, first, according to the product protocol attached to kit, using each 1.0 µL, of 10 µM primer solution (EGFR19J: ggactctggatcccagaaggtg [SEQ ID NO: 1] and EGFR19U: ctgaggttcagagccatggac [SEQ ID NO: 2]), as well as kit attached, 2.0 µL of PCR reaction buffer, 0.5 µL of AccuPrime Taq enzyme, and 16.5 µL of deionized sterile water, 20.0 µL of reaction solution for PCR was prepared. Then, each 2 pg of the sample clone was added and suspended in 20 µL of the reaction solution for PCR, and used it as a sample for PCR. Using this sample for PCR, and using DNA Thermal Cycler (DNA Engine PTC200) of MJ Research Inc., the PCR reaction was performed for 30 cycles under the following reaction conditions.

PCR reaction condition:
Heat denaturation: 95° C., 15 seconds
Annealing: 55° C., 15 seconds
Polymerization reaction: 68° C., 47 seconds Each of plural PCR products obtained by this PCR reaction (146 bp in the wild type) was inserted into a plasmid vector pGEM-T Easy by TA cloning method using pGEM-T Vector System (Promega Corporation). That is, to each 3.0 µL of the PCR amplification product, 1.0 µL of pGEM-T Easy Vector (produced by Promega Corporation), 5.0 µL of Rapid Ligation Buffer of DNA Ligation Kit (produced by Promega Corporation) and 1.0 µL of T4 ligase were added to make the total volume 10.0 µL, and incubated at room temperature for 60 minutes, thus the recombinant DNA was obtained After that, using E. coli JM109 Competent Cells (produced by Toyobo Co., Ltd.), and according to its product protocol, the transformation of E. coli JM109 Competent Cells was carried out at 42° C. for 45 seconds using the recombinant DNA obtained in the above. After that, the obtained transformant was cultured on a plate of LB-agar medium including 100 µg/mL ampicillin, 0.2 mM isopropyl-β-thiogalactopyranoside (IPTG) and 40 µg/mL X-Gal at 37° C. for 16 hours. After cultivation, by picking up white colonies in the medium, the transformant for the each clone which was transduced with recombinant DNA inserted with the objective DNA fragment, were obtained. After that, using plasmid extraction kit (QIAprep Spin Miniprep) of Qiagen Corp., the process of extraction/purification of DNA was carried out.

That is, the transformant for each clone which was proliferated overnight in LB liquid medium containing 5 mL of 100 µg/mL ampicillin was collected by centrifugation; and after bacteriolysis by alkaline method, the lysate was neutralized with acidic potassium acetate solution, and from their supernatant solution after centrifugation, the plasmid DNA was purified by a purification column provided in the kit.

(2) Confirmation of Sequence of Mutant-Type DNA and Wild-Type DNA

Using candidate clones which were cloned in the above-described (1) and expected to include plural kinds of sequences of mutant-type DNA or wild-type DNA, the sequence analysis by the Big Dye Terminator kit (manufactured by Applied Biosystems, Inc.) was carried out by the following procedure according to the product protocol.

That is, to a mixture of 2 µL (100 ng) of sample DNA (each clone), 1 µL (5 pmol) of T7 promoter primer, and 8 µL of premix attached in kit, including enzyme, dNTPs, reaction buffer and fluorescent dye, ddH$_2$O was added so that it makes total volume 20 µL, and by using DNA Thermal Cycler (DNA Engine PTC200, manufactured by MJ Research Inc.), sequencing reaction of 30 cycles was carried out by the following reaction conditions.

96° C., 2 minutes→(96° C., 10 seconds→50° C., 5 seconds→60° C., 3 minutes)×25→4° C.

After refining the obtained sequence reaction product utilized the gel filtration column (manufactured by Qiagen, Corp.), using a sequencer (3130 Genetic Analyzer, manufactured by Applied Biosystems) and according to the procedure manual attached to equipment, sequence determination of all candidate sequences was completed.

As the result, it was confirmed that in the EGFR gene exon 19, the sample clones having the sequences of 5 kinds of mutant-type DNA and wild-type DNA shown in the following table 1 could be prepared. It should be noted that, each sample clone of mutant-type DNA was represented as G1 to G5, and wild-type DNA as N. In the table below, the place shown by "-" is a sequence region of deletion observed against the sequence of wild type.

TABLE 1

| ID. | Sequence | Number of deleted nucleotide(nt) |
|---|---|---|
| G1 [SEQ ID NO: 3] | atcaaggaa---------ccaacatctccgaaa | 9 |
| G2 [SEQ ID NO: 4] | atcaa-------------aacatctccgaaa | 15 |
| G3 [SEQ ID NO: 5] | atcaag------------acatctccgaaa | 15 |
| G4 [SEQ ID NO: 6] | atcaaggaat-----------ctccgaaa | 15 |
| G5 [SEQ ID NO: 7] | atcaagg--------------ttccgaaa | 18 |
| N (Wild-type) [SEQ ID NO: 8] | atcaaggaattaagagaagcaacatctccgaaa | 0 |

(3) Amplification of Sample DNA

Using each sample clone of the above-described G1 to G5 and N as a sample, the PCR reaction was carried out using the AccuPrime Taq DNA Polymerase System (kit for the PCR reaction, manufactured by Invitrogen Corp.).

That is, firstly, according to the product protocol attached to the kit, using 1.0 μL of each 10 μM primer solution (EGFR19J: ggactctggatcccagaaggtg [SEQ ID NO: 1] and EGFR19U: ctgaggttcagagccatggac [SEQ ID NO: 2]), as well as 2.0 μL of PCR reaction buffer, 0.5 μL of Accuprime Taq enzyme, 20.0 μL of reaction solution for PCR, which are attached to the kit, and 16.5 μL of ddH$_2$O was prepared. Then, each 2 pg of the sample clone was added and suspended in 20 μL of reaction solution for PCR, and used it as a sample for PCR. Using this sample for PCR, and using DNA Thermal Cycler (DNA Engine PTC200) of MJ Research Inc., the PCR reaction of 30 cycles was performed under the following reaction conditions.

PCR reaction condition:
Heat denaturation: 95° C., 15 seconds
Annealing: 55° C., 15 seconds
Polymerization reaction: 68° C., 47 seconds Nucleotide size and nucleotide sequence of the obtained PCR amplification product were as follows.

TABLE 2

| ID NO.<br>(Nucleotide size) | Nucleotide sequence |
| --- | --- |
| G1<br>[SEQ ID NO: 9]<br>(137 bp) | ggactctggatcccagaaggtgagaaagtt<br>aaaattcccgtcgctatcaagaaccaacat<br>ctccgaaagccaacaaggaaatcctcgatg<br>tgagtttctgctttgctgtgtgggggtcca<br>tggctctgaacctcag |
| G2<br>[SEQ ID NO: 10]<br>(131 bp) | ggactctggatcccagaaggtgagaaagtt<br>aaaattcccgtcgctatcaaaacatctccg<br>aaagccaacaaggaaatcctcgatgtgagt<br>ttctgctttgctgtgtgggggtccatggct<br>ctgaacctcag |
| G3<br>[SEQ ID NO: 11]<br>(131 bp) | ggactctggatcccagaaggtgagaaagtt<br>aaaattcccgtcgctatcaagacatctccg<br>aaagccaacaaggaaatcctcgatgtgagt<br>ttctgctttgctgtgtgggggtccatggct<br>ctgaacctcag |
| G4<br>[SEQ ID NO: 12]<br>(131 bp) | ggactctggatcccagaaggtgagaaagtt<br>aaaattcccgtcgctatcaaggaatctccg<br>aaagccaacaaggaaatcctcgatgtgagt<br>ttctgctttgctgtgtgggggtccatggct<br>ctgaacctcag |
| G5<br>[SEQ ID NO: 13]<br>(128 bp) | ggactctggatcccagaaggtgagaaagtta<br>aaattcccgtcgctatcaaggttccgaaagc<br>caacaaggaaatcctcgatgtgagtttctgc<br>tttgctgtgtgggggtccatggctctgaacc<br>tcag |
| N (Wild-type)<br>[SEQ ID NO: 14]<br>(146 bp) | ggactctggatcccagaaggtgagaaagtta<br>aaattcccgtcgctatcaaggaattaagaga<br>agcaacatctccgaaagccaacaaggaaatc<br>ctcgatgtgagtttctgctttgctgtgtggg<br>ggtccatggctctgaacctcag |

Example 1: Separation/Detection of the LH Reaction Product in the Coexistence of Intercalator (1) Preparation of a Probe for Loop Hybrid Reaction (LH Probe)

The LH probe was designed so that when hybridized with wild-type DNA (N), it does not form a loop, and when hybridized with mutant-type DNA (G1 to G5) having a deletion mutation region, a complementary strand on the LH probe corresponding to the deficient nucleotide region forms a loop structures. That is, the following probe was used as a probe for LH reaction (EGFR 19 JWTF).

[SEQ ID NO: 15]
ggactctggatcccagaaggtgagaaagttaaaattcccgtcgctatcaa
ggaattaagagaagcaacatctccgaaagccaacaaggaaatcctcgat Synthesis of the above-described probe was performed through the use of the contract synthesis service of Sigma-Genosys Inc. In addition, in the Synthetic Examples and Examples of the present invention described below, oligonucleotide synthesis of primer and probe and labeling of fluorescent dye and so on, also utilized the contract synthesis service of Sigma-Genosys Inc.

Figure 16:
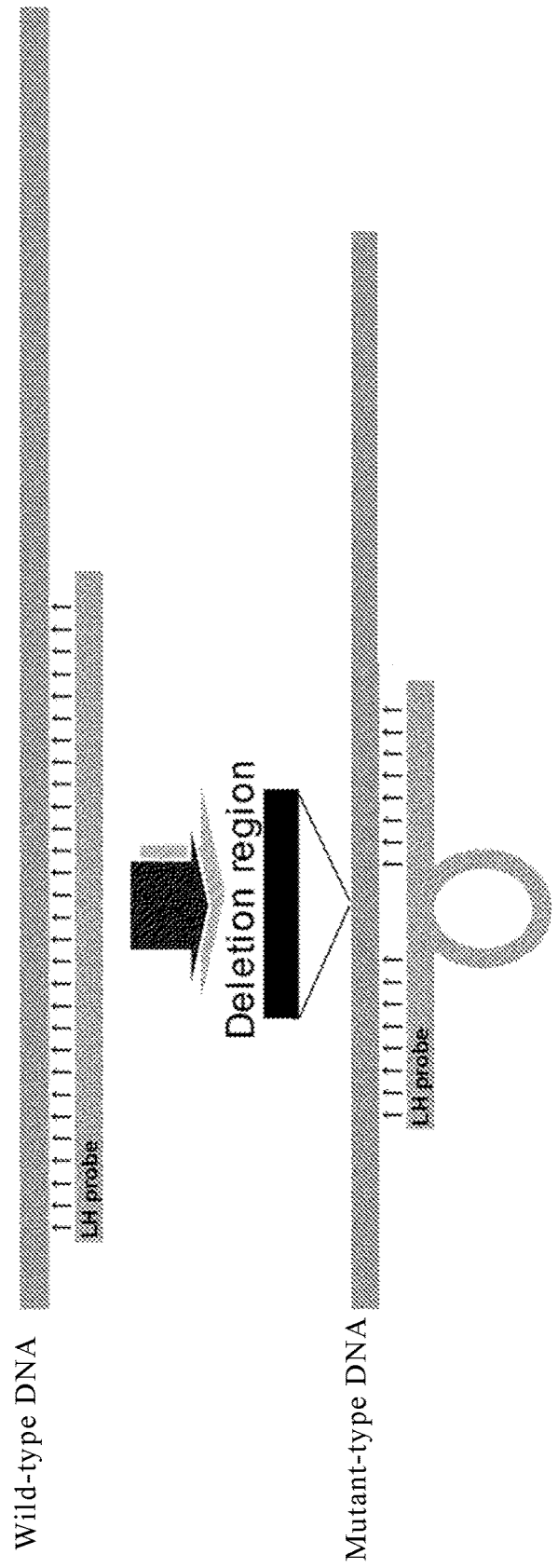
FIG. 16 illustrates the predicted result when a loop-hybrid probe is designed so that when hybridized with wild-type DNA it does not form a loop, and when hybridized with mutant-type DNA having a deletion mutation region, a complementary strand on the LH probe corresponding to the deficient nucleotide region forms a loop structures.

When the above-described probe is used, it is conceived that the hybrid of FIG. 16 is formed.

(2) LH Reaction

To each 4.5 μL of 6 types of PCR reaction solution obtained in Synthetic Example 1 (3), the LH probe (ID.=EGFR 19 JWTF) was added so as to make final concentration of 200 nM, and using DNA Thermal Cycler (DNA Engine PTC200, MJ Research Inc.), 1 cycle reaction was carried out under the following reaction conditions.

LH-reaction
Reaction solution 4.5 μL
LH probe 0.5 μL (2 μM)
105° C. hot lid
95° C. 2 minutes
55° C. 30 seconds
68° C. 4 minutes
4° C. stop the reaction (3) Electrophoretic Separation/Detection of the LH Reaction Products in the Coexistence of Intercalator (Microchip Electrophoresis)

Six kinds of reaction products obtained in the above-described LH reaction were subjected to the microchip electrophoretic method utilized the Agilent 2100 Bioanalyzer systems (Agilent Technologies Inc.). In the present electrophoretic method, Agilent DNA1000 Assay kit which is a dedicated reagent (produced by Agilent Technologies Inc.) was used, and 1.0 μL of each LH reaction product was applied. Here, at the time of separation/detection of the LH reaction product, since an intercalator dye and a polymer for electrophoresis attached to the kit are used in a premixed state, the LH reaction products are separated and detected in the coexisting state with the intercalator during the electrophoretic process.

Figure 17:
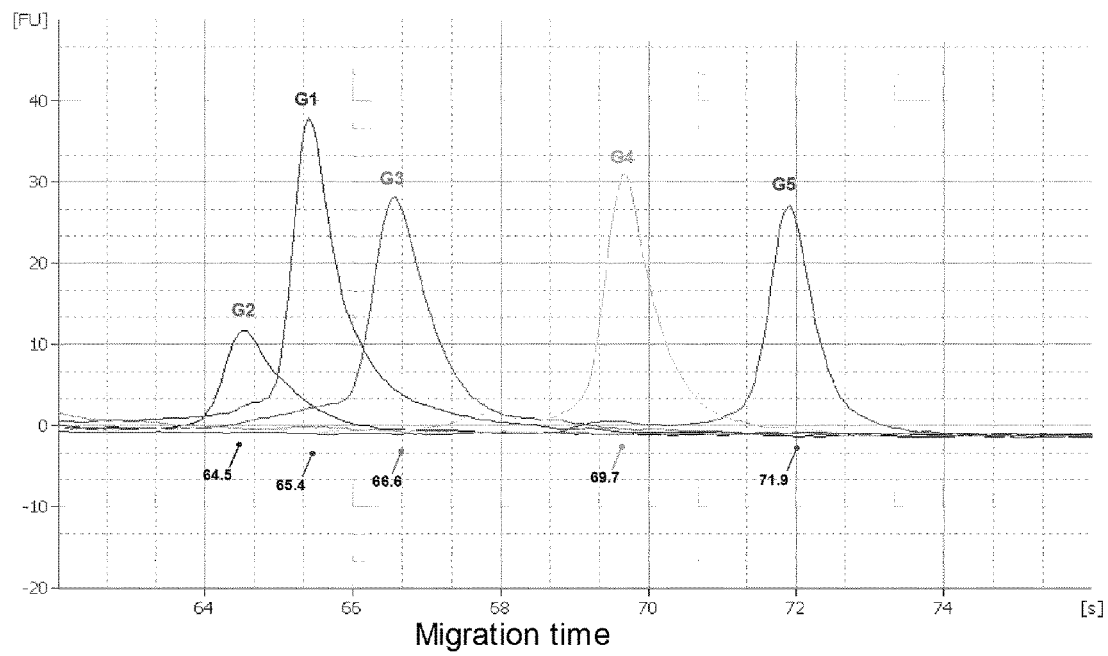
FIG. 17 is the result of separation and analysis carried out by microchip electrophoresis for the loop hybrid reaction product (LH reaction product) obtained using a wild-type DNA (N) and a mutant-type DNA (G1 to G5) in EGFR gene, in the coexistence of intercalator, in Example 1.

For the peak analysis after electrophoresis, using the system attached to Agilent 2100 Expert software, wave analysis and calculation of peak mobility were carried out. The results are shown in FIG. 17.

As is apparent from the results, according to the detection method of the present invention, it was shown that it was possible to separate all of the mutant genes of G1 to G5. In particular, it turned out that even though the nucleotide size of the mutant gene of G2 to G4 is identical (131 bp), these can be separated clearly.

Comparative Example 1: Separation/Detection of LH Reaction Products in the Absence of Intercalator As a comparison of Example 1, separation/detection by electrophoresis was performed with regard to the LH reaction products which was fluorescently labeled with Cy5

(1) Preparation of a Cy5-Labeled LH Probe

The probe sequence for the LH reaction used in Example 1 (1); the one in which 5' terminal of EGFR 19 JWTF [SEQ ID NO: 15] was fluorescently labeled with Cy5, was prepared.

(2) Detection of LH Reaction Products Using a Fluorescent Signal by the Cy5-Labeled LH Probe as an Indicator Using each 6 kinds of sample clone prepared in the above-described Synthetic Example 1 as a sample, LH reaction was carried out by the same method as Example 1 (2) except for using the above-described probe. Then, using the 6 kinds of the obtained LH reaction products, detection of deletion mutant-type DNA of EGFR gene was carried out. Specifically, using Agilent 2100 Bioanalyzer systems (Agilent Technologies Inc.), the LH reaction products were subjected to the microchip electrophoretic method in the same way as above described (3) except for changing the polymer for electrophoresis and the buffer for electrophoresis as described below. As for the polymer for electrophoresis, the one in which the intercalator dye was not added, but Cy5-dCTP (GE Biosciences Corp.), which was necessary for focus adjustment in the optical system of the microchip electrophoresis, was added so that it provides final concentration of 4.9 nM, was used. As for the electrophoresis buffer, the one in which the Cy5-dCTP was added so that it provides final concentration of 4.9 nM in the same manner as in the polymer for electrophoresis. In addition, instead of DNA fragments of 15 bp (low molecular weight marker) and 1500 bp (high molecular weight marker), which have been included for the purpose of a correction of the peak mobility calculation of the electrophoresis, Cy5-labeled DNA fragments of 15 bp and 1500 bp were used, and they were added to the electrophoresis buffer. That is, by the above-described electrophoretic conditions, separation/detection of the LH reaction products was carried in the absence of the intercalator.

Figure 18:
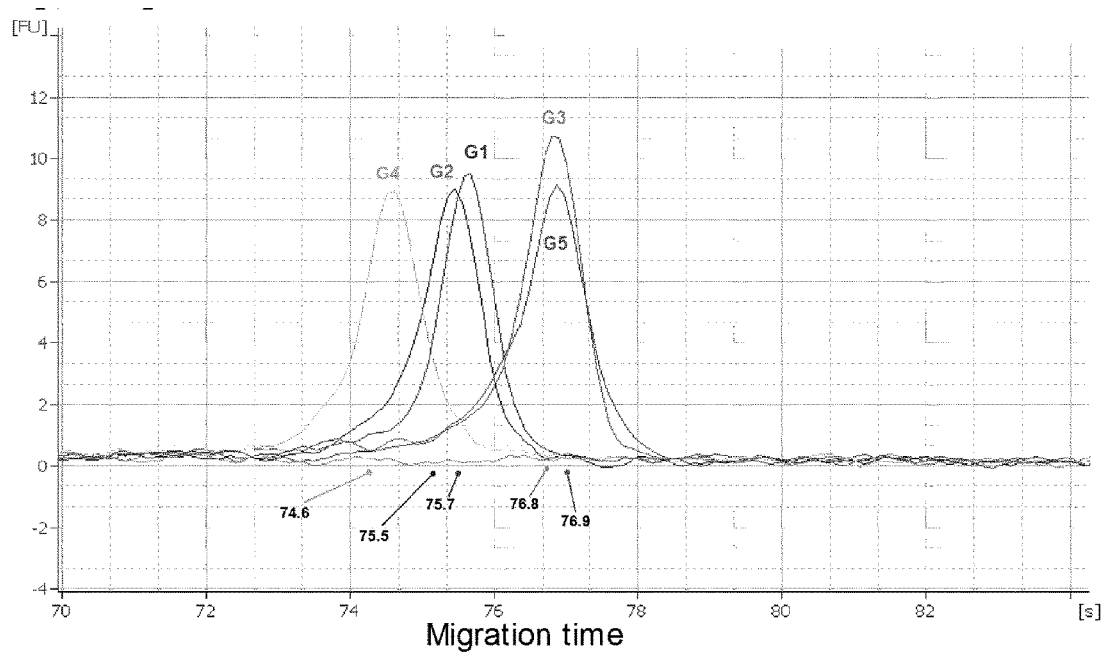
FIG. 18 is the result of separation and analysis carried out by microchip electrophoresis for the Cy5-labeled LH reaction product obtained using a wild-type DNA (N) and a mutant-type DNA (G1 to G5) in EGFR gene, in the absence of intercalator, in Comparative Example 1.

The results are shown in FIG. 18.

As is clear from the result in FIG. 18, it turned out that in the electrophoretic separation/detection of the LH reaction products in the absence of the intercalator, since the peaks derived from sample clones of G1 to G5 are overlapped, separation/detection cannot be achieved. That is, from the results of FIG. 17, it turned out that, by forming a bound substance of the intercalator and the LH reaction product during electrophoresis in the coexistence of the intercalator, the LH reaction products which could not be separated in the absence of the intercalator can be separated clearly.

Here, with respect to the results obtained in Example 1 and Comparative Example 1, the difference of the migration time of each peak in the electrophoresis was summarized in Table 3, and compared between the two.

TABLE 3

|  | Example 1 | Comparative Example 1 | Relative merits between presence and absence of intercalator |
|---|---|---|---|
| Time difference between G1 and G2 | 0.9 seconds | 0.2 seconds | Presence > Absence |
| Time difference between G1 and G3 | 1.2 seconds | 1.1 seconds | Comparable |
| Time difference between G1 and G4 | 4.2 seconds | 1.1 seconds | Presence > Absence |
| Time difference between G1 and G5 | 6.5 seconds | 1.2 seconds | Presence > Absence |
| Time difference between G2 and G3 | 2.1 seconds | 1.3 seconds | Presence > Absence |
| Time difference between G2 and G4 | 5.2 seconds | 0.9 seconds | Presence > Absence |
| Time difference between G2 and G5 | 7.4 seconds | 1.4 seconds | Presence > Absence |
| Time difference between G3 and G4 | 3.1 seconds | 2.2 seconds | Presence > Absence |
| Time difference between G3 and G5 | 5.3 seconds | 0.1 seconds | Presence > Absence |
| Time difference between G4 and G5 | 2.3 seconds | 2.3 seconds | Comparable |

From the results of Table 3, it turned out that even the same LH reaction product, by coexistence with intercalator, the discriminative ability in the electrophoretic separation can be improved significantly. This is considered that depending on the difference in the secondary structure of the loop in the hybrid to be formed by mutant-type DNA of G1 to G5 derived from each sample clone and the LH probe, the mode of interaction (binding) with the intercalator was very different, and as a result, it caused the difference of each peak mobility in the electrophoresis.

It should be noted that, it was confirmed that, in either of the results, since the secondary structure of loop shape was not formed on said probe at hybrid formation with wild-type DNA (N), the comparison with peak group detected for mutant-type (G1 to G5) remained in the baseline detection.

Comparative Example 2: Electrophoretic Separation/Detection of Double-Stranded DNA Fragment in the Coexistence of Intercalator To confirm whether the intercalator contributes to the improvement effect of separation performance of the double-stranded DNA in general, or it contributes to the improvement effect of separation performance of the hybrid according to the LH method, separation/detection in the presence of intercalator was carried out using double-stranded DNA which is not a hybrid according to the LH method (G1, G2, G3, G4, G5 in Table 2 of Example 1).

That is, each mutant-type DNA of G1 to G5 obtained in the above-described Synthetic Example 1 (3) was subjected to the microchip electrophoretic method using Agilent 2100 Bioanalyzer systems (Agilent Technologies Inc.). In the present electrophoretic method, Agilent DNA1000 Assay kit which is a dedicated reagent (produced by Agilent Technologies Inc.) was used, and 1.0 µL of each PCR amplification product was applied. Here, at the time of detection of the LH reaction products, since an intercalator dye attached to the kit and a polymer for electrophoresis is used in a premixed state, the LH reaction products are separated and detected in the coexisting state with the intercalator in the electrophoresis process.

For the peak analysis after electrophoresis, using the Agilent 2100 Expert software attached in system, the wave analysis and calculation of peak mobility were performed. The results are shown in FIG. 19.

Figure 19:
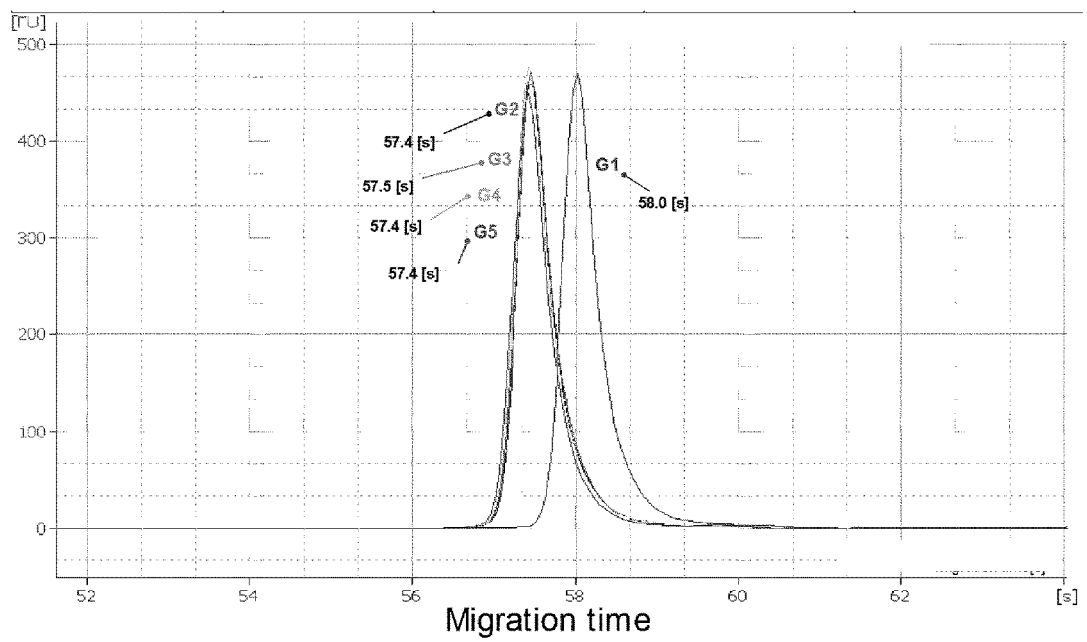
FIG. 19 is the result of separation and analysis carried out by microchip electrophoresis for a wild-type DNA (N) and a mutant-type DNA (G1 to G5) in EGFR gene, in the coexistence of intercalator, in Comparative Example 2.

As is apparent from FIG. 19, no difference was observed in the peak mobility of G2 to G4 having approximately equal nucleotide size (bp) of double-stranded DNA, and it turned out that even in the presence of intercalator, they cannot be separated.

When considered in conjunction with the results of Example 1, it turned out that the improvement effect of separation performance of intercalator does not exhibit against double-stranded DNA, but the one in which the hybrid obtained by LH method, i.e., the one which includes both double-stranded region and single-stranded region (LH reaction product) is bound with the intercalator, exhibits excellent effects. The reason is not clear, however, it is conceivable that since the LH method was originally intended to separate based on the difference in structure of the loop (single-stranded moiety), and further, structural change was caused by binding of the intercalator to the double-stranded moiety, thereby the separation performance was improved.

Comparative Example 3: Separation/Detection of LH Reaction Products in the Absence of Intercalator (Acrylamide Polymerization Gel Electrophoresis)

As a comparison of Example 1, detection of LH reaction products by intercalator staining after electrophoretic separation was carried out using the acrylamide polymerization gel electrophoresis.

Specifically, using 6 kinds of LH reaction products [the LH reaction products of mutant-type DNA (G1 to G5) derived from EGFR gene and the LH reaction products of wild-type DNA (N)] obtained by the LH reaction in Example 1 (2), the electrophoresis was carried out as described below. That is, to each 1.5 µL of 6 kinds of samples, 1.5 µL of gel loading buffer was added respectively, and the samples were electrophoresed on a 10% nondenaturing acrylamide polymerization gel. In addition, as molecular weight markers, using 1.5 µL of 100 bp ladder for size marker (produced by Promega Inc.), electrophoresis was carried out by loading on the same gel. The acrylamide polymerization gel used was a compact gel (Compact gel C10L, produced by ATTO Corp.) of 7 cm×7 cm, and electrophoresis was carried out at room temperature by a small electrophoretic equipment (Compact PAGE AE-7300, produced by ATTO Corp.) using Tris-glycine buffer solution (37.5 mM Tris and 288 mM glycine) as a buffer solution.

Figure 20:
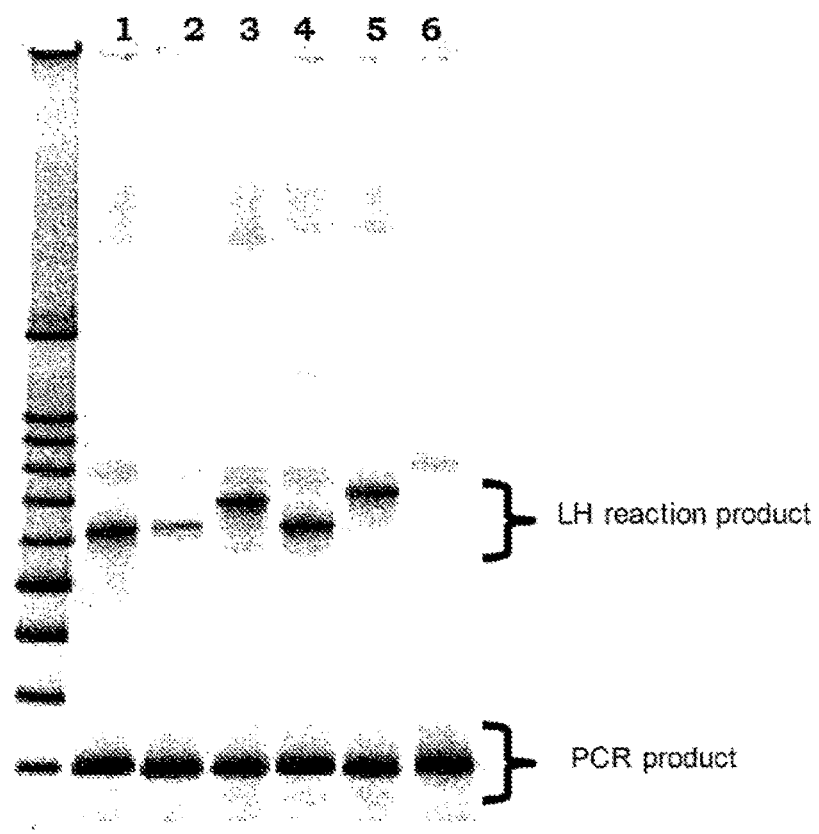
FIG. 20 is the result of separation and analysis, in which after the LH reaction product obtained using a wild-type DNA (N) and a mutant-type DNA (G1 to G5) in EGFR gene was migrated by gel electrophoresis, the intercalator was added thereto, and then measurement was carried out, in Comparative Example 3.

After the electrophoresis, the gel was stained 10 minutes with SYBR Green I (TAKARA BIO Inc., F0513), and washed with water, then using a laser imaging scanner (Amersham Biosciences Corp., STORM 860), detection was carried out. On this occasion, for the detection of fluorescence of SYBR Green I, excitation wavelength of 450 nm and detection filter 520LP was used. The results obtained are shown in FIG. 20. It should be noted that, in the Figure, lane 1 shows the result of the mutant-type DNA (G1); lane 2 shows the result of the mutant-type DNA (G2); lane 3 shows the result of the mutant-type DNA (G3); lane 4 shows the result of the mutant-type DNA (G4); lane 5 shows the result of the mutant-type DNA (G5); lane 6 shows the result of the wild-type DNA (N), respectively.

As is apparent from the results of FIG. 20, it turned out that, even LH reaction product, when electrophoresed without making it conjugate with intercalator and added the intercalator after electrophoresis, it does not contribute to the complete separation and detection of electrophoretic bands derived from sample clone of G1 to G5.

Comparative Example 4: Separation/Detection of Cy5-Labeled LH Reaction Product in the Absence of Intercalator (Acrylamide Polymerization Gel Electrophoresis)

As a comparison of Example 1, detection of LH reaction products utilized the Cy5 fluorescently-labeled probe was carried out using acrylamide polymerization gel electrophoresis.

Figure 21:
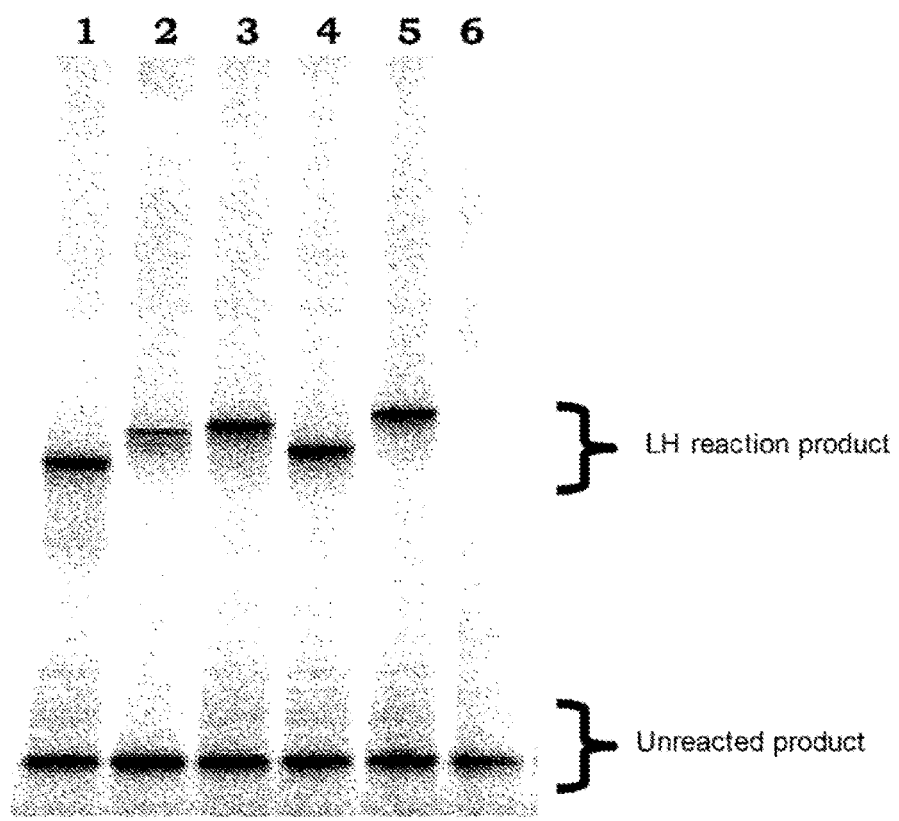
FIG. 21 is the result of separation and analysis carried out by gel electrophoresis for the Cy5-labeled LH reaction product obtained using a wild-type DNA (N) and a mutant-type DNA (G1 to G5) in EGFR gene, in the absence of intercalator, in Comparative Example 4.

Specifically, except for using 6 kinds of LH reaction products obtained by the LH reaction in Comparative Example 2 (2) [the LH reaction products of mutant-type DNA (G1 to G5) derived from EGFR gene and the LH reaction products of wild-type DNA (N)], the electrophoresis was carried out in the same way as the above-described Comparative Example 3. After the electrophoresis, the fluorescence detection was performed using excitation wavelength of 635 nm and detection filter 650LP. The obtained results are shown in FIG. 21. It should be noted that, in the Figure, lane 1 shows the result of the mutant-type DNA (G1); lane 2 shows the result of the mutant-type DNA (G2); lane 3 shows the result of the mutant-type DNA (G3); lane 4 shows the result of the mutant-type DNA (G4); lane 5 shows the result of the mutant-type DNA (G5); lane 6 shows the result of the wild-type DNA (N), respectively.

As is apparent from the results of FIG. 21, it turned out that, even LH reaction product, when electrophoresed and detected without making it bound substance with intercalator, the migration bands derived from sample clone of G1 to G5 cannot be separated/detected completely.

Example 2: Separation/Detection about the LH Reaction Product Derived from Single Nucleotide Substitution Mutant-Type DNA of KRAS Gene in the Coexistence of Intercalator (1) Preparation of Human Genomic DNA Derived from a Colorectal Cancer Patient The human genomic DNA derived from a colorectal cancer patient was prepared using QIAGEN QIAamp DNA Mini Kit. Twenty five mg of frozen cancer tissue was homogenized, and then a buffer solution attached to the kit was added thereto. Further, proteinase K was added, and lysed completely at 56° C., and treated with RNase A. Then, deproteinization was carried out by buffer solution attached to the kit, and after centrifugation, the supernatant thereof was extracted and purified by a spin column attached to the kit. Using 25 ng of the obtained product as a template material of the PCR, and using AccuPrime Taq Polymerase System (PCR reaction kit, manufactured by Invitrogen Corp.), the PCR reaction was carried out.

That is, firstly, according to the product protocol attached to kit, and using 0.5 µL of each 10 µM primers (KRAS-Fw: aaggcctgctgaaaatgactg [SEQ ID NO: 16] and KRAS-Rv: ggtcctgcaccagtaatatgca [SEQ ID NO: 17]), respectively, and 2.0 µL of PCR reaction buffer attached to the kit, 0.5 µL of AccuPrime Taq enzyme, and 16.5 µL of ddH$_2$O, 20 µL of reaction solution for PCR was prepared. Then, 25 ng of the human genomic DNA derived from colorectal cancer patient was added and suspended in 20 µL of the reaction solution for PCR, and used it as a sample for PCR. Employing this sample for PCR, and using the DNA Thermal Cycler of MJ Research Inc. (DNA Engine PTC200), 36 cycles of PCR reaction were carried out under the following reaction condition.

PCR reaction conditions:
Heat denaturation: 95° C., 15 seconds
Annealing: 55° C., 15 seconds
Polymerization reaction: 68° C., 47 seconds After the PCR reaction, using the amplified DNA purified by Millipore's Montage PCR as a sample DNA, and using a primer KRAS-Rv [ggtcctgcaccagtaatatgca; SEQ ID NO: 17] as a sequence primer, sequence determination was carried out by the same method as the above-described Synthetic Example 1 (2), and it was confirmed that there is single nucleotide substitution mutation G12W (TGG) on codon 12 of the KRAS gene. The nucleotide sequence of the obtained amplified DNA is as follows aaggcctgctgaaaatgactgaatataaacttgtggtagttggagcttg gggcgtaggcaagagtgccttgacgatacagctaattcagaatcatttt gtggacgaatatgatccaacaatagaggtaaatcttgttttaatatgca tattactggtgcaggacc (2) Preparation of LH Probe The probe was designed so that it forms a loop structure on said probe at forming hybrid with wild-type DNA and mutant-type DNA, and the following LH probe was synthesized (IN1TA9GCT):

[SEQ ID NO: 19]
aaggcctgctgaaaatgactgaatataaacttgtggtagttggagctgg tatatatatatatataggtgtaggcaagagtgccttgacgatacag It should be noted that, when said probe is used, the hybrid with wild-type DNA forms loop structure with atatatatatatata, and at forming the hybrid with mutant-type DNA, the loop structure is formed with ggtatatatatatatata.

(3) LH Reaction of Human Genomic DNA Derived from Colorectal Cancer Patient

The LH probe (ID.=IN1TA9GCT [SEQ ID NO: 19]) was added to 4.5 µL of the PCR reaction product obtained in the above-described (1) so that it provides a final concentration of 200 nM, and then using the DNA Thermal Cycler (DNA Engine PTC200, manufactured by MJ Research, Inc.), 1 cycle of the reaction was carried out at the following reaction condition.

LH-reaction
PCR reaction product 4.5 µL
LH probe 0.5 µL (2 µM)
105° C. hot lid
95° C. 2 minutes
55° C. 0 to 30 seconds
68° C. 4 minutes
4° C. stop the reaction (4) Electrophoretic Separation/Detection of the LH Reaction Product in the Coexistence of Intercalator (Microchip Electrophoresis)

The reaction product obtained in the above-described (3) was subjected to the microchip electrophoretic method using the Agilent 2100 Bioanalyzer systems (Agilent Technologies Inc.). In the present electrophoretic method, Agilent DNA1000 Assay kit (produced by Agilent Technologies Inc.) which is a dedicated reagent was used, and 1.0 µL of each reaction products was applied. Here, at the time of separation/detection of the LH reaction product, since an intercalator dye and a polymer for electrophoresis attached to the kit were used in a premixed state, the LH reaction products are separated and detected in the coexisting state with intercalator during the electrophoresis process.

For the peak analysis after electrophoresis, using the system attached Agilent 2100 Expert software, wave analysis and calculation of peak mobility were carried out.

Figure 22A:
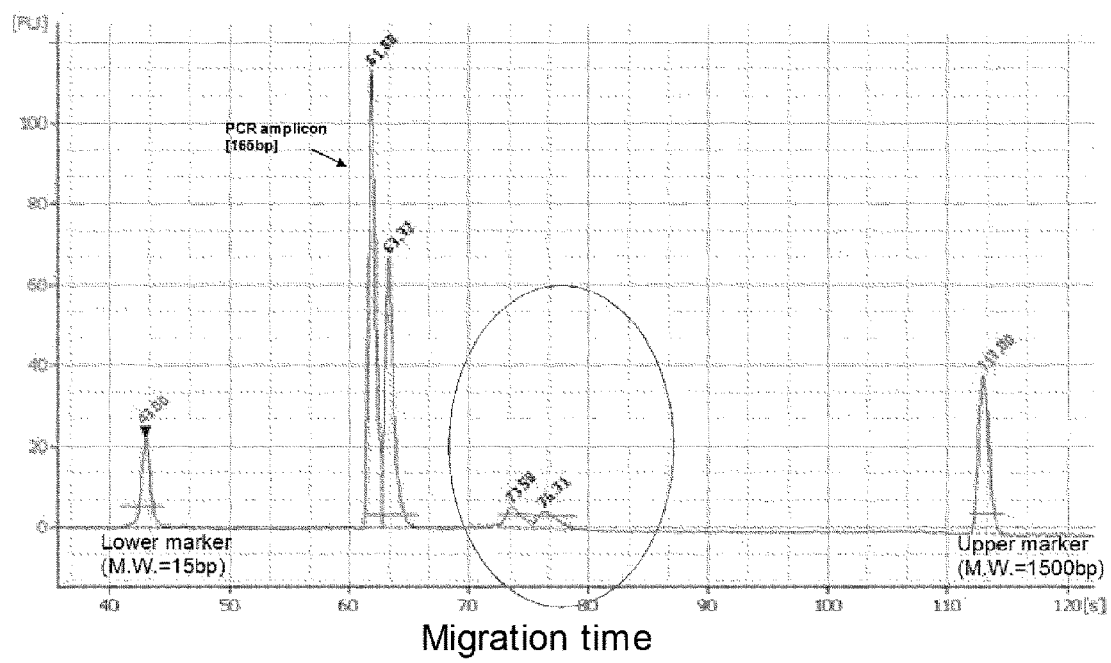
FIG. 22 is the result of separation and analysis carried out by microchip electrophoresis for the LH reaction product obtained using a wild-type DNA (WT) and a mutant-type DNA (G12W) in KRAS gene, in the coexistence of intercalator, in Example 2.
Figure 22B:
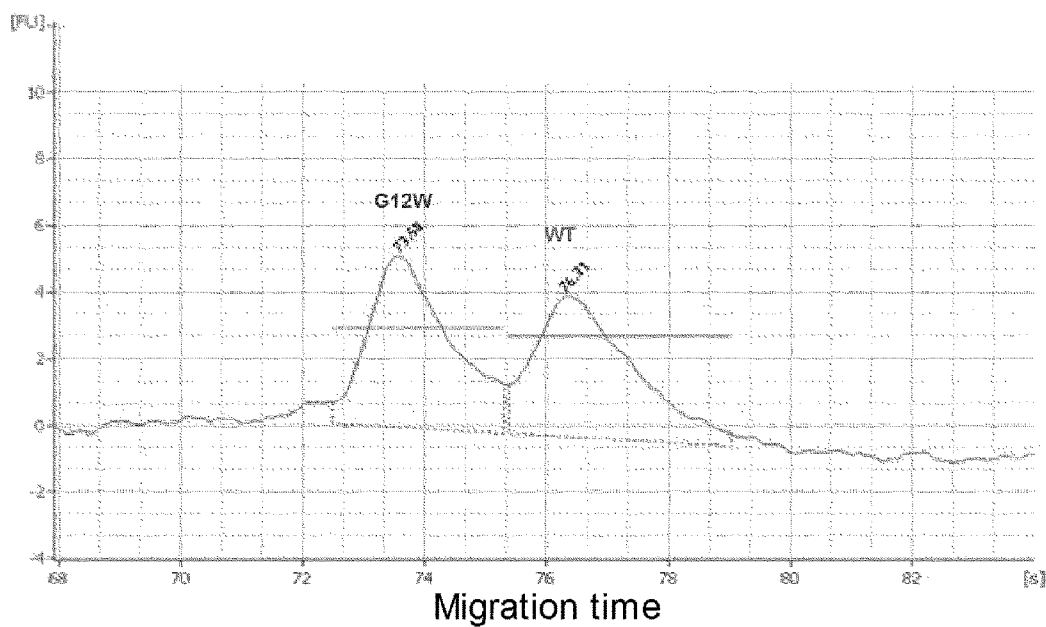

The results thereof are shown in FIG. 22A and FIG. 22B. It should be noted that FIG. 22B is an enlarged view of moiety surrounded by ○ in FIG. 22A.

Comparative Example 5: Separation/Detection about LH Reaction Products Derived from Single Nucleotide Substitution Mutant-Type DNA of KRAS Gene in the Absence of Intercalator As a comparison of Example 2, separation/detection by electrophoresis was carried about the one in which the LH reaction product was fluorescently labeled with Cy5

(1) Preparation of a Cy5-Labeled LH Probe

The probe sequence for LH reaction used in Example 2 (2); the one in which 5' terminal of IN1TA9GCT [SEQ ID NO: 19] was fluorescently labeled with Cy5, was prepared.

(2) Detection of LH Reaction Products Using a Fluorescent Signal by the Cy5-Labeled LH Probe as an Indicator Using human genomic DNA derived from a colorectal cancer patient prepared in the above-described Synthetic Example 2 as a sample, LH reaction was carried out by the same method as Example 2 (3) except for using the above-described probe. Using the obtained LH reaction products, detection of single nucleotide substitution mutant-type DNA of KRAS gene was carried out. Specifically, the LH reaction product was subjected to the microchip electrophoretic method using the Agilent 2100 Bioanalyzer systems (Agilent Technologies Inc.) in the same way as above described (3) except for using the polymer for electrophoresis and the buffer for electrophoresis as described below. As for the polymer for electrophoresis, the one in which the intercalator dye was not added, but Cy5-dCTP (GE Biosciences Corp.), which was necessary for focus adjustment in the optical system of the microchip electrophoresis, was added so that it provides final concentration of 4.9 nM, was used. As for the electrophoresis buffer, the one in which the Cy5-dCTP was added so that it provides final concentration of 4.9 nM in the same manner as in the polymer for electrophoresis. In addition, instead of DNA fragments of 15 bp (low molecular weight marker) and 1500 bp (high molecular weight marker), which have been included for the purpose of a correction of the peak mobility calculation of the electrophoresis, Cy5-labeled DNA fragments of 15 bp and 1500 bp were used, and they were added to the electrophoresis buffer. Therefore, in said electrophoresis, separation/detection is performed without coexistence with the intercalator which binds to the LH reaction products and its double-stranded DNA.

Figure 23A:
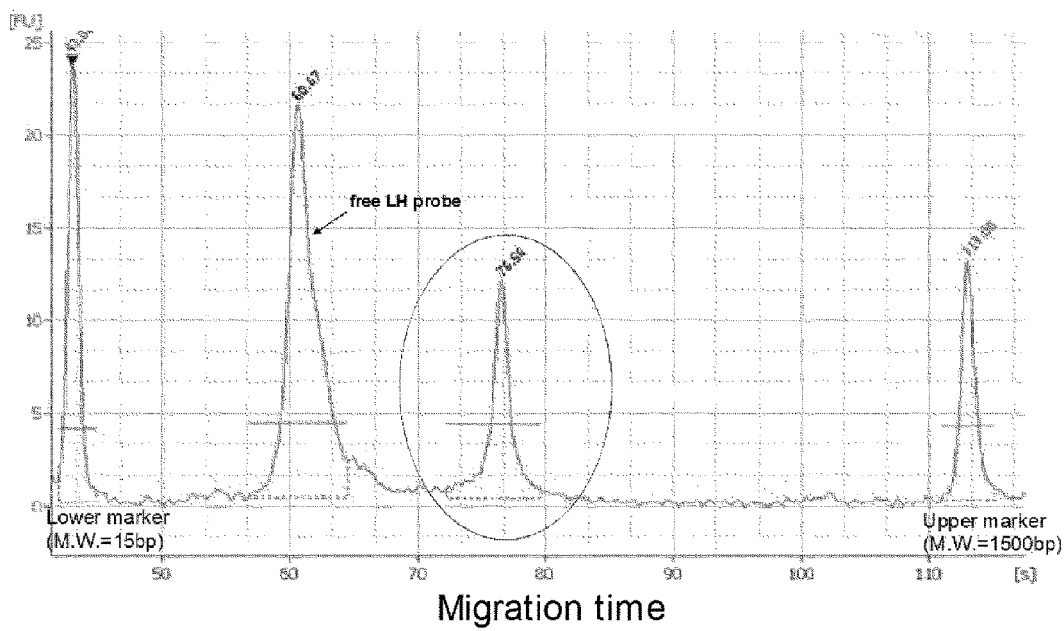
FIG. 23 is the result of separation and analysis carried out by microchip electrophoresis for the LH reaction product obtained using a wild-type DNA (WT) and a mutant-type DNA (G12W) in KRAS gene, in the absence of intercalator, in Comparative Example 5.
Figure 23B:
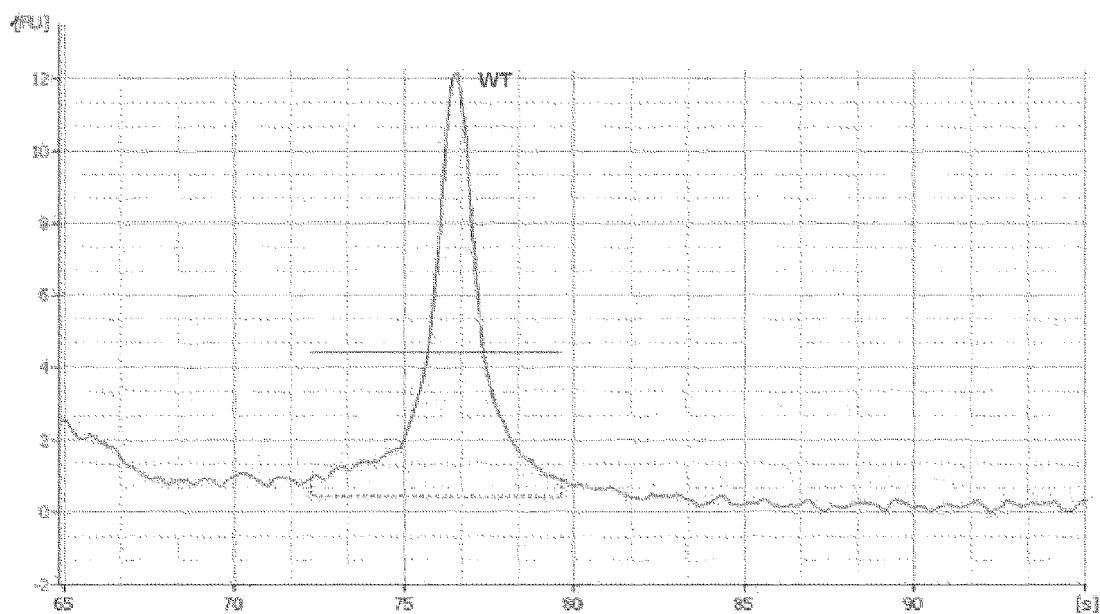

The results are shown in FIG. 23A and FIG. 23B. It should be noted that, FIG. 23B is an enlarged view of part surrounded by ○ in FIG. 23A.

As is clear from the results of FIGS. 22A-22B and FIGS. 23A-23B, it turned out that even in the case that the KRAS gene was used, similarly to the results obtained with EGFR, the single nucleotide substitution mutation G12V on the KRAS gene and wild-type DNA which could not be separated by the electrophoretic separation of the LH reaction products in the absence of the intercalator (FIGS. 23A-23B), were separated clearly and able to discriminate/detect when the electrophoretic separation was carried out in the coexistence of the intercalator (FIGS. 22A-22B).

That is, it turned out that, in the electrophoretic separation of the hybrid formed with double-stranded DNA and single-stranded DNA which are LH reaction product, by forming a bound substance of the LH reaction products and the intercalator in the presence of the intercalator and separating it, the separation and discrimination performance is improved significantly.

Example 3: Discrimination/Detection of Single Nucleotide Substitution Mutation R132H and R132C in IDH1 Gene Sequence (Acrylamide Polymerization Gel Electrophoresis)

(1) Preparation of Primer for Mutagenesis PCR

In order to incorporate R132H (CGT>CAT) and R132C (CGT>TGT) into a target DNA artificially, 2 types of primers for mutagenesis PCR were prepared. These sequences are shown in Table below.

TABLE 4

| Name of sequence (Type of mutation) | Primer sequence for mutagenesis PCR (Underline shows the sequence complementary to the place where the single nucleotide substitution occurs) | SEQ ID NO |
| --- | --- | --- |
| IDH1m3R (R132H) | ttgccaacatgacttacttgatccccataa gcatgaTgacctatgatgataggttttac | SEQ ID NO: [20] |
| IDH1m4R (R132C) | ttgccaacatgacttacttgatccccataa gcatgacAacctatgatgataggttttac | SEQ ID NO: [21] |

(2) Preparation of Human Genomic DNA Derived from Human Blood and Mutagenesis PCR Using QIAamp DNA Blood Midi Kit (Qiagen Inc.), and according to a product protocol attached to kit, 2 mL of human whole blood was treated with proteinase K at 70° C. for 10 minutes, and then ethanol was added. Further, the obtained solution was centrifuged, and the supernatant was applied to QIAamp Midi column, thus human genomic DNA was extracted. Two sets of 1 μL (50 ng) out of 30 μL (50 ng/μL) of DNA extraction solution obtained here were prepared, and using its DNA as a template, the mutagenesis PCR reaction was carried out using the AccuPrime Taq Polymerase System (PCR reaction kit, manufactured by Invitrogen Corp.), and 2 kinds of DNA were obtained. It should be noted that, in said 2 kinds of mutagenesis PCR reaction, in one kind, IDH1F (caaatggcaccatacgaaatattc [SEQ ID NO: 22]) was used as a forward primer, and IDH1m3R in the above-described Table 4 was used as a reverse primer; in the other, IDH1F was used as a forward primer, and IDH1m4R in the above-described Table 4 was used as a reverse primer.

Specifically, according to a product protocol attached to kit, using each 1.0 μL of 10 μM reverse and forward primer and 2.0 μL of kit attached PCR reaction buffer, 0.5 μL of AccuPrime Taq enzyme and 16.5 μL of ddH$_2$O, 20.0 μL of reaction solution for PCR was prepared. Using this sample for PCR, and using DNA Thermal Cycler (DNA Engine PTC200, MJ Research Inc.), the PCR reaction was performed for 36 cycles under the following reaction conditions.

PCR reaction condition:
Heat denaturation: 95° C., 15 seconds
Annealing: 55° C., 15 seconds
Polymerization reaction: 68° C., 47 seconds (3) Amplification of Sample DNA Subsequently, each of 2 kinds of DNA obtained by the above-described mutagenesis PCR reaction was diluted 1000 times, then using 1 μL of its solution as a template of the PCR amplification, the PCR reaction was carried out using the AccuPrime Taq Polymerase System (PCR reaction kit, manufactured by Invitrogen Corp.). That is, firstly, according to the product protocol attached to kit, using 1.0 μL of each 10 μM primer solution (IDH1F: caaatggcaccatacgaaatattc [SEQ ID NO: 22] as a forward side primer and IDH1S: ttgccaacatgacttacttgatcc [SEQ ID NO: 23] as a reverse side primer), and kit attached, 2.0 μL of PCR reaction buffer, 0.5 μL of AccuPrime Taq enzyme, and 16.5 μL of ddH$_2$O, 20.0 μL of reaction solution for PCR was prepared. Using this sample for PCR, and using DNA Thermal Cycler (DNA Engine PTC200) of MJ Research Inc., the PCR reaction was performed for 30 cycles under the following reaction conditions.

PCR reaction condition:
Heat denaturation: 95° C., 15 seconds
Annealing: 55° C., 15 seconds
Polymerization reaction: 68° C., 47 seconds On the other hand, on the occasion of preparing sample DNA derived from a sequence of wild type, using 1 μL (50 ng) of the DNA extraction solution derived from human blood prepared in the above-described (2) as a template directly, the PCR reaction was carried out in the same way as the method described above.

(4) Preparation of LH Probe

The probe was designed so that it forms a loop structure on the genomic DNA of target at forming the hybrid of wild-type DNA and mutant-type DNA, and LH probe was synthesized (IDH1D7S):

[SEQ ID NO: 24]
ttgccaacatgacttacttgatccccataagcatgacgtgataggtttt
acccatccac

It should be noted that, in the following LH reaction, the one in which 5' terminal of said LH probe was fluorescently labeled with Cy5 (Amersham Biosciences Corp.), was used.

When said probe is used, the hybrid with wild-type DNA forms loop structure with tcataggt. On the other hand, at forming the hybrid with mutant-type (R132H) DNA, the loop structure is formed with tcataggtcg, and at forming the hybrid with mutant-type (R132C) DNA, the loop structure is formed with tcataggtc.

(5) LH Reaction

The LH probe (ID.=IDH1D7S) was added to each 4.5 μL of 3 kinds of the PCR reaction products obtained in the above-described (3) so that it gives final concentration of 200 nM, and then using the DNA Thermal Cycler (DNA Engine PTC200, manufactured by MJ Research, Inc.), 1 cycle of reaction was carried out under the following reaction condition.

LH-reaction
PCR reaction product 4.5 μL
LH probe 0.5 μL (2 μM)
105° C. hot lid
95° C. 2 minutes
55° C. 0 to 30 seconds 68° C. 4 minutes 4° C. stop the reaction (6) Separation/Detection of Hybrid by LH Reaction (Acrylamide Polymerization Gel Electrophoresis)

To each 1.5 µL of 3 kinds of LH reaction products (hybrid product) obtained by using LH probe in the above-described (5), 1.5 µL of gel loading buffer was added, respectively, and used this as a sample for electrophoresis. Here, in order to confirm the effects of the case where the LH reaction products and the intercalator are separated and detected in the coexisting state, the effect of additive concentration of the intercalator was investigated. Using GelRed (Wako Pure Chemical Industries, Ltd.) and Cellstain PI Solution (1 mg/mL aqueous propidium iodide solution, Dojindo Co., Ltd.) as an intercalator, respectively, the concentration of the intercalator was adjusted so as to give the final concentration of 1/100 times, 1/1000 times and 1/10000 times to the original solution and then respective experiment was carried out.

As the acrylamide polymerization gel, a 10% nondenaturing 7 cm×7 cm compact gel (Compact gel C10L, produced by ATTO Corp.) was used, and using Tris-glycine buffer solution (37.5 mM Tris and 288 mM glycine) as an electrophoresis buffer solution, electrophoresis was carried out by a small electrophoretic equipment (Compact PAGE AE-7300, produced by ATTO Corp.) at room temperature. After the electrophoresis, using a laser imaging scanner (Amersham Biosciences Corp., STORM 860), fluorescent detection of Cy5 (excitation wavelength 635 nm, detection filter 650LP) was carried out.

Figure 24:
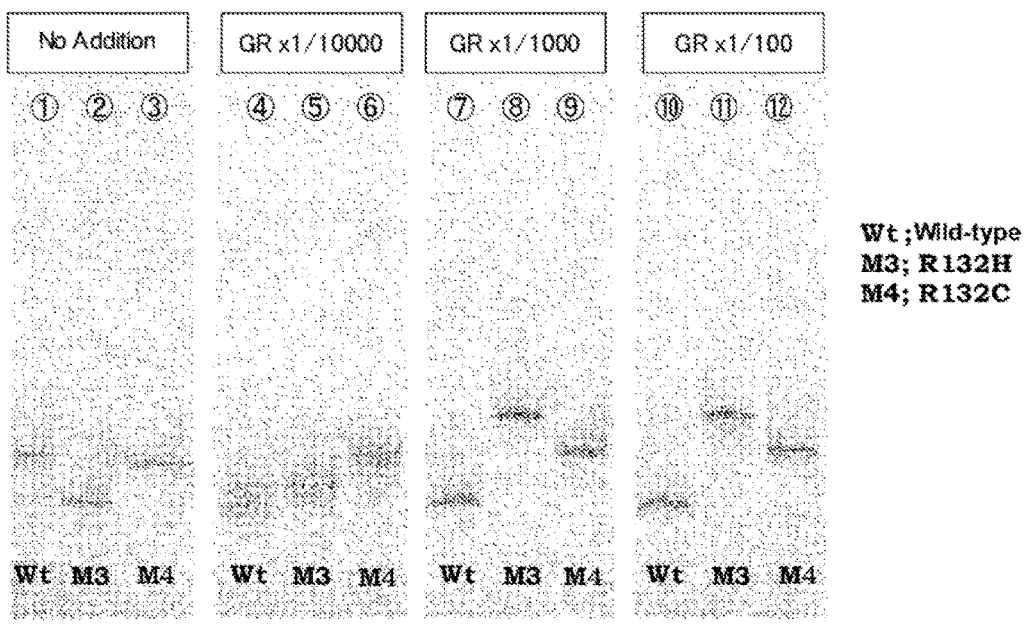
FIG. 24 is the result of separation and analysis carried out by gel electrophoresis for the LH reaction product obtained using a wild-type DNA and a mutant-type DNA in IDH1, in the coexistence and absence of intercalator, in Example 3 and Comparative Example 6.

In FIG. 24, the result obtained by using GelRed as an intercalator is shown. It should be noted that, lane 4 to 6 shows the results when the final concentration of intercalator is 1/10000, lane 7 to 9 shows the results when the final concentration of intercalator is 1/1000, and lane 10 to 12 shows the results when the final concentration of intercalator is 1/100. In addition, in each lane, Wt represents the result obtained using wild-type as measurement target; M3 represents the result obtained using R132H mutant-type as measurement target; M4 represents the result obtained using R132C mutant-type as measurement target, respectively.

Comparative Example 6: Discrimination/Detection of Single Nucleotide Substitution Mutation R132H and R132C in IDH1 Gene Sequence in the Absence of Intercalator In the separation/detection of hybrid by LH reaction of Example 3 (6), experiment was conducted in the same way as Example 3 except for not adding the intercalator into the sample for electrophoresis.

The results are shown together with the results of Example 3 in FIG. 24. It should be noted that, in the Figure, lane 1 to 3 is the result carried out without addition of the intercalator. In addition, Wt indicates the result obtained using wild-type as measurement target; M3 indicates the result obtained using R132H mutant-type as measurement target; M4 indicates the result obtained using R132C mutant-type as measurement target, respectively.

As is clear from the results of FIG. 24, in the electrophoretic separation/detection of the LH reaction products in the absence of intercalator, since the migration band position derived from the wild-type sample and R132C mutant-type overlaps, separation/detection was not possible. On the other hand, it turned out that, by coexistence of the intercalator, LH reaction products which could not be separated in the absence of the intercalator, can be separated clearly. That is, it turned out that, depending on the concentration of the intercalator, the migration band derived from wild-type sample and 2 types of mutant-type (R132H, R132C) can be discriminated/detected. In addition, although it is not shown in the Figure, also from the result of the experiment conducted in the coexistence of propidium iodide, similarly as is the case of coexistence of GelRed, it was confirmed that the separation performance of the migration band derived from sample of the wild-type and R132C mutant-type is improved.

Example 4: Discrimination/Detection of Single Nucleotide Substitution Mutation R132H and R132C in IDH1 Gene Sequence (Microchip Electrophoresis)

Three kinds of LH reaction products (hybrid products) obtained in the above-described Example 3 (5) were subjected to the microchip electrophoretic method using the Agilent 2100 Bioanalyzer systems (Agilent Technologies Inc.).

That is, Agilent DNA1000 Assay kit which is a dedicated reagent (manufactured by Agilent Technologies Inc.) was used, and 1.0 µL of each reaction product was used. As the intercalator, instead of intercalator dye attached to the kit, GelRed (Wako Pure Chemical Industries, Ltd.) or SYTO62 (Molecular Probe Inc.) was employed. It should be noted that, as for said LH probe used in the present Example, because the one, in which 5' terminal is modified fluorescently with Cy5, is prepared, as shown in Comparative Example 1 and Comparative Example 3 of the present application, detection of the LH reaction products in the microchip electrophoresis utilized the detection wavelength range of Bioanalyzer system, becomes possible. That is, as a verification experiment, it means that, the peak detection result can be obtained without being influenced by the range of fluorescent wavelength owned by the intercalator dye and the presence or absence of the addition itself. For the peak analysis after electrophoresis, using the Agilent 2100 Expert software attached to system, wave analysis and calculation of peak mobility were carried out.

Figure 25:
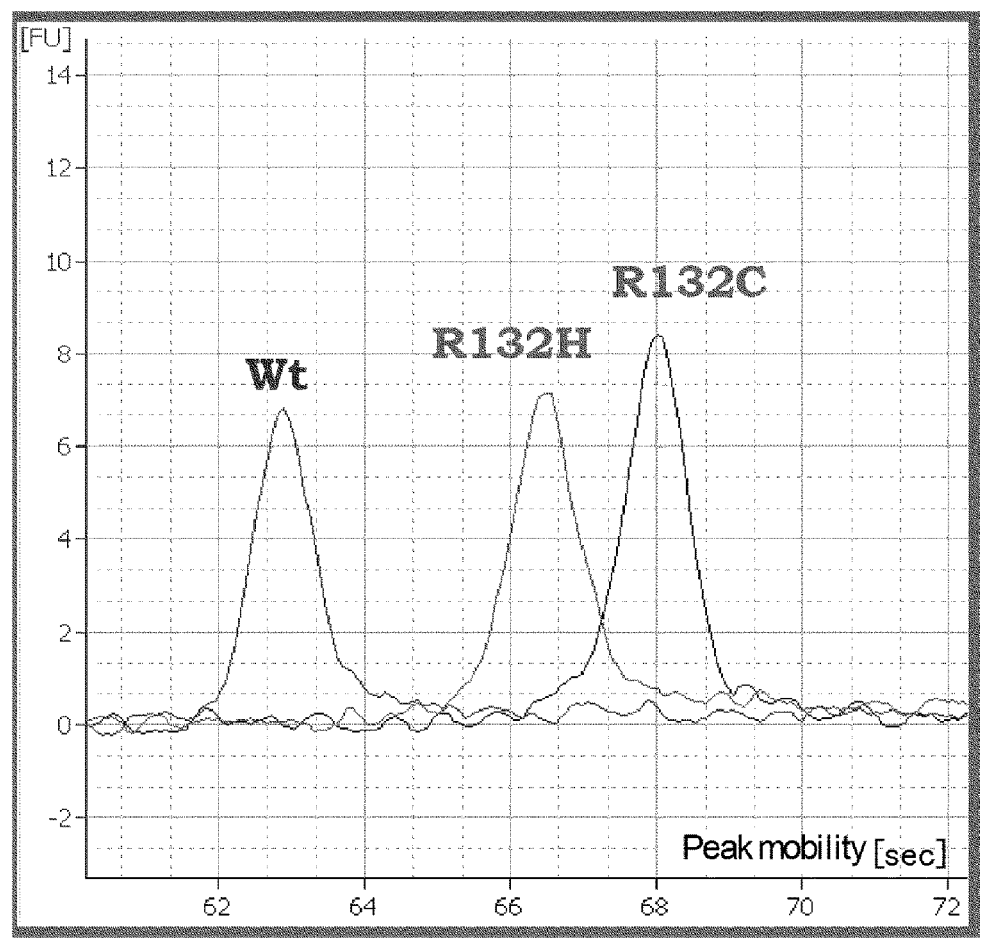
FIG. 25 is the result of separation and analysis carried out by microchip electrophoresis for the LH reaction product obtained using a wild-type DNA and a mutant-type DNA in IDH1, in the coexistence of intercalator, in Example 4.

The results when GelRed was existed as a intercalator at the final concentration of ×1/1000 are shown in FIG. 25.

Comparative Example 7: Discrimination/Detection of Single Nucleotide Substitution Mutation R132H and R132C in IDH1 Gene Sequence in the Absence of Intercalator Except for not adding the intercalator, experiment was carried out in the same manner as in Example 4. The results are shown in FIG. 26.

Figure 26:
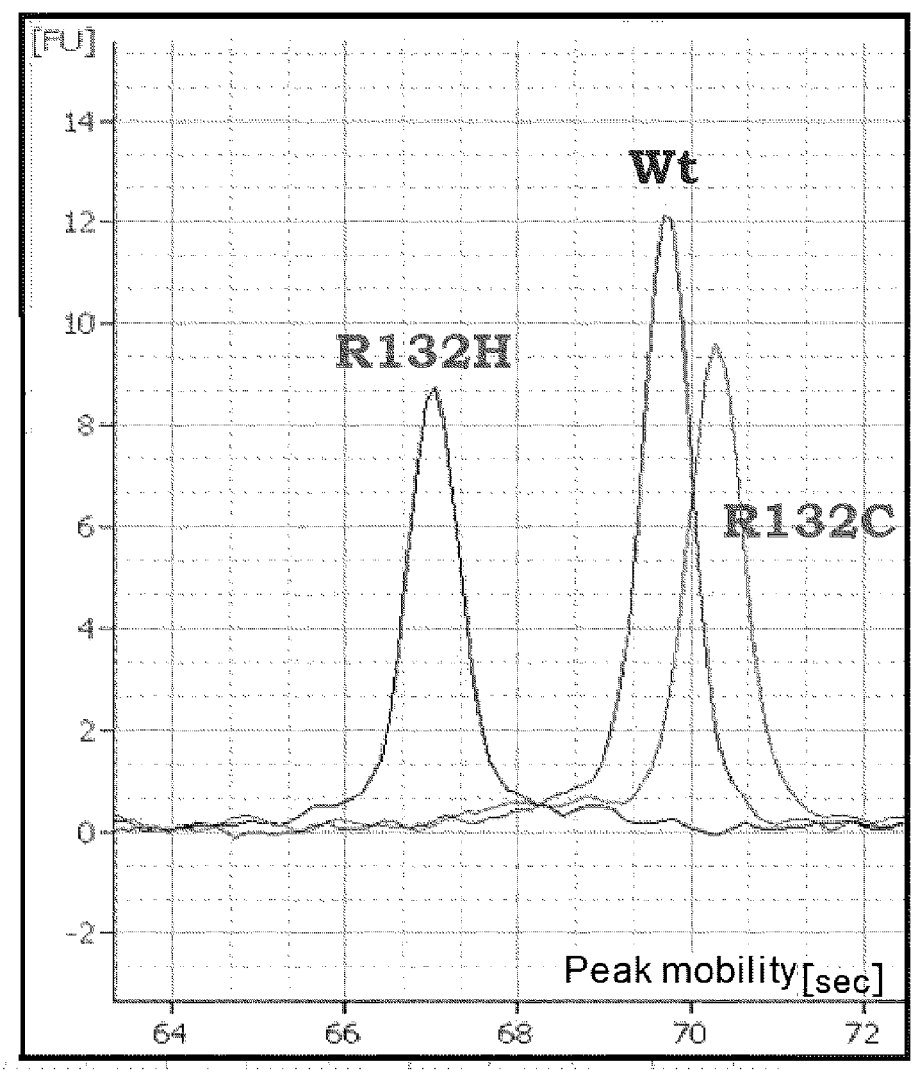
FIG. 26 is the result of separation and analysis carried out by microchip electrophoresis for the LH reaction product obtained using a wild-type DNA and a mutant-type DNA in IDH1, in the absence of intercalator, in Comparative Example 7.

As shown the results in FIG. 26, in the electrophoretic separation/detection of the LH reaction products in the absence of intercalator, since the migration band position derived from the wild-type sample (Wt) and R132C mutant-type sample overlaps, separation/detection was not possible. On the other hand, it turned out that, in FIG. 25 of the results of the experiment conducted in the coexistence of GelRed, the LH reaction products which could not be separated in the absence of the GelRed, can be separated clearly. In addition, although it is not shown in the Figure, also in the result of the experiment conducted in the coexistence of SYTO62, as is the case with GelRed, 3 DNAs could be separated/detected without overlapping of their bands position. That is, it turned out that, by using the intercalator, the separation accuracy is improved, and the migration band derived from wild-type DNA (Wt) and the migration band derived from 2 types of mutant-type DNA (R132H, R132C) can be discriminated/detected.

Example 5, Comparative Example 8: Discrimination/Detection of Single Nucleotide Substitution Polymorphism of ALDH 2 Gene Sequence (Acrylamide Polymerization Gel Electrophoresis)

(1) Preparation of Human Genomic DNA Derived from Human Blood Including ALDH 2 Gene Polymorphism Using QIAamp DNA Blood Midi Kit (Qiagen Inc.), and according product protocol attached to kit, 2 mL of human whole blood was treated with proteinase K at 70° C. for 10 minutes, and then ethanol was added. Further, the obtained solution was centrifuged, and its supernatant was subjected to QIAamp Midi column, and thus human genomic DNA was extracted. Next, using 50 ng of the obtained DNA extraction solution as a template material of the PCR, the PCR reaction was carried out using the AccuPrime Taq Polymerase System (PCR reaction kit, manufactured by Invitrogen Corp.).

That is, firstly, according to a product protocol attached to kit, using 0.5 µL of each 10 µM primer solutions (ALDHF; ggtcaactgctatgatgtgtttg [SEQ ID NO: 25] and ALDHR; cagcaggtcccacactcac [SEQ ID NO: 26]), respectively, and 2.0 µL of PCR reaction buffer attached to kit, 0.5 µL of AccuPrime Taq enzyme and 16.5 µL of ddH$_2$O, 20.0 µL of reaction solution for PCR was prepared. After that, 50 ng of human genomic DNA obtained in the above was added and suspended in the 20 µL of reaction solution for PCR, and used as sample for PCR. Using this sample for PCR, and using DNA Thermal Cycler (DNA Engine PTC200, MJ Research Inc.), the PCR reaction was carried out for 36 cycles under the following reaction conditions.

PCR reaction condition:
Heat denaturation: 95° C., 15 seconds
Annealing: 55° C., 15 seconds
Polymerization reaction: 68° C., 47 seconds After the PCR reaction, using the amplified DNA which has been purified by Millipore's Montage PCR as a sample DNA, and using a primer ALDHF [ggtcaactgctatgatgtgtttg; SEQ ID NO: 25] as a sequence primer, sequence confirmation was carried out by the same method as the above-described Synthetic Example 1 (2). From them, 3 kinds of specimen of homo of ALDH2*2 polymorphism in which 504th amino acid has been substituted from glutamic acid (GAA) to lysine (AAA), as well as hetero of wild-type DNA and ALDH2*2 polymorphism, and homo of wild-type DNA were obtained, and used them as a sample.

(2) Preparation of LH Probe

The probe was designed so that it forms a loop structure on genomic DNA to be a target at forming the hybrid with wild-type DNA and the hybrid with DNA having ALDH2*2 polymorphism, and the following LH probe was synthesized (ALDH2D13R):

[SEQ ID NO: 27]
cagcaggtcccacactcacagtttcacttcagcccgtactcgcccaac tcccg

It should be noted that, in the following LH reaction, the one in which 5' terminal of said LH probe was fluorescently labeled with Cy5 (Amersham Biosciences Corp.), was used.

When said probe is used, the hybrid with wild-type DNA forms loop structure with gcaggcatacact. On the other hand, at forming the hybrid with DNA having ALDH2*2 polymorphism, the loop structure is formed with gcaggcatacactg.

(3) LH Reaction

The LH probe (ID.=ALDH2D13R) was added to each 4.5 µL of 3 kinds of the PCR reaction products obtained in the above-described (2) so that it gives final concentration of 200 nM, and then using the DNA Thermal Cycler (DNA Engine PTC200, manufactured by MJ Research, Inc.), 1 cycle of reaction was carried out under the following reaction condition.

LH-reaction
PCR reaction product 4.5 µL
LH probe 0.5 µL (2 µM)
105° C. hot lid
95° C. 2 minutes
55° C. 0 to 30 seconds
68° C. 4 minutes
4° C. stop the reaction (4) Separation/Detection of Hybrid by LH Reaction (Acrylamide Polymerization Gel Electrophoresis)

To each 1.5 µL of sample of homo among the LH reaction products (hybrid product) obtained in the above-described (3), 1.5 µL of gel loading buffer was added, respectively, and used this as a sample for electrophoresis. Here, in order to confirm the effects of the case where the LH reaction products and the intercalator are separated/detected in the coexisting state, using GelRed (Wako Pure Chemical Industries, Ltd.) or SYBR Green (Molecular Probes Inc.) as an intercalator, and adding it to the above-described sample for electrophoresis so that it provides final concentration of ×1/1000, respectively, the experiment was carried out.

In addition, on the other hand, as a comparative experiment, separation/detection of the LH reaction product in the absence of intercalator was carried out in parallel (Comparative Example 8).

As the acrylamide polymerization gel, a 10% nondenaturing 7 cm×7 cm compact gel (Compact gel C10L, produced by ATTO Corp.) was used, and using Tris-glycine buffer solution (37.5 mM Tris and 288 mM glycine) as an electrophoresis buffer solution, electrophoresis was carried out by a small electrophoretic equipment (Compact PAGE AE-7300, produced by ATTO Corp.) at room temperature. After the electrophoresis, using a laser imaging scanner (Amersham Biosciences Corp., STORM 860), Cy5 fluorescent detection (excitation wavelength 635 nm, detection filter 650LP) was performed.

Figure 27:
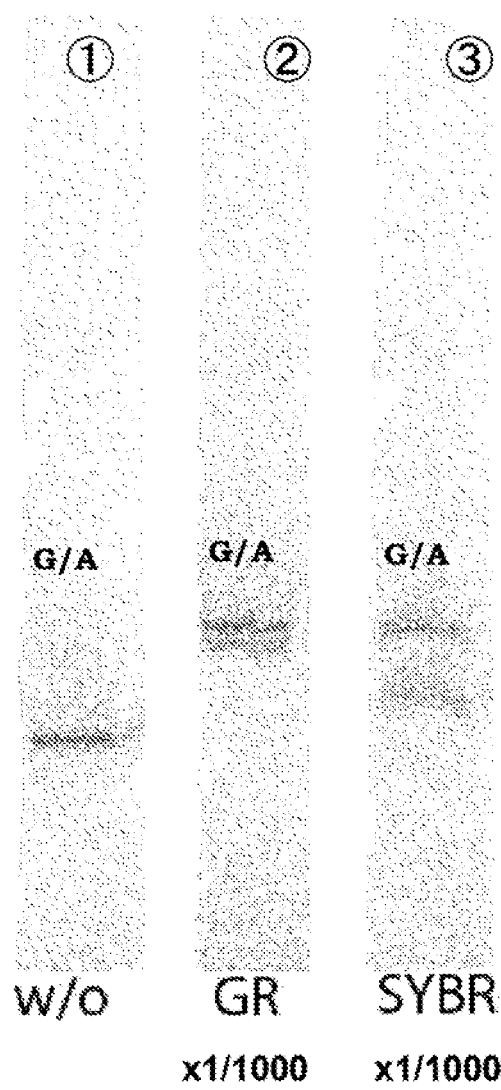
FIG. 27 is the result of separation and analysis carried out by gel electrophoresis for the LH reaction product obtained using a wild-type DNA and a mutant-type DNA in ALDH2 gene, in the coexistence or absence of intercalator, in Example 5 and Comparative Example 8.

The obtained results are shown in FIG. 27. It should be noted that, lane 1 shows the results of experiment carried out in the absence of intercalator; lane 2 shows the results of experiment carried out in the coexistence of GelRed at 1/1000 final concentration; and lane 3 shows the results of experiment carried out in the coexistence of SYBR Green at 1/1000 final concentration.

As is clear from the results of FIG. 27, in the electrophoretic separation/detection of the LH reaction products in the absence of intercalator, since the migration band position derived from wild-type [G] and ALDH2*2 polymorphism [A] overlaps, separation/detection was not possible. On the other hand, it turned out that, by coexistence of the intercalator, LH reaction products which could not be separated in the absence of the intercalator can be separated clearly. Furthermore, since the separation performance was improved significantly in the coexistence of SYBR Green as compared to the coexistence of GelRed, it was suggested that the separation can be performed more effectively by selecting the intercalator.

Example 6, Comparative Example 9:
Discrimination/Detection of Single Nucleotide Substitution Polymorphism of ALDH 2 Gene Sequence (Microchip Electrophoresis)

Three kinds of LH reaction products (hybrid products) obtained in the above-described Example 5 (3) were subjected to the microchip electrophoretic method using the Agilent 2100 Bioanalyzer systems (Agilent Technologies Inc.).

That is, Agilent DNA1000 Assay kit which is a dedicated reagent (manufactured by Agilent Technologies Inc.) was used, and 1.0 μL of each reaction product was used. As the intercalator, the intercalator dye attached to kit or GelRed (Wako Pure Chemical Industries, Ltd.) was used. Both were used after pre-mixed with the polymer for electrophoresis.

On the other hand, in order to carry out a comparative experiment with these tests, according to the similar procedure that was carried out in Comparative Example 1 and Comparative Example 7 in the present application, the separation/detection of LH reaction products in the absence of intercalator was carried out. It should be noted that, as for the LH probe to be used in this Example, since the one labeled fluorescently 5' terminal with Cy5 is prepared, detection of the LH reaction products in the microchip electrophoresis utilized detection wavelength range of Bioanalyzer system becomes possible. That is, it means that, as a verification experiment, the peak detection result can be obtained without being influenced by the range of fluorescent wavelength owned by the intercalator dye and the presence or absence of addition.

For the peak analysis after electrophoresis, using the Agilent 2100 Expert software attached to system, wave analysis and peak mobility FIG. 28 were calculated.

Figure 28A:
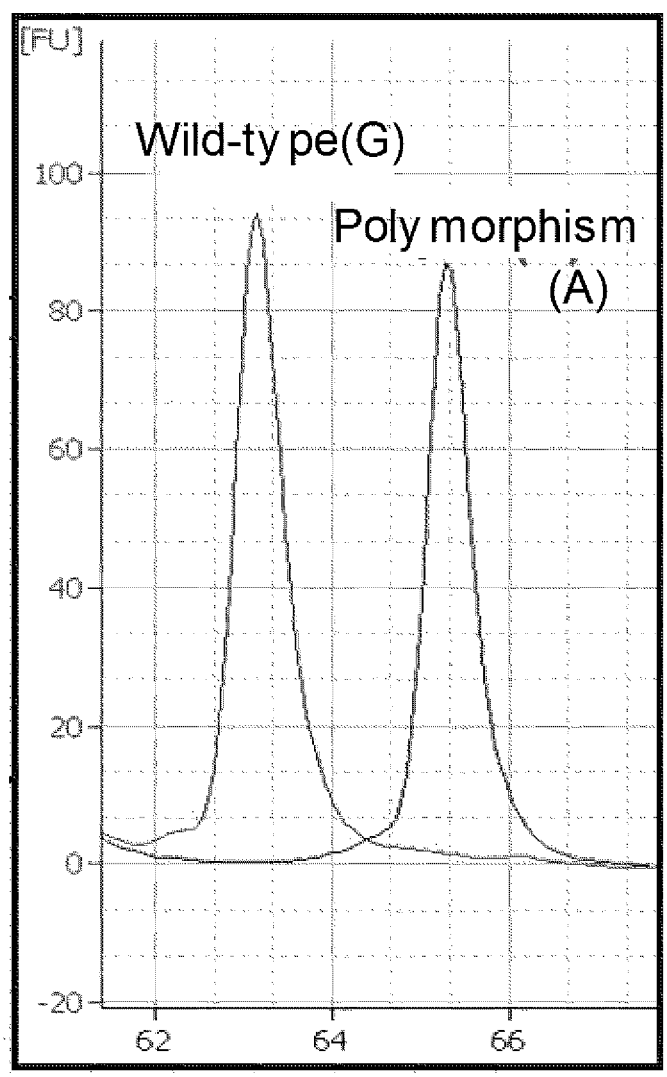
FIG. 28 is the result of separation and analysis carried out by microchip electrophoresis for the LH reaction product obtained using a wild-type DNA and a mutant-type DNA in ALDH2 gene, in the coexistence or absence of intercalator, in Example 6 and Comparative Example 9.
Figure 28B:
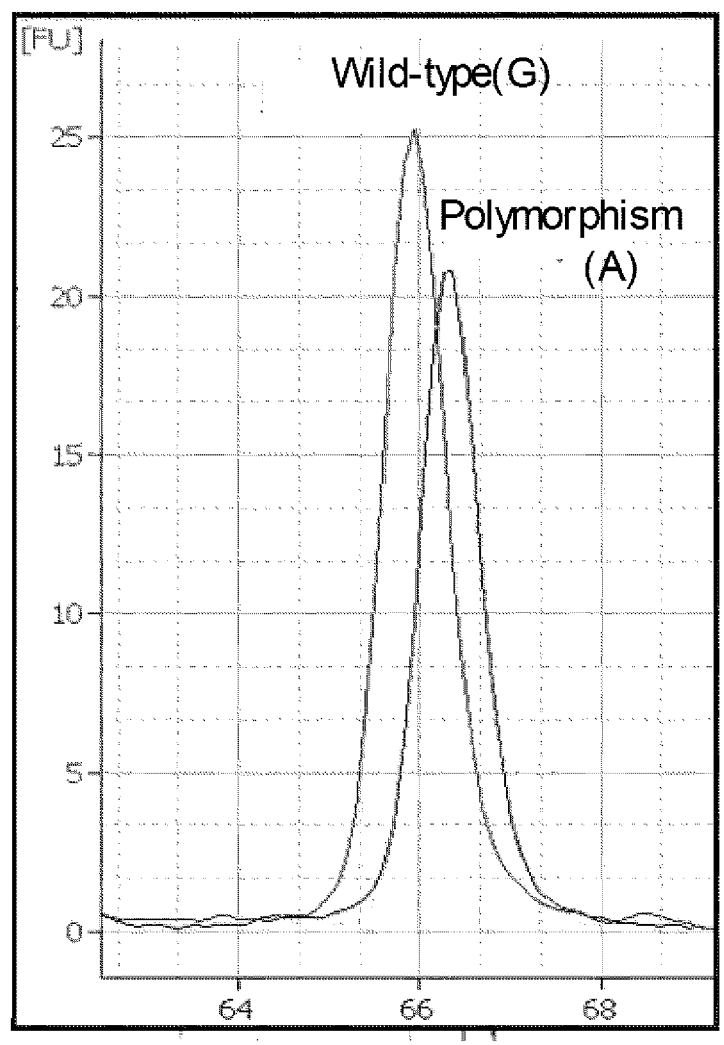
Figure 28C:
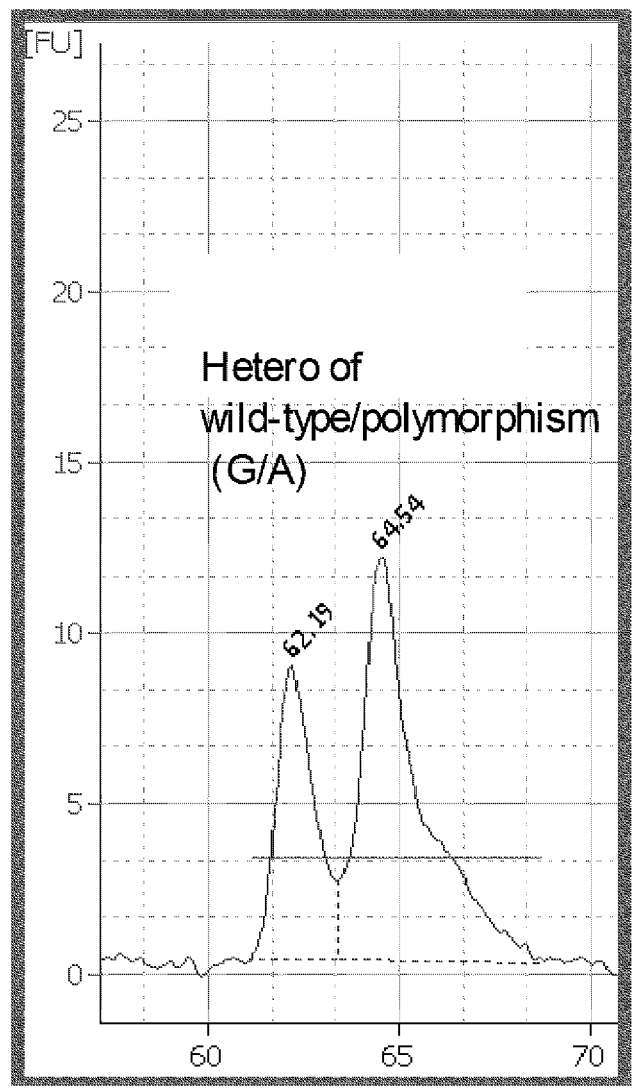

The results are shown in FIGS. 28A, 28B, and 28C. In FIGS. 28A and 28B, the migration peak obtained by measuring 2 kinds of sample of homo of wild-type DNA and homo of ALDH2*2 polymorphism, respectively, is shown in piles. The FIG. 28A is an experiment in the coexistence of intercalator Dye attached to kit, FIG. 28B is a result in the absence of intercalator (Comparative Example 9). FIG. 28C is a result of experiment in which hetero-type sample of wild type DNA and ALDH2*2 polymorphism was measured by carrying out in the coexistence of GelRed as an intercalator at a final concentration of ×1/1000.

As the results shown in FIG. 28B, in the electrophoretic separation/detection of the LH reaction products in the absence of intercalator, since the each migration band position derived from wild-type [G] and ALDH2*2 polymorphism [A] overlaps, separation/detection was not possible. On the other hand, it turned out that, in FIG. 28A or FIG. 28C carried out the verification by coexistence of the intercalator, the LH reaction products which could not be separated in the absence of the intercalator can be separated clearly. That is, it turned out that the migration band derived from wild-type [G] and the migration band derived from ALDH2*2 polymorphism [A] can be discriminatively detected.

Example 7: Separation/Detection of LH Reaction Products, in which the Mutant-Type DNA on EGFR Gene Exon 19 was Set as a Measurement Target, in the Coexistence of Intercalator (Acrylamide Polymerization Gel Electrophoresis)

On the basis of the results obtained in Comparative Example 3, the effect of the case where the separation/detection of LH reaction products is carried out in a state that the LH reaction products is coexisted with intercalator in the course of acrylamide polymerization gel electrophoresis, was confirmed.

Specifically, using 6 kinds of LH reaction products obtained by the LH reaction in Example 1 (2), the electrophoresis was carried out as described below. Firstly, to each 1.5 μL of 6 kinds of samples, 1.5 μL of gel loading buffer was added respectively, and used it as a sample for electrophoresis. GelRed (Wako Pure Chemical Industries Ltd.) was employed as intercalator, and added it to the above-described sample for electrophoresis so as to give a final concentration of ×1/1000, and its effect was investigated.

As the acrylamide polymerization gel for electrophoresis, a 10% nondenaturing 7 cm×7 cm compact gel (Compact gel C10L, produced by ATTO Corp.) was used, and using Tris-glycine buffer solution (37.5 mM Tris and 288 mM glycine) as an electrophoresis buffer solution, electrophoresis was carried out by a small electrophoretic equipment (Compact PAGE AE-7300, produced by ATTO Corp.) at room temperature. After the electrophoresis, using a laser imaging scanner (Amersham Biosciences Corp., STORM 860), Cy5fluorescent detection (excitation wavelength 635 nm, detection filter 650LP) was carried out.

Figure 29:
FIG. 29 is the result of separation and analysis carried out by gel electrophoresis for a sample prepared by adding intercalator to the LH reaction product obtained using a wild-type DNA (N) and a mutant-type DNA (G1 to G5) in EGFR gene, in Example 7.

Thus obtained results are shown in FIG. 29. It should be noted that, in the Figure, lane 1 shows the result of using mutant-type DNA (G1), lane 2 shows the result of using mutant-type DNA (G2), lane 3 shows the result of using mutant-type DNA (G3), lane 4 shows the result of using mutant-type DNA (G4), lane 5 shows the result of using mutant-type DNA (G5), and lane 6 shows the result of using wild-type DNA (N), respectively.

From the result shown in FIG. 29, with respect to the migration band derived from sample clones of G1 to G5 which were difficult to separate and detect completely in Comparative Example 3, the effect of the present invention was confirmed, and at the same time it was shown that complete separation and detection of respective mutant-type has become possible. In particular, it is significant that the separation performance in the mutant-type DNA (G2), mutant-type DNA (G3), mutant-type DNA (G5) which were indicated by arrow (→) was improved.

The invention claimed is:

1. A method for detecting mutant-type DNA or/and wild-type DNA in a sample comprising the following steps (1) to (4):
   (1) hybridizing a mutant single-stranded DNA with a probe to form a mutant-type hybrid, or/and hybridizing a wild-type single-stranded DNA with the probe to form a wild-type hybrid, wherein at least one of the mutant-type hybrid and the wild-type hybrid has a loop structure, and wherein the mutant single-stranded DNA has a different nucleotide sequence than the wild-type single-stranded DNA,
   (2) contacting the mutant-type hybrid or/and the wild-type hybrid obtained in step (1) with an intercalator to form a mutant-type hybrid and intercalator conjugate or/and a wild-type hybrid and intercalator conjugate,
   (3) separating the conjugate of mutant-type hybrid and intercalator or/and the conjugate of wild-type hybrid and intercalator from the sample, wherein the method for separating the conjugate of mutant-type hybrid and intercalator or/and the conjugate of wild-type hybrid and intercalator is an electrophoretic method, and
   (4) detecting the presence or absence of the separated conjugate of mutant-type hybrid and intercalator or/and the separated conjugate wild-type hybrid and intercalator as determinative of the presence or absence of the mutant-type DNA or/and the wild-type DNA.

2. The method according to claim 1, wherein the probe has a nucleotide that does not allow the probe to perfectly complement the mutant single-stranded DNA, thereby forming the loop structure or/and the probe has a nucleotide that does not allow the probe to perfectly complement the wild-type single-stranded DNA, thereby forming the loop structure.

3. The method according to claim 1, wherein the loop structure further comprises a stem structure.

4. The method according to claim 1, wherein the intercalator is selected from the group of an acridine dye, an ethidium compound, an iodine compound, 7-aminoactinomycin D (7-AAD), a cyanine dimer dye, a cyanine monomer dye, a dye that binds to the minor groove of a DNA double helix, and a dye that binds to an adenine-thymine sequence.

5. The method according to claim 1, wherein the conjugate of mutant-type hybrid and intercalator or/and the conjugate of wild-type hybrid and intercalator is separated based on a difference of molecular weight, molecular structure, or electric charge.

6. The method according to claim 1, wherein the probe perfectly complements a portion of the mutant single-stranded DNA over the entire length of the probe, which portion of the mutant single-stranded DNA has a nucleotide sequence that differs from that of the corresponding portion of the wild-type single-stranded DNA by containing one or more additional nucleotides, such that the wild-type hybrid has a loop structure.

7. The method according to claim 1, wherein the probe perfectly complements a portion of the mutant single-stranded DNA over the entire length of the probe, which portion of the mutant single-stranded DNA has a nucleotide sequence that differs from that of the corresponding portion of the wild-type single-stranded DNA by containing one or more fewer nucleotides, such that the wild-type hybrid has a loop structure.

8. The method according to claim 1, wherein the probe perfectly complements a portion of the wild-type single-stranded DNA over the entire length of the probe, which portion of the wild-type single-stranded DNA has a nucleotide sequence that differs from that of the corresponding portion of the mutant single-stranded DNA by containing one or more additional nucleotides, such that the mutant-type hybrid has a loop structure.

9. The method according to claim 1, wherein the probe perfectly complements a portion of the wild-type single-stranded DNA over the entire length of the probe, which portion of the wild-type single-stranded DNA has a nucleotide sequence that differs from that of the corresponding portion of the mutant single-stranded DNA by containing one or more fewer nucleotides, such that the mutant-type hybrid has a loop structure.

10. The method according to claim 1, wherein the probe does not perfectly complement a portion of the wild-type single-stranded DNA or a portion of the mutant single-stranded DNA over the entire length of the probe, and wherein the wild-type single-stranded DNA has one or more nucleotides that differ from corresponding nucleotides of the mutant single-stranded DNA, such that the wild-type hybrid has a loop structure and the mutant-type hybrid has a loop structure.

11. A method for detecting the presence or absence of a mutation in an epidermal growth factor receptor (EGFR) gene in a sample comprising the following steps (1) to (4):
(1) hybridizing a mutant single-stranded EGFR gene with a probe to form a mutant-type hybrid or/and hybridizing a wild-type single-stranded EGFR with the probe to form a wild-type hybrid,
wherein at least one of the mutant-type hybrid and the wild-type hybrid has a loop structure, and
wherein the mutant single-stranded DNA has a different nucleotide sequence than the wild-type single stranded DNA,
(2) contacting the mutant-type hybrid or/and the wild-type hybrid obtained in step (1) with an intercalator, to form a mutant-type hybrid and intercalator conjugate or/and a wild-type hybrid and intercalator conjugate,
(3) separating the conjugate of mutant-type hybrid and intercalator or/and the conjugate of wild-type hybrid and intercalator from the sample, wherein the method for separating the conjugate of mutant-type hybrid and intercalator or/and the conjugate of wild-type hybrid and intercalator is an electrophoretic method, and
(4) detecting the presence or absence of the separated conjugate of mutant-type hybrid and intercalator or/and the separated conjugate of wild-type hybrid and intercalator as determinative of the presence or absence of the mutant-type EGFR or/and the wild-type EGFR.

12. The method according to claim 11, wherein the probe has a nucleotide that does not allow the probe to perfectly complement the mutant single-stranded EGFR, thereby forming the loop structure or/and the probe has a nucleotide that does not allow the probe to perfectly complement the wild-type single-stranded EGFR, thereby forming the loop.

13. The method according to claim 12, wherein the probe comprises the nucleotide sequence of SEQ ID NO: 15.

14. A method for detecting the presence or absence of a mutation in a kirsten rat sarcoma viral oncogene (KRAS) gene in a sample comprising the following steps (1) to (4):
(1) hybridizing a mutant single-stranded KRAS gene with a probe to form a mutant-type hybrid or/and hybridizing a wild-type single-stranded KRAS with the probe to form a wild-type hybrid, wherein at least one of the mutant-type hybrid and the wild-type hybrid has a loop structure, and wherein the mutant single-stranded DNA has a different nucleotide sequence than the wild-type single stranded DNA,
(2) contacting the mutant-type hybrid or/and the wild-type hybrid obtained in step (1) with an intercalator, to form a mutant-type hybrid and intercalator conjugate or/and a wild-type hybrid and intercalator conjugate,
(3) separating the conjugate of mutant-type hybrid and intercalator or/and the conjugate of wild-type hybrid and intercalator from the sample, wherein the method for separating the conjugate of mutant-type hybrid and intercalator or/and the conjugate of wild-type hybrid and intercalator is an electrophoretic method, and
(4) detecting the presence or absence of the separated conjugate of mutant-type hybrid and intercalator or/and the separated conjugate of wild-type hybrid and intercalator as determinative of the mutant-type KRAS or/and the wild-type KRAS.

15. The method according to claim 14, wherein the probe has a nucleotide that does not allow the probe to perfectly complement the mutant single-stranded KRAS, thereby forming the loop structure or/and the probe has a nucleotide that does not allow the probe to perfectly complement the wild-type single-stranded KRAS, thereby forming the loop.

16. The method according to claim 15, wherein the probe comprises the nucleotide sequence of SEQ ID NO: 19.

* * * * *

UNITED STATES PATENT AND TRADEMARK OFFICE
CERTIFICATE OF CORRECTION

PATENT NO. : 9,932,625 B2  
APPLICATION NO. : 14/387150  
DATED : April 3, 2018  
INVENTOR(S) : Shoichi Matsukuma et al.

Page 1 of 1

It is certified that error appears in the above-identified patent and that said Letters Patent is hereby corrected as shown below:

In the Claims

Claim 1, Column 51, Line 56, insert --of-- between "conjugate" and "wild-type"

Signed and Sealed this
Third Day of July, 2018

Andrei Iancu
*Director of the United States Patent and Trademark Office*

SEQUENCE LISTING

```
<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: Synthetic primer
```

<400> SEQUENCE: 1
ggactctgga tcccagaagg tg                                            22

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ctgaggttca gagccatgga c                                             21

<210> SEQ ID NO 3
<211> LENGTH: 24
<212> TYPE: DNA
<213> ORGANISM: Artificial Sequence
<220> FEATURE:
<223> OTHER INFORMATION: Synthetic EGFR gene

<400> SEQUENCE: 3
atcaaggaac caacatctcc gaaa                                          24

<210> SEQ ID NO 4
<211> LENGTH: 18
<212> TYPE: DNA
<213> ORGANISM: Artificial Sequence
<220> FEATURE:
<223> OTHER INFORMATION: Synthetic EGFR gene

<400> SEQUENCE: 4
atcaaaacat ctccgaaa                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic EGFR gene

<400> SEQUENCE: 5
atcaagacat ctccgaaa                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic EGFR gene

<400> SEQUENCE: 6
atcaaggaat ctccgaaa                                                 18

<210> SEQ ID NO 7
<211> LENGTH: 15
<212> TYPE: DNA
<213> ORGANISM: Artificial Sequence
<220> FEATURE:
<223> OTHER INFORMATION: Synthetic EGFR gene

<400> SEQUENCE: 7
atcaaggttc cgaaa                                                    15

<210> SEQ ID NO 8

```
<211> LENGTH: 33
<212> TYPE: DNA
<213> ORGANISM: Artificial Sequence
<220> FEATURE:
<223> OTHER INFORMATION: Synthetic EGFR gene

<400> SEQUENCE: 8
atcaaggaat taagagaagc aacatctccg aaa                                    33

<210> SEQ ID NO 9
<211> LENGTH: 137
<212> TYPE: DNA
<213> ORGANISM: Artificial Sequence
<220> FEATURE:
<223> OTHER INFORMATION: Synthetic EGFR gene

<400> SEQUENCE: 9
ggactctgga tcccagaagg tgagaaagtt aaaattcccg tcgctatcaa ggaaccaaca       60
tctccgaaag ccaacaagga atcctcgat gtgagtttct gctttgctgt gtggggtcc       120 atggctctga acctcag                                                     137

<210> SEQ ID NO 10
<211> LENGTH: 131
<212> TYPE: DNA
<213> ORGANISM: Artificial Sequence
<220> FEATURE:
<223> OTHER INFORMATION: Synthetic EGFR gene

<400> SEQUENCE: 10
ggactctgga tcccagaagg tgagaaagtt aaaattcccg tcgctatcaa aacatctccg       60
aaagccaaca aggaaatcct cgatgtgagt ttctgctttg ctgtgtgggg gtccatggct      120
ctgaacctca g                                                           131

<210> SEQ ID NO 11
<211> LENGTH: 131
<212> TYPE: DNA
<213> ORGANISM: Artificial Sequence
<220> FEATURE:
<223> OTHER INFORMATION: Synthetic EGFR gene

<400> SEQUENCE: 11
ggactctgga tcccagaagg tgagaaagtt aaaattcccg tcgctatcaa gacatctccg       60
aaagccaaca aggaaatcct cgatgtgagt ttctgctttg ctgtgtgggg gtccatggct      120
ctgaacctca g                                                           131

<210> SEQ ID NO 12
<211> LENGTH: 131
<212> TYPE: DNA
<213> ORGANISM: Artificial Sequence
<220> FEATURE:
<223> OTHER INFORMATION: Synthetic EGFR gene

<400> SEQUENCE: 12
ggactctgga tcccagaagg tgagaaagtt aaaattcccg tcgctatcaa ggaatctccg       60
aaagccaaca aggaaatcct cgatgtgagt ttctgctttg ctgtgtgggg gtccatggct      120
ctgaacctca g                                                           131

<210> SEQ ID NO 13
<211> LENGTH: 128
<212> TYPE: DNA
<213> ORGANISM: Artificial Sequence
```

```
<220> FEATURE:
<223> OTHER INFORMATION: Synthetic EGFR gene

<400> SEQUENCE: 13
ggactctgga tcccagaagg tgagaaagtt aaaattcccg tcgctatcaa ggttccgaaa    60
gccaacaagg aaatcctcga tgtgagtttc tgctttgctg tgtggggtc catggctctg    120 aacctcag                                                             128

<210> SEQ ID NO 14
<211> LENGTH: 146
<212> TYPE: DNA
<213> ORGANISM: Artificial Sequence
<220> FEATURE:
<223> OTHER INFORMATION: Synthetic EGFR gene

<400> SEQUENCE: 14
ggactctgga tcccagaagg tgagaaagtt aaaattcccg tcgctatcaa ggaattaaga    60
gaagcaacat ctccgaaagc caacaaggaa atcctcgatg tgagtttctg ctttgctgtg    120 tggggtcca tggctctgaa cctcag                                          146

<210> SEQ ID NO 15
<211> LENGTH: 99
<212> TYPE: DNA
<213> ORGANISM: Artificial Sequence
<220> FEATURE:
<223> OTHER INFORMATION: Synthetic Probe

<400> SEQUENCE: 15
ggactctgga tcccagaagg tgagaaagtt aaaattcccg tcgctatcaa ggaattaaga    60
gaagcaacat ctccgaaagc caacaaggaa atcctcgat                           99

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
aaggcctgct gaaaatgact g                                              21

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer

<400> SEQUENCE: 17
ggtcctgcac cagtaatatg ca                                             22

<210> SEQ ID NO 18
<211> LENGTH: 165
<212> TYPE: DNA
<213> ORGANISM: Artificial Sequence
<220> FEATURE:
<223> OTHER INFORMATION: Synthetic KRAS gene

<400> SEQUENCE: 18
aaggcctgct gaaaatgact gaatataaac ttgtggtagt tggagcttgg ggcgtaggca    60
agagtgcctt gacgatacag ctaattcaga atcatttgt ggacgaatat gatccaacaa    120
```
tagaggtaaa tcttgtttta atatgcatat tactggtgca ggacc              165

<210> SEQ ID NO 19
<211> LENGTH: 97
<212> TYPE: DNA
<213> ORGANISM: Artificial Sequence
<220> FEATURE:
<223> OTHER INFORMATION: Synthetic Probe

<400> SEQUENCE: 19
aaggcctgct gaaaatgact gaatataaac ttgtggtagt tggagctggt atatatatat     60
atatataggt gtaggcaaga gtgccttgac gatacag                              97

<210> SEQ ID NO 20
<211> LENGTH: 59
<212> TYPE: DNA
<213> ORGANISM: Artificial Sequence
<220> FEATURE:
<223> OTHER INFORMATION: Synthetic Primer

<400> SEQUENCE: 20
ttgccaacat gacttacttg atccccataa gcatgatgac ctatgatgat aggttttac      59

<210> SEQ ID NO 21
<211> LENGTH: 59
<212> TYPE: DNA
<213> ORGANISM: Artificial Sequence
<220> FEATURE:
<223> OTHER INFORMATION: Synthetic Primer

<400> SEQUENCE: 21
ttgccaacat gacttacttg atccccataa gcatgacaac ctatgatgat aggttttac      59

<210> SEQ ID NO 22
<211> LENGTH: 24
<212> TYPE: DNA
<213> ORGANISM: Artificial Sequence
<220> FEATURE:
<223> OTHER INFORMATION: Synthetic Primer

<400> SEQUENCE: 22
caaatggcac catacgaaat attc                                            24

<210> SEQ ID NO 23
<211> LENGTH: 24
<212> TYPE: DNA
<213> ORGANISM: Artificial Sequence
<220> FEATURE:
<223> OTHER INFORMATION: Synthetic Primer

<400> SEQUENCE: 23
ttgccaacat gacttacttg atcc                                            24

<210> SEQ ID NO 24
<211> LENGTH: 59
<212> TYPE: DNA
<213> ORGANISM: Artificial Sequence
<220> FEATURE:
<223> OTHER INFORMATION: Synthetic Probe

<400> SEQUENCE: 24
ttgccaacat gacttacttg atccccataa gcatgacgtg ataggtttta cccatccac      59

<210> SEQ ID NO 25
<211> LENGTH: 23

```
<212> TYPE: DNA
<213> ORGANISM: Artificial Sequence
<220> FEATURE:
<223> OTHER INFORMATION: Synthetic Primer

<400> SEQUENCE: 25
ggtcaactgc tatgatgtgt ttg                                              23

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
cagcaggtcc cacactcac                                                   19

<210> SEQ ID NO 27
<211> LENGTH: 54
<212> TYPE: DNA
<213> ORGANISM: Artificial Sequence
<220> FEATURE:
<223> OTHER INFORMATION: Synthetic Probe

<400> SEQUENCE: 27
cagcaggtcc cacactcaca gttttcactt cagcccgtac tcgcccaact cccg            54
```